United States Patent [19]

Iwasawa et al.

[11] Patent Number: 5,643,958
[45] Date of Patent: Jul. 1, 1997

[54] SUBSTITUTED AMIDE DERIVATIVES

[75] Inventors: Yoshikazu Iwasawa; Tetsuya Aoyama; Kumiko Kawakami; Sachie Arai; Toshihiko Satoh; Yoshiaki Monden, all of Tsukuba, Japan

[73] Assignee: Banyu Pharmaceutical Co., Ltd., Tokyo, Japan

[21] Appl. No.: 616,308

[22] Filed: Mar. 15, 1996

Related U.S. Application Data

[63] Continuation-in-part of PCT/JP95/01588, Aug. 10, 1995.

[30] Foreign Application Priority Data

Aug. 11, 1994 [JP] Japan ................................. 6-210646
Apr. 10, 1995 [JP] Japan ................................. 7-109067

[51] Int. Cl.[6] ...................... A61K 31/19; C07C 229/24; C07C 229/22
[52] U.S. Cl. .................. 514/568; 514/379; 514/569; 548/217; 549/77; 549/467; 562/427; 562/444; 562/449; 562/450
[58] Field of Search ............... 548/217; 549/77, 549/467; 562/449, 450; 514/379, 568, 569

[56] References Cited

U.S. PATENT DOCUMENTS

| | | | |
|---|---|---|---|
| 5,260,465 | 11/1993 | Singh et al. | 554/134 |
| 5,340,828 | 8/1994 | Graham et al. | 514/357 |
| 5,488,149 | 1/1996 | Nomoto et al. | 562/449 |

FOREIGN PATENT DOCUMENTS

| | | |
|---|---|---|
| 0535730 | 4/1993 | European Pat. Off. . |
| 0547670 | 6/1993 | European Pat. Off. . |
| 5-213992 | 8/1993 | Japan . |
| 5-279290 | 10/1993 | Japan . |

*Primary Examiner*—Bernard Dentz
*Attorney, Agent, or Firm*—Oblon, Spivak, McClelland, Maier & Neustadt, P.C.

[57] ABSTRACT

The present invention relates to a compound of the formula (I):

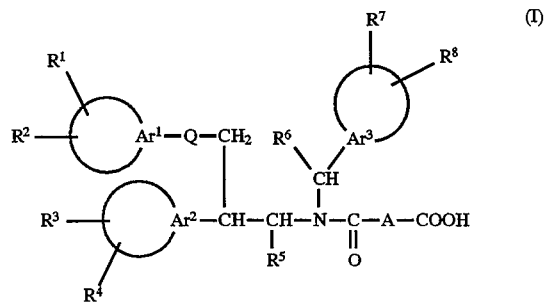

wherein $Ar^1$, $Ar^2$ and $Ar^3$ represent an aryl group or a heteroaromatic ring group; A represents a hydrocarbon group which may be substituted; Q represents a group of the formula $-(CH_2)_m-$ (m is an integer of from 1 to 6) or $-(CH_2)_n-W-(CH_2)_p-$ (W is an oxygen atom, a sulfur atom, a vinylene group or an ethynylene group; n and p are a integer of from 0 to 3); $R^1$ represents a hydrogen atom, a halogen atom, a hydroxyl group, a lower alkyl group, a lower alkoxy group, an aryl or heteroaromatic ring group which may be substituted; $R^2$, $R^7$ and $R^8$ represent a hydrogen atom, a halogen atom, a hydroxyl group, a lower alkyl group or a lower alkoxy group; $R^3$ and $R^4$ represent a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^5$ represents a lower alkyl group; and $R^6$ represents a hydrogen atom or a lower alkyl group, its pharmaceutically acceptable salt or ester, and an antitumor agent containing it as an active ingredient.

7 Claims, No Drawings

SUBSTITUTED AMIDE DERIVATIVES

This application was filed as a International Application PCT/JP95/01588 filed Aug. 10, 1995 of which this application is a continuation in part.

TECHNICAL FIELD

The present invention relates novel substituted amide derivatives. More particularly, the substituted amide derivatives of the present invention inhibit protein-farnesyl transferase (PFT) in vivo thereby to suppress function of oncogene protein Ras and thus present antitumor activities, and they are thus useful as antitumor agents.

BACKGROUND ART

The ras oncogene is activated by mutation, and its translation product Ras protein plays an important role in transformation of normal cells to cancer cells. Such activation of ras oncogene is observed in many cancers such as colorectal cancers or pancreatic cancers, and an proportion thereof is said to reach about 25% of the total human cancers. Accordingly, it is expected that canceration can be suppressed and antitumor effects can be obtained by suppressing such activation of ras oncogene, by inhibiting the function of Ras protein as its product.

Recently, it has been found that farnesyl-modification of Ras protein itself is essential for function of Ras protein, and it is possible to suppress localization of Ras protein at the plasma membrane by inhibiting this farnesyl-modification and thereby to inhibit transformation to cancer cells. The protein-farnesyl transferase (PFT) is an enzyme which catalyses this farnesyl-modification of Ras protein, and by inhibiting this enzyme, it is possible to suppress function of carcinogenic Ras protein. Further, this enzyme contributes to farnesyl-modification of only very limited proteins in vivo. Accordingly, the inhibitor for such an enzyme is expected to be a safe and highly selective antitumor agent. From such a viewpoint, many PFT inhibitors have been developed in recent years (Cell, vol. 57, p. 1167–1177 (1989); Proc. Natl. Acad. Sci., vol. 86, p. 8323–8327 (1989); ditto, vol. 90, p. 2281–2285 (1993); Science, vol. 245, p. 379–385 (1989); ditto, vol. 260, p. 1934–1937 (1993); ditto, vol. 260, p-1937–1942 (1993); J. Biol. Chem., vol. 266, p. 15575–15578 (1991); J. Antibiotics, vol. 46, p. 222–227 (1993); Japanese Unexamined Patent Publications No. 201869/1993 and No. 213992/1993).

However, up to now, all of the reported PFT inhibitors have had some problems for development as medicines, such that the activities are low in cells, and the effects in vivo are inadequate.

DISCLOSURE OF INVENTION

It is an object of the present invention to provide a novel antitumor agent which inhibits the protein-farnesyl transferase (PFT) thereby to inhibit functional manifestation of oncogene protein Ras and which thus provides antitumor effects.

The present inventors have found that a compound of the formula (I):

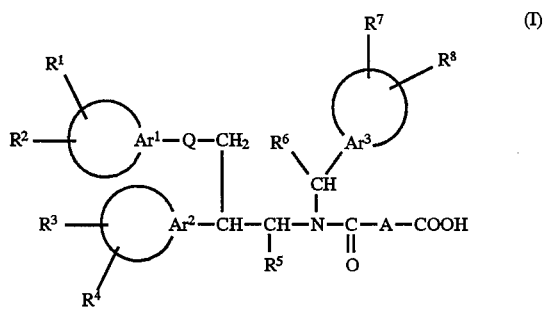

wherein each of

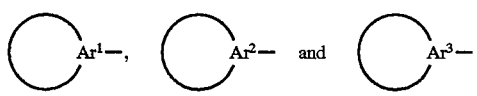

which are the same or different, is an aryl group or a heteroaromatic ring group; A is a $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group; Q is a group of the formula $-(CH_2)_m-$ (wherein m is an integer of from 1 to 6) or $-(CH_2)_n-W-(CH_2)_p-$ (wherein W is an oxygen atom, a sulfur atom, a vinylene group or an ethynylene group; and each of n and p which are the same or different, is an integer of from 0 to 3); $R^1$ is a hydrogen atom, a halogen atom, a hydroxyl group, a lower alkyl group, a lower alkoxy group, or an aryl or heteroaromatic ring group which may have substituent(s) selected from the group consisting of a halogen atom, a lower alkyl group and a lower alkoxy group; each of $R^2$, $R^7$ and $R^8$ which are the same or different, is a hydrogen atom, a halogen atom, a hydroxyl group, a lower alkyl group or a lower alkoxy group; each of $R^3$ and $R^4$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^5$ is a lower alkyl group; and $R^6$ is a hydrogen atom or a lower alkyl group, inhibits the protein-farnesyl transferase (PFT) thereby to suppress function of oncogene protein Ras, and thus is useful as an antitumor agent. The present invention has been accomplished on the basis of this discovery.

Thus, the present invention relates to a compound of the formula (I) or its pharmaceutically acceptable salt or ester, as well as its application as an antitumor agent.

Symbols and terms used in this specification will be explained.

The aryl group means a phenyl group, a naphthyl group or an anthryl group. A phenyl group or a naphthyl group is preferred.

The heteroaromatic ring group means a 5-membered or 6-membered monocyclic aromatic heterocyclic group containing one or two hetero atoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, a pyrimidinyl group, an oxazolyl group, an isoxazolyl group, a thiazolyl group, a benzofuranyl group, a benzothienyl group, a benzimidazolyl group, a benzoxazolyl group, a benzothiazolyl group or a quinolyl group is preferred.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The lower hydroxyalkyl group means the above-mentioned lower alkyl group having a hydroxyl group, i.e. a $C_{1-6}$ hydroxyalkyl group, such as a hydroxymethyl group, a hydroxyethyl group, a hydroxypropyl group or a hydroxybutyl group. Among them, a hydroxymethyl group or a hydroxyethyl group is preferred.

The lower alkoxy group means a $C_{1-6}$ alkoxy or alkylenedioxy group, which may, for example, be a methoxy group, an ethoxy group, a propoxy group, an isopropoxy group, a butoxy group, a tert-butoxy group, a methylenedioxy group, an ethylenedioxy group or a trimethylenedioxy group. Among them, a methoxy group, an ethoxy group or a methylenedioxy group is preferred.

The lower carboxyalkyl group means the above-mentioned lower alkyl group having a carboxyl group, i.e. a $C_{1-7}$ carboxyalkyl group, such as a carboxymethyl group, a carboxyethyl group, a carboxypropyl group or a carboxybutyl group. Among them, a carboxymethyl group or a carboxyethyl group is preferred.

The aralkyl group means the above-mentioned lower alkyl group having the above-mentioned aryl group, such as a benzyl group, a phenethyl group, a 3-phenylpropyl group, a 1-naphthylmethyl group, a 2-naphthylmethyl group or a 1-(2-naphthyl)ethyl group. Among them, a benzyl group, a phenethyl group or a 2-naphthylmethyl group is preferred.

The saturated aliphatic hydrocarbon group may, for example, be an ethylene group, a trimethylene group, a tetramethylene group, a pentamethylene group, a hexamethylene group, a heptamethylene group or an octamethylene group. For example, a trimethylene group, a tetramethylene group or a pentamethylene group is preferred.

The unsaturated aliphatic hydrocarbon group means an unsaturated aliphatic hydrocarbon group having one or more, preferably one or two double bonds, at optional position(s) on the carbon chain, which may, for example, be a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group. Among them, a propenylene group, a 1-butenylene group, a 1,3-butadienylene group or a 1-pentenylene group is preferred.

The halogen atom may be a fluorine atom, a chlorine atom, a bromine atom or an iodine atom. For example, a fluorine atom or a chlorine atom is preferred.

The lower alkoxycarbonyl group means a $C_{1-7}$ alkoxycarbonyl group, such as a methoxycarbonyl group, an ethoxycarbonyl group, a propoxycarbonyl group, a butoxycarbonyl group or a tert-butoxycarbonyl group. Among them, a methoxycarbonyl group or an ethoxycarbonyl group is preferred.

The lower alkylcarbamoyl group means a carbamoyl group mono-substituted or di-substituted by the above-mentioned lower alkyl group, such as a methylcarbamoyl group, an ethylcarbamoyl group, a dimethylcarbamoyl group or a diethylcarbamoyl group.

The lower fluoroalkyl group means the above-mentioned lower alkyl group having fluorine atom(s), i.e. a $C_{1-6}$ fluoroalkyl group, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The salt of the compound of the formula (I) may be a pharmaceutically acceptable common salt, which may, for example, be a base-addition salt of the terminal carboxyl group or of a carboxyl group when $R^3$ and/or $R^4$ is a carboxyl group, or when a carboxyl group or a lower carboxyalkyl group is present on a saturated or unsaturated aliphatic hydrocarbon group represented by A in the formula (I), or an acid-addition salt of an amino group when $R^3$ and/or $R^4$ is an amino group, or of a basic heteroaromatic ring when such a basic heteroaromatic ring is present.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonic acid salt such as a methanesulfonate, an isethionate, a benzenesulfonate or a p-toluenesulfonate.

The ester of the compound of the formula (I) means a pharmaceutically acceptable common ester of the terminal carboxyl group or of a carboxyl group when $R^3$ and/or $R^4$ is a carboxyl group, or when a carboxyl group or a lower carboxyalkyl group is present on the saturated or unsaturated aliphatic hydrocarbon group represented by A in the formula (I). It may, for example, be an ester with a lower alkyl group such as a methyl group, an ethyl group, a propyl group, an isopropyl group, a butyl group, a sec-butyl group, a tert-butyl group, a cyclopropyl group or a cyclopentyl group, an ester with an aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxy alkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group.

Further, when a hydroxyl group is present at the γ- or δ-position of the terminal carboxyl group or of a carboxyl group when such a carboxyl group or a lower carboxyalkyl group is present on the saturated or unsaturated aliphatic hydrocarbon group represented by A in the formula (I), such a hydroxyl group and a carboxyl group may form an intramolecular ester i.e. a 5-membered or 6-membered lactone ring.

Further, the compound of the present invention may have stereoisomers such as optical isomers, diastereomers or geometrical isomers, depending upon the form of its substituents. The compound of the present invention includes all of such stereoisomers and their mixtures. Among them, a compound of the formula (I'-1):

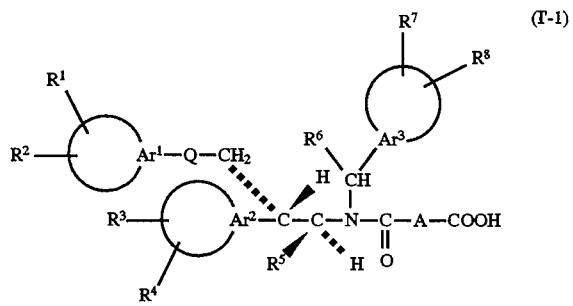

(I'-1)

or the formula (I'-2):

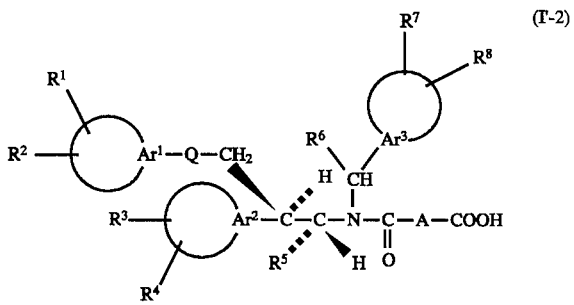

(I'-2)

wherein

A, Q, $R^1$, $R^2$, $R^3$, $R^4$, $R^5$, $R^6$, $R^7$ and $R^8$ are as defined above, is preferred.

When Q is a group of the formula —$(CH_2)_n$—W—$(CH_2)_p$— wherein W, n and p are as defined above, if W is a vinylene group, there exist E-isomer (trans isomer) and Z-isomer (cis isomer) as geometrical isomers based on the vinylene group. Preferred is E-isomer.

The $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group, for A in the formula (I), means the above-mentioned saturated aliphatic hydrocarbon group or the above-mentioned unsaturated aliphatic hydrocarbon group, which is unsubstituted or which may have substituent (s) at optional position(s) for substitution. Such substituent (s) may be one or more, preferably from one to three members, which are the same or different, selected from the group consisting of a lower alkyl group, a hydroxyl group, a lower hydroxyalkyl group, a lower alkoxy group, a carboxyl group, a lower carboxyalkyl group, an aryl group and an aralkyl group.

Preferred is a compound wherein A is a group of the formula (a):

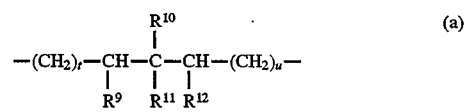

(a)

wherein $R^9$ is a hydrogen atom, a hydroxyl group, a lower hydroxyalkyl group, a lower alkoxy group or a carboxyl group; $R^{10}$ is a hydrogen atom, a hydroxyl group, a lower alkoxy group, a carboxyl group or a lower carboxyalkyl group; $R^{11}$ is a hydrogen atom, a lower hydroxyalkyl group or a carboxyl group; $R^{12}$ is a hydrogen atom, a hydroxyl group or a carboxyl group; and each of t and u which are the same or different, is an integer of from 0 to 2, or a compound wherein A is a group of the formula (b):

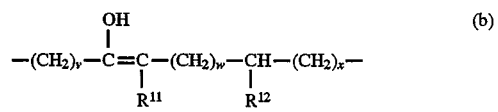

(b)

wherein $R^{11}$ is a hydrogen atom, a lower hydroxyalkyl group or a carboxyl group; $R^{12}$ is a hydrogen atom, a hydroxyl group or a carboxyl group; v is 0 or 1; and each of w and x which are the same or different, is an integer of from 0 to 2.

When A is a group of the formula (a), $R^9$ is preferably a hydrogen atom, a hydroxyl group or a carboxyl group, $R^{10}$ is preferably a carboxyl group or a lower carboxyalkyl group such as a carboxymethyl group, each of $R^{11}$ and $R^{12}$ is preferably a hydrogen atom or a carboxyl group, and each of t and u which are the same or different, is preferably 0 or 1.

When A is a group of the formula (b), $R^{11}$ is preferably a lower hydroxyalkyl group such as a hydroxymethyl group, or a carboxyl group, and $R^{12}$ is preferably a hydrogen atom, and each of v, w and x is preferably 0.

Further, it is well known that in the case of a compound having a partial structure of the formula (b), there exist enol form and keto form tautomers, as shown below. The compound of the present invention includes such enol form and keto form isomers and their mixtures.

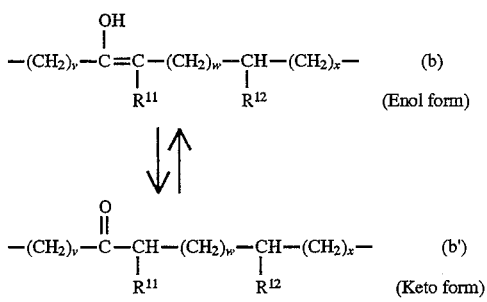

(b) (Enol form)

(b') (Keto form)

In the above formulas, $R^{11}$, $R^{12}$, v, w and x are as defined above.

With respect to Q, when Q is a group of the formula —$(CH_2)_m$— wherein m is as defined above, m is preferably from 1 to 4, and when Q is a group of the formula —$(CH_2)_n$—W—$(CH_2)_p$— wherein W, n and p are as defined above, W is preferably a vinylene group or an ethynylene group, more preferably a vinylene group, and each of n and p which are the same or different, is preferably 0 or 1.

With respect to

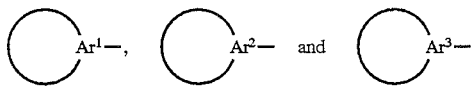

in the compound of the formula (I),

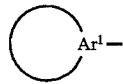

is preferably a phenyl group, a naphthyl group, a benzofuranyl group, a benzothienyl group or a benzoxazolyl group,

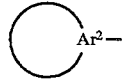

is preferably a phenyl group, and

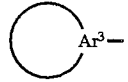

is preferably a naphthyl group, a benzofuranyl group or a benzothienyl group.

$R^1$ is a hydrogen atom, a halogen atom, a hydroxyl group, a lower alkyl group, a lower alkoxy group, or an aryl or heteroaromatic ring group which may have substituent(s) selected from the group consisting of a halogen atom, a lower alkyl group and a lower alkoxy group; and $R^2$ is a hydrogen atom, a halogen atom, a hydroxyl group, a lower alkyl group or a lower alkoxy group. Each of them may be substituted at optional position(s) for substitution on the aryl or beteroaromatic ring group represented by the formula

The aryl or heteroaromatic ring group which may have substituent(s) selected from the group consisting of a halogen atom, a lower alkyl group and a lower alkoxy group, means the above-mentioned aryl or heteroaromatic ring group which is unsubstituted or which have substituent(s) at optional position(s) for substitution. The substituent(s) may be one or more members which are the same or different, selected from the group consisting of a halogen atom, a lower alkyl group and a lower alkoxy group. Among them, the above-mentioned aryl or heteroaromatic ring group which is unsubstituted, is preferred.

In the compound of the formula (I), the group of the formula

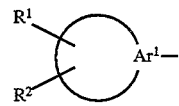

includes, for example, a group of the formula

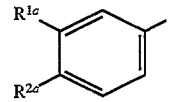

(wherein $R^{1a}$ is a hydrogen atom, a halogen atom, a lower alkyl group or a lower alkoxy group; and $R^{2a}$ is a hydrogen atom, a halogen atom or a lower alkyl group), a naphthyl group, a benzofuranyl group, a benzothienyl group, a benzothiazolyl group, a benzoxazolyl group and a benzimidazolyl group. More specifically, a phenyl group, a 2-benzo[b]furanyl group, a 2-benzo[b]thienyl group, a 2-naphthyl group or a 2-benzoxazolyl group is, for example, preferred.

Each of $R^3$ and $R^4$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group. Each of them may be substituted at optional position(s) for substitution on the aryl or heteroaromatic ring group represented by the formula

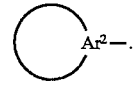

The group of the formula

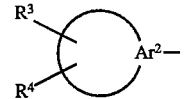

includes, for example, a group of the formula

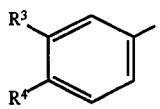

(wherein $R^3$ and $R^4$ are as defined above), a naphthyl group, and a pyridyl, furyl or thienyl group having $R^3$ on the ring. More specifically, a 4-fluorophenyl group, a 4-chlorophenyl group, a 4-methylphenyl group, a 3-fluoro-4-methylphenyl group, a 4-fluoro-3-methylphenyl group, a 3-chloro-4-methylphenyl group, a 4-chloro-3-methylphenyl group, a 3,4-dichlorophenyl group, a 3,4-dimethylphenyl group, a 4-methoxyphenyl group, a 3,4-dimethoxyphenyl group, a 4-nitrophenyl group, a 4-aminophenyl group, a 4-hyroxyphenyl group, a 4-carbamoylphenyl group, a 4-methylcarbamoylphenyl group, a 4-hydroxymethylphenyl group, a 4-trifluoromethylphenyl group, a 4-cyanophenyl group, a 4-methoxycarbonylphenyl group, a 3,4-methylenedioxyphenyl group, a 4-hydroxy-3-methoxyphenyl group, a 3-hydroxy-4-methoxyphenyl group, a 3,4-bis(methoxycarbonyl)phenyl group, a 3,4-bis(hydroxymethyl)phenyl group, a 1-naphthyl group, a 2-naphthyl group, a 5-methylfuryl group, a 5-methylthienyl group or a 6-methyl-3-pyridyl group is, for example, preferred.

$R^5$ is preferably a methyl group, an ethyl group or a propyl group. Particularly preferred is a methyl group or an ethyl group.

$R^6$ is preferably a hydrogen atom, a methyl group, an ethyl group or a propyl group. Particularly preferred is a hydrogen atom or a methyl group.

Each of $R^7$ and $R^8$ which are the same or different, is a hydrogen atom, a halogen atom, a hydroxyl group, a lower alkyl group or a lower alkoxy group, and each of them may be substituted at optional position(s) for substitution on the aryl or heteroaromatic ring group represented by the formula

The group of the formula

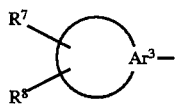

includes, for example, a group of the formula

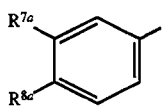

(wherein each of $R^{7a}$ and $R^{8a}$ which are the same or different, is a hydrogen atom, a halogen atom, a lower alkyl group or lower alkoxy group), a naphthyl group, a quinolyl group, a benzoxazolyl group, a benzofuranyl group and a benzothienyl group. More specifically, a 3,4-dichlorophenyl group, a 3,4-difluorophenyl group, a 3,4-dimethylphenyl group, a 2-naphthyl group, a 2-benzoxazolyl group, a 2-benzo[b]furanyl group, a 2-benzo[b]thienyl group or a 5-benzo[b]thienyl group is, for example, preferred.

Now, processes for producing the compound of the present invention will be described.

The compound of the formula (I) of the present invention can be prepared, for example, by the following process 1, 2, 3, 4, 5, 6 or 7.

Process 1

The compound of the formula (I) can be prepared by reacting a compound of the formula (II):

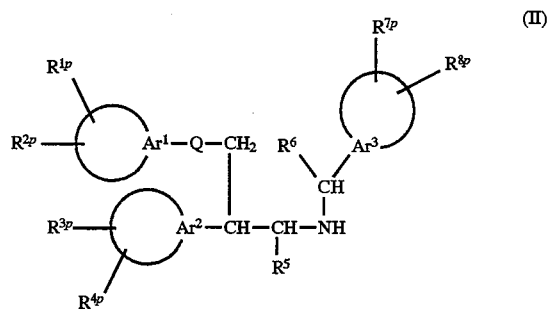

(II)

wherein each of

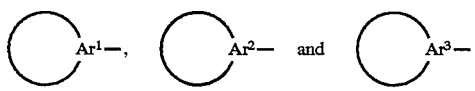

which are the same or different, is an aryl group or a heteroaromatic ring group; Q is a group of the formula —$(CH_2)_m$— (wherein m is an integer of from 1 to 6) or —$(CH_2)_n$—W—$(CH_2)_p$— (wherein W is an oxygen atom, a sulfur atom, a vinylene group or an ethynylene group; and each of n and p which are the same or different, is an integer of from 0 to 3); $R^{1p}$ is a hydrogen atom, a halogen atom, a hydroxyl group which may be protected, a lower alkyl group, a lower alkoxy group, or an aryl or heteroaromatic ring group which may have substituent(s) selected from the group consisting of a halogen atom, a lower alkyl group and a lower alkoxy group; each of $R^{2p}$, $R^{7p}$ and $R^{8p}$ which are the same or different, is a hydrogen atom, a halogen atom, a hydroxyl group which may be protected, a lower alkyl group or a lower alkoxy group; each of $R^{3p}$ and $R^{4p}$ which are the same or different, is a hydrogen atom, a halogen atom, a nitro group, a cyano group, a lower alkoxycarbonyl group, a carbamoyl group, a lower alkylcarbamoyl group, a lower alkyl group, a lower fluoroalkyl group, a lower alkoxy group or a hydroxyl, amino, carboxyl or lower hydroxyalkyl group which may be protected; $R^5$ is a lower alkyl group; and $R^6$ is a hydrogen atom or a lower alkyl group, with a carboxylic acid of the formula (III) or its reactive derivative:

(III)

wherein $A^p$ is a $C_{2-8}$ saturated or unsaturated aliphatic hydrocarbon group which may have substituent(s) selected from the group consisting of a lower alkyl group, a lower alkoxy group, an aryl group, an aralkyl group, and hydroxyl, lower hydroxyalkyl, carboxyl and lower carboxyalkyl groups which may be protected; and $R^p$ is a hydrogen atom or a carboxyl-protecting group, to obtain a compound of the formula (IV):

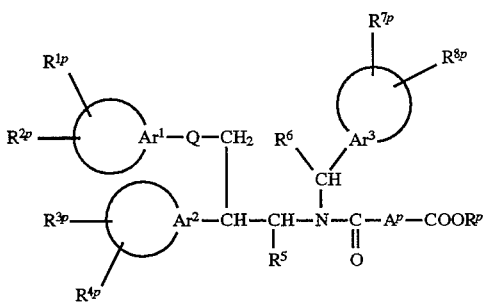

(IV)

wherein

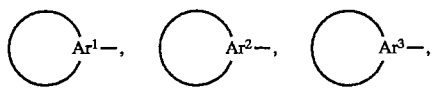

$A^p$, Q, $R^{1p}$, $R^{2p}$, $R^{3p}$, $R^{4p}$, $R^5$, $R^6$, $R^{7p}$, $R^{8p}$ and $R^p$ are as defined above, and, if necessary, removing any protecting group.

As the reactive derivative of the carboxylic acid of the formula (III), an acid halide, a mixed acid anhydride, an active ester or an active amide may, for example, be used.

When the carboxylic acid of the formula (III) is used, it is preferred to conduct the reaction in the presence of a condensing agent such as N,N'-dicyclohexylcarbodiimide, 1-ethyl-3-(3-dimethylaminopropyl)carbodiimide or 2-chloro-1,3-dimethylimidazolyl chloride.

The reaction of the compound of the formula (II) with the carboxylic acid of the formula (III) or its reactive derivative, is conducted usually by using 1 mol or an excess molar amount, preferably from 1 to 5 mols, of the carboxylic acid of the formula (III) or its reactive derivative, per mol of the compound of the formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction the is usually from 5 minutes to 7 days, preferably from 10 minutes to 24 hours.

The above reaction can be conducted in the presence of a base to facilitate the reaction. As such a base, it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid of the formula (III).

The acid halide of the compound of the formula (III) can be obtained by reacting the carboxylic acid of the formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound of the formula (III) can be obtained by reacting the carboxylic acid of the formula (III) with an alkyl chlorocarbonate such as ethyl chlorocarbonate or with an aliphatic carboxylic acid chloride such as acetyl chloride, in accordance with a conventional method. Further, an intramolecular acid anhydride may be formed between carboxyl groups at both terminals, or when in the formula (III), a carboxyl group is present on the saturated or unsaturated aliphatic hydrocarbon group for $A^p$, an intramolecular acid anhydride may be formed between such a carboxyl group and a carboxyl group to be involved in the reaction, to constitute a reactive derivative of the carboxylic acid.

The active ester of the compound of the formula (III) can be prepared by reacting the carboxylic acid of the formula (III) with an N-hydroxy compound such as N-hydroxysuccinimide, N-hydroxyphthalimide or 1-hydroxybenzotriazole, or a phenol compound such as a 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound of the formula (III) can be prepared by reacting the carboxylic acid of the formula (III) with e.g. 1,1'-carbonyldiimidazole or 1,1'-carbonylbis (2-methylimidazole) in accordance with a conventional method.

When a hydroxyl group is present on the group of the formula

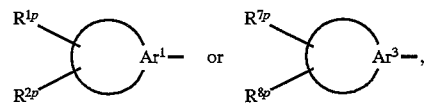

when a hydroxyl group, a lower hydroxyalkyl group, a carboxyl group or a lower carboxyalkyl group is present on the saturated or unsaturated aliphatic hydrocarbon group represented by $A^p$, and when a hydroxyl group, an amino group, a carboxyl group or a lower hydroxyalkyl group is present on the group of the formula

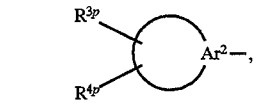

it is preferred to conduct the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group and removing the protecting group after the reaction.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The amino-protecting group may, for example, be an aralkylidene group such as a benzylidene group, a p-chlorobenzylidene group or a p-nitrobenzylidene group; an aralkyl group such as a benzyl group, a p-methoxybenzyl group, a p-nitrobenzyl group, a benzhydryl group or a trityl group; a lower alkanoyl group such as a formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group. Particularly preferred is an acetyl group, a trifluoroacetyl group, a tert-butoxycarbonyl group or a benzyloxycarbonyl group.

The carboxyl-protecting group may, for example, be a lower alkyl group such as a methyl group, an ethyl group, a propyl group, an isopropyl group or a tert-butyl group; a lower haloalkyl group such as a 2,2,2-trichloroethyl group; a lower alkenyl group such as 2-propenyl group; or an aralkyl group such as a benzyl group, a p-methoxybenzyl group, a p-nitrobenzyl group, a benzhydryl group or a trityl group. Particularly preferred is a methyl group, an ethyl group, a tert-butyl group, a 2-propenyl group, a benzyl group, a p-methoxybenzyl group or a benzhydryl group.

After completion of the reaction, conventional treatment is conducted to obtain a crude product of the compound of the formula (IV). The compound of the formula (IV) may or may not be purified in accordance with a conventional method, and if necessary, reactions for removing protecting groups such as a hydroxyl group, an amino group and a carboxyl group, are appropriately conducted to obtain a compound of the formula (I).

Removal of protecting groups may vary depending upon their types, but can be conducted in accordance with the methods disclosed in a literature (Protective Groups in Organic Synthesis, T. W. Greene, John Wiley & Sons (1981)) or methods similar thereto, for example by solvolysis employing an acid or a base, by chemical reduction employing a metal hydride complex or by catalytic reduction employing a palladium-carbon catalyst or Raney nickel.

Process 2

A compound of the formula (I-1):

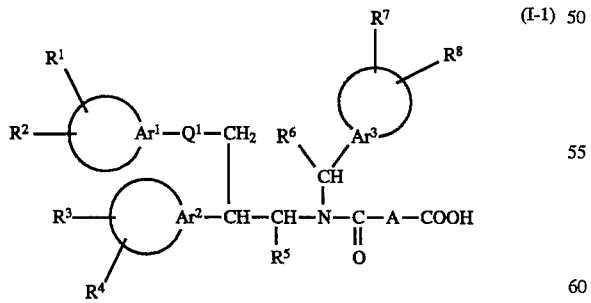
(I-1)

wherein $Q^1$ is —$(CH_2)_n$—CH=CH—$(CH_2)_p$—(wherein n and p are as defined above); and

A, $R^1$, $R^2$, $R^3$, $R^5$, $R^5$, $R^6$, $R^7$ and $R^8$ are as defined above, can be prepared by reacting a compound of the formula (V):

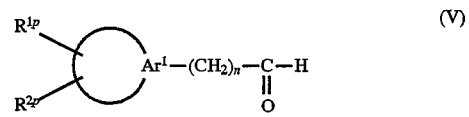
(V)

wherein

$R^{1p}$, $R^{2p}$ and n are as defined above, with a compound of the formula (VI):

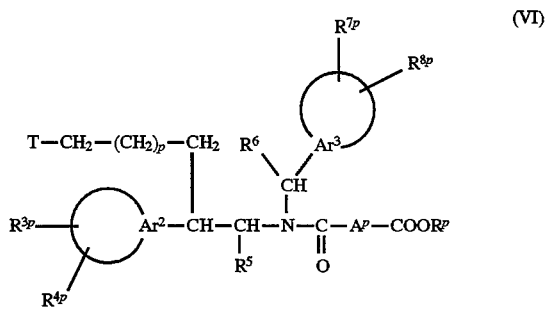
(VI)

wherein T is a triphenylphosphonio group, a dimethoxyphosphoryl group or a diethoxyphosphoryl group; and

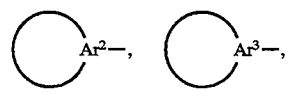

$A^p$, P, $R^{3p}$, $R^{4p}$, $R^5$, $R^6$, $R^{7p}$, $R^{8p}$ and $R^p$ are as defined above, to obtain a compound of the formula (IV-1):

(IV-1)

[Chemical structure diagram of formula (IV-1)]

wherein

[Ar¹—, Ar²—, Ar³— ring structures]

$A^p$, n, p $R^{1p}$, $R^{2p}$, $R^{3p}$, $R^{4p}$, $R^5$, $R^6$, $R^{7p}$, $R^{8p}$ and $R^p$ are as defined above, and, if necessary, removing any protecting group.

Process 2 is a process for preparing a compound of the formula (I) wherein Q is —(CH$_2$)$_n$—CH=CH—(CH$_2$)$_p$— (wherein n and p are as defined above) i.e. a compound of the formula (I-1).

The reaction of the compound of the formula (V) with a compound of the formula (VI) is carried out usually by employing equimolar amounts of the two reactants or using a slightly excess amount of one of them.

The reaction is carried out usually in an inert solvent. Such an inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide; or a mixture of such solvents.

The reaction temperature is usually from –100° C. to the boiling point of the solvent used for the reaction, preferably from –70° C. to 50° C.

The reaction time is usually from 5 minutes to 7 days, preferably from 10 minutes to 24 hours.

Further, the above reaction can be conducted in the presence of a base to facilitate the reaction. Especially when T in the formula (VI) is a triphenylphosphonio group, the reaction is preferably conducted in the presence of a base such as sodium hydride, n-butyl lithium, sodium methoxide, potassium tert-butoxide, sodium hydroxide or potassium hydroxide.

Such a base is used in an amount of one mol or an excess molar amount, preferably from 1 to 5 mols per mol of the compound wherein T is a triphenylphosphonio group. When a hydroxyl group is present on the group of the formula

[Structures with $R^{1p}$, $R^{2p}$, Ar¹— or $R^{7p}$, $R^{8p}$, Ar³—]

when a hydroxyl group, a lower hydroxyalkyl group, a carboxyl group or a lower carboxyalkyl group is present on the saturated or unsaturated aliphatic hydrocarbon group represented by $A^p$, and when a hydroxyl group, an amino group, a carboxyl group or a lower hydroxyalkyl group is present on the group of the formula it is preferred to carry out the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group, and removing any protecting group after the reaction.

The hydroxyl-protecting group, the amino-protecting group and the carboxyl-protecting group may be the protecting groups mentioned above with respect to process 1.

After completion of the reaction, a conventional treatment may be carried out to obtain a crude product of the compound of the formula (IV-1). The compound of the formula (IV-1) thus obtained may or may not be purified by a conventional method, and if necessary, reactions for removing hydroxyl-, amino- and carboxyl-protecting groups may be carried out in a proper combination to obtain a compound of the formula (I-1).

The method for removing a protecting group varies depending upon the type of the protecting group and the stability of the desired compound (I-1). However, removal of protecting groups can be suitably conducted in accordance with the methods disclosed in the above-mentioned literature or methods similar thereto.

Process 3

A compound of the formula (I-1):

(I-1)

[Chemical structure diagram of formula (I-1)]

wherein

[Ar¹—, Ar²—, Ar³— ring structures]

A, $Q^1$, $R^1$, $R^2$, $R^3$, $R^4$, $R^5$, $R^6$, $R^7$ and $R^8$ are as defined above, can be obtained by reacting a compound of the formula (VII):

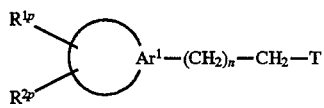
(VII)

wherein

T, N, $R^{1p}$ and $R^{2p}$ are as defined above, with a compound of the formula (VIII):

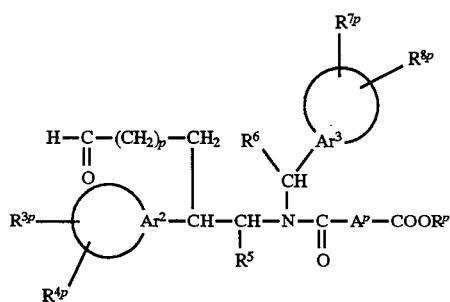
(VIII)

wherein

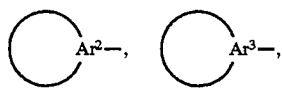

$A^p$, p, $R^{3p}$, $R^{4p}$, $R^5$, $R^6$, $R^{7p}$, $R^{8p}$ and $R^p$ are as defined above, to obtain a compound of the formula (IV-1):

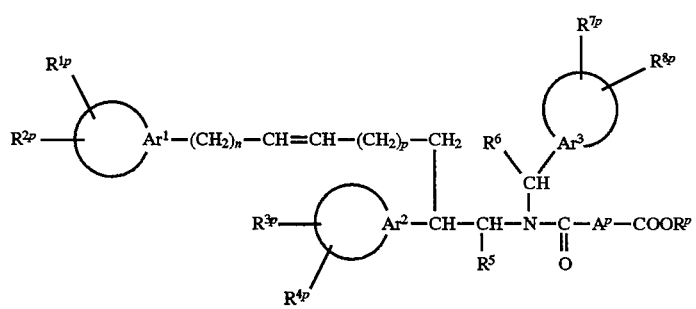
(IV-1)

wherein

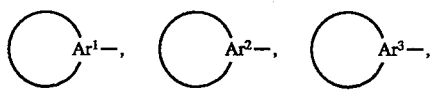

$A^p$, n, p, $R^{1p}$, $R^{2p}$, $R^{3p}$, $R^{4p}$, $R^5$, $R^6$, $R^{7p}$, $R^{8p}$ and $R^p$ are as defined above, and, if necessary, removing any protecting group.

Like process 2, process 3 is a process for producing a compound of the formula (I) wherein Q is $-(CH_2)_n-CH=CH-(CH_2)_p-$ (wherein n an p are as defined above) i.e. a compound of the formula (I-1).

Process 3 is equal to the reaction of process 2 wherein staring material compounds (V) and (VI) are replaced by the compounds (VIII) and (VII), respectively. Accordingly, the manner and conditions of the reaction may be all in accordance with process 2.

Process 4

A compound of the formula (I-2):

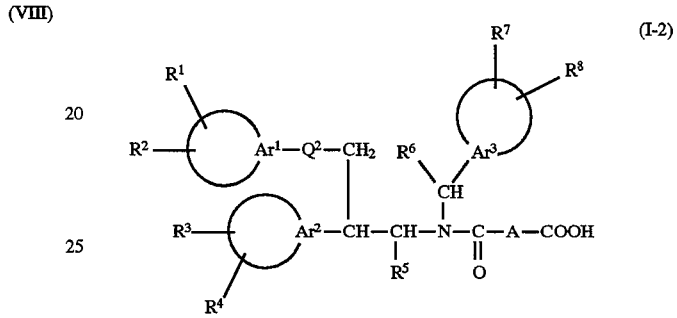
(I-2)

wherein $Q^2$ is $-(CH_2)_m-$ (wherein m is as defined above); and

A, $R^1$, $R^2$, $R^3$, $R^4$, $R^5$, $R^6$, $R^7$ and $R^8$ are as defined above, can be obtained by reducing a compound of the formula (IV-1'):

(IV-1')

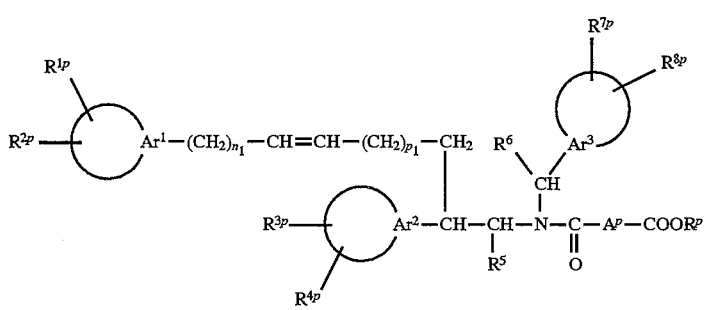

wherein each of $n_1$ and $p_1$ which are the same or different, is an integer of from 0 to 3; and

$A^p$, $R^{1p}$, $R^{2p}$, $R^{3p}$, $R^{4p}$, $R^5$, $R^6$, $R^{7p}$, $R^{8p}$ and $R^p$ are as defined above (provided that the sum of $n_1$ and $P_1$ does not exceed 4), and, if necessary, removing any protecting group.

Process 4 is a process for producing a compound of the formula (I) wherein Q is —$(CH_2)_m$— (wherein m is as defined above) i.e. a compound of the formula (I-2).

The reaction of reducing the compound of the formula (IV-1') is usually preferably conducted by catalytic reduction employing a palladium-carbon catalyst, a Raney nickel catalyst or a platinum catalyst in an inert solvent.

The inert solvent may, for example, be an alcohol such as methanol, ethanol or propanol, or acetic acid.

The reaction temperature is usually from –20° C. to 100° C., preferably from 0° C. to room temperature.

The reaction time is usually from 5 minutes to 7 days, preferably from 10 minutes to 24 hours.

The hydrogen pressure in the catalytic reduction reaction is usually preferably from atmospheric pressure to 5 atm, and the amount of the catalyst is usually from 0.01 to 1 mol, preferably from 0.05 to 0.2 mol, per mol of the starting material compound (IV-1').

After completion of the reaction, the product is subjected to a usual treatment after removing any protecting group if such a protecting group is present or directly if no such protecting group is present, to obtain a compound of the formula (I-2).

Removal of the protecting group and the post treatment may be conducted by the methods described with respect to the above process 1.

Process 5

A compound of the formula (I-3):

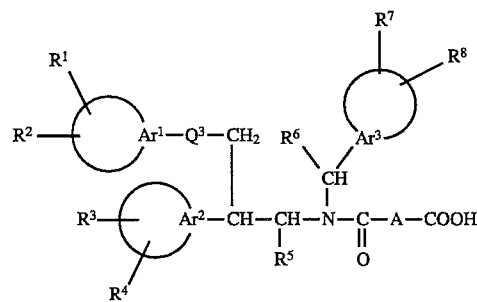

(I-3)

wherein $Q^3$ is —$(CH_2)_n$—$W^1$—$(CH_2)_p$— (wherein n, p and $W^1$ are as defined above); and

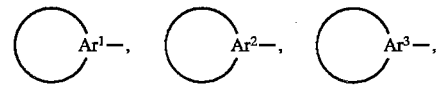

A, $R^1$, $R^2$, $R^3$, $R^4$, $R^5$, $R^6$, $R^7$ and $R^8$ are as defined above, can be prepared by reacting a compound of the formula (IX):

(IX)

$R^{1p}$—Ar$^1$—$(CH_2)_n$—$W^1$—H
$R^{2p}$ wherein $W^1$ is an oxygen atom or a sulfur atom; and

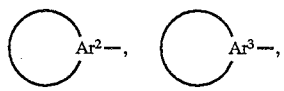

n, $R^{1p}$ and $R^{2p}$ are as defined above, with a compound of the formula (X):

(X)

wherein $Z^1$ is a leaving group; and $A^p$, p, $R^{3p}$, $R^{4p}$, $R^5$, $R^6$, $R^{7p}$, $R^{8p}$ and $R^p$ are as defined above, to obtain a compound of the formula (IV-3);

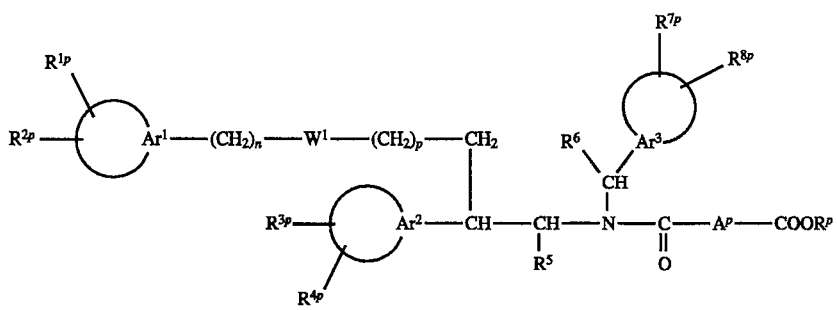

wherein

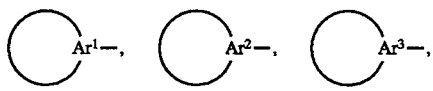

$A^p$, n, p, $W^1$, $R^{1p}$, $R^{2p}$, $R^{3p}$, $R^{4p}$, $R^5$, $R^6$, $R^{7p}$, $R^{8p}$ and $R^p$ are as defined above, and, if necessary, removing any protecting group.

Process 5 is a process for preparing a compound of the formula (I) wherein Q is —$(CH_2)_n$—$W^1$—$(CH_2)_p$— (wherein n, p and $W^1$ are as defined above) i.e. a compound of the formula (I-3).

The reaction of the compound of the formula (IX) with a compound of the formula (X) is carried out usually by using 1 mol or an excess molar amount, preferably from 1 to 3 mols, of the compound of the formula (IX), per mol of the compound of the formula (X).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction is preferably conducted in the presence of a base to facilitate the reaction. Such a base may, for example, be an inorganic base such as sodium hydride, n-butyl lithium, sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

The base is used usually in an amount of 1 mol or an excess molar amount, preferably from 1 to 5 mols, per mol of the compound of the formula (IX).

The leaving group represented by $Z^1$ may, for example, be a halogen atom such as a chlorine atom, a bromine atom or an iodine atom, or an organic sulfonyloxy group such as a methanesulfonyloxy group, a p-toluenesulfonyloxy group or a benzenesulfonyloxy group.

When a hydroxyl group is present on the group of the formula

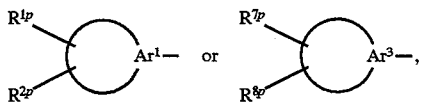

when a hydroxyl group, a lower hydroxyalkyl group, a carboxyl group or a lower carboxyalkyl group is present on the saturated or unsaturated aliphatic hydrocarbon group represented by $A^p$, and when a hydroxyl group, an amino group, a carboxyl group or a lower hydroxyalkyl group is present on the group of the formula

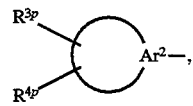

it is preferred to conduct the reaction after protecting such a hydroxyl group, a lower hydroxyalkyl group, an amino group, a carboxyl group or a lower alkoxyalkyl group appropriately by a hydroxyl-protecting group, an amino-protecting group or a carboxyl-protecting group and removing any protecting group after the reaction.

The hydroxyl-protecting group, the amino-protecting group and the carboxyl-protecting group may be the protecting groups mentioned above with respect to process 1.

After completion of the reaction, a usual treatment is carried out to obtain a crude product of the compound of the formula (IV-3). The compound of the formula (IV-3) thus obtained may or may not be purified by a conventional method, and reactions for removing the hydroxyl-, amino- and carboxyl-protecting groups may be carried out in a proper combination, to obtain a compound of the formula (I-3). The method for removing a protecting group varies depending upon the type of the protecting group and the stability of the desired compound (I-3). However, removal of protecting groups can be appropriately conducted in accordance with the methods disclosed in the above-mentioned literature or methods similar thereto.

Process 6

A compound of the formula (I-3):

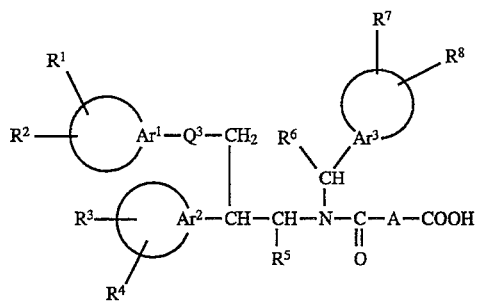

wherein

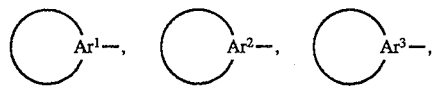

A, $Q^3$, $R^1$, $R^2$, $R^3$, $R^4$, $R^5$, $R^6$, $R^7$ and $R^8$ are as defined above, can be prepared by reacting a compound of the formula (XI):

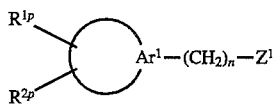

wherein

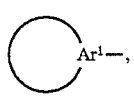

n, $Z^1$, $R^{1p}$ and $R^{2p}$ are as defined above, with a compound of the formula (XII):

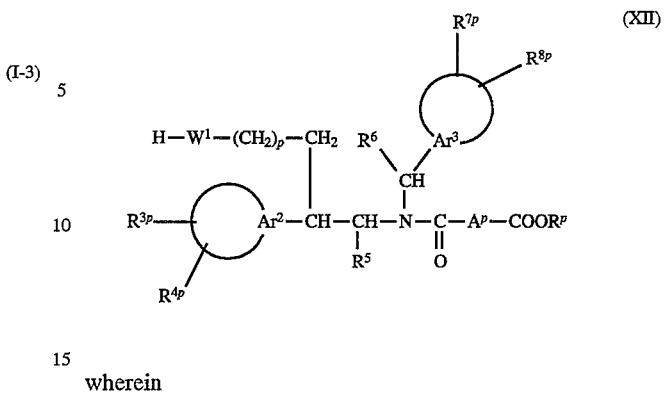

wherein

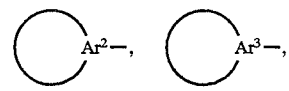

$A^p$, p, $W^1$, $R^{3p}$, $R^{4p}$, $R^5$, $R^6$, $R^{7p}$, $R^{8p}$ and $R^p$ are as defined above, to obtain a compound of the formula (IV-3):

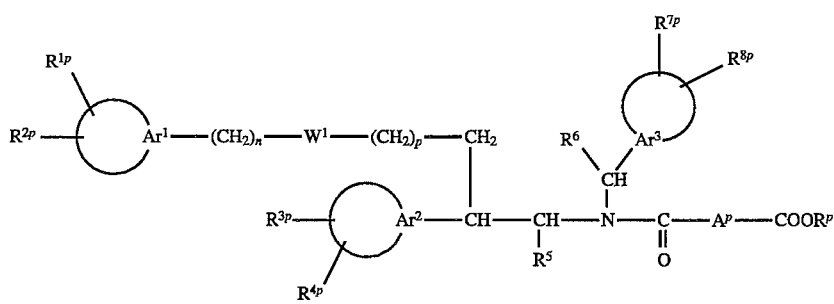

wherein

$A^p$, n, p, $W^1$, $R^{1p}$, $R^{2p}$, $R^{3p}$, $R^{4p}$, $R^5$, $R^6$, $R^{7p}$, $R^{8p}$ and $R^p$ are as defined above, and, if necessary, removing any protecting group.

Like the above process 5, process 6 is a process for preparing a compound of the formula (I) wherein Q is $-(CH_2)_n-W^1-(CH_2)_p-$ (wherein n, p and $W^1$ are as defined above) i.e. a compound of the formula (I-3).

This process can be conducted usually in an inert solvent, preferably in the presence of a base, by using 1 mol or an excess molar amount, preferably from 1 to 3 mols, of the compound of the formula (XI), per mol of the compound of the formula (XII). The types of the inert solvent and the base as well as the reaction conditions may be the same as described above with respect to process 5. Accordingly, the reaction and the post-treatment after the reaction may preferably be carried out all in accordance with process 5.

Process 7

A compound of the formula (I-4):

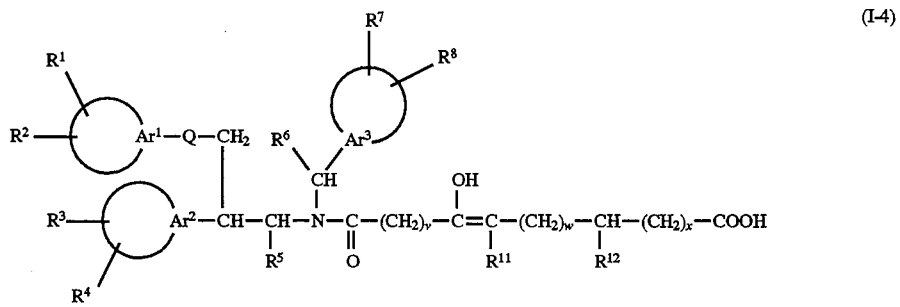

(I-4)

wherein

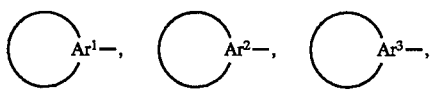

Q, $R^1$, $R^2$, $R^3$, $R^4$, $R^5$, $R^6$, $R^7$, $R^8$, $R^{11}$, $R^{12}$ v, w and x are as defined above, can be prepared by oxidising a compound of the formula (IV-4):

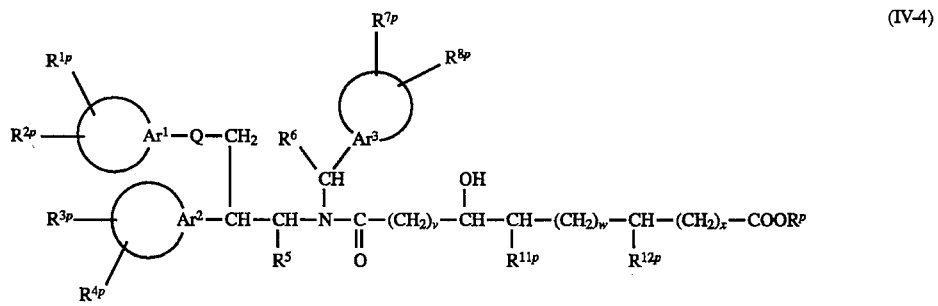

(IV-4)

wherein $R^{11p}$ is a hydrogen atom or a lower hydroxyalkyl or carboxyl group which may be protected, $R^{12p}$ is a hydrogen atom or a hydroxyl or carboxyl group which may be protected; and

Q, $R^{1p}$, $R^{2p}$, $R^{3p}$, $R^{4p}$, $R^5$, $R^6$, $R^{7p}$, $R^{8p}$, $R^p$, v, w and x are as defined above, and, if necessary, removing any protecting group.

Process 7 is a process for preparing a compound of the formula (I) wherein A is a group of the formula (b):

$$-(CH_2)_v-C=C-(CH_2)_w-CH-(CH_2)_x- \atop \quad R^{11} \qquad\qquad R^{12} \atop \text{OH}$$

(b)

wherein $R^{11}$, $R^{12}$, v, w end x are as defined above, i.e. a compound of the formula (I-4).

The reaction of oxidizing the compound of the formula (IV-4) is usually preferably carried out in an inert solvent by using so-called Dess-Martin oxidation employing 12-I-5 triacetoxyperiodinane; so-called Swern oxidation employing oxalyl chloride and dimethyl sulfoxide; a sulfur trioxide-pyridine complex; pyridinium chlorochromate; active manganese dioxide; or tetra-n-propylammonium perruthenate.

The inert solvent may, for example, be a halogenated hydrocarbon such as methylene chloride, chloroform or dichloroethane; an ether such as ethyl ether, tetrahydrofuran or dioxane; an aprotic polar solvent such as acetonitrile, acetone, ethyl acetate or dimethyl sulfoxide; or a mixture of such solvents.

The reaction temperature varies depending upon the type of the oxidizing agent, etc. However, it is usually from –100° C. to the boiling point of the solvent used for the reaction, preferably from –70° C. to 100° C.

The reaction time is usually from 5 minutes to 7 days, preferably from 10 minutes to 24 hours.

After completion of the reaction, the product is subjected to usual treatment after removing a protecting group when such a protecting group is present, or directly when no such protecting group is present, to obtain the compound of the formula (I-4).

The removal of the protecting group and the post-treatment may be conducted in the same manner as described above with respect to process 1.

Further, a compound corresponding to the compound of the formula (IV-4) to be used as the starting material in the above process 7, can be prepared, for example, by hydrolyzing a compound of the formula (IV-4a):

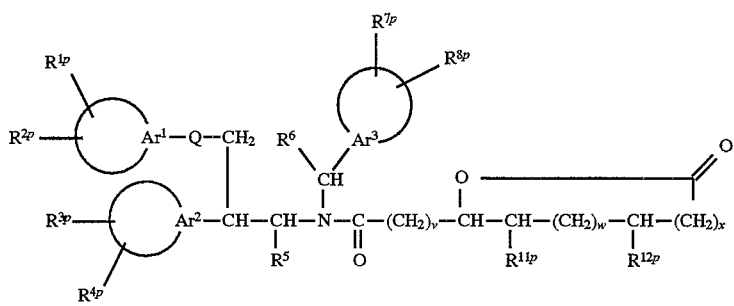
(IV-4a)

wherein

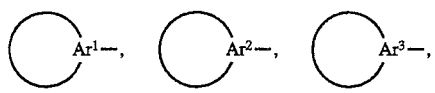

Q, $R^{1p}$, $R^{2p}$, $R^{3p}$, $R^{4p}$, $R^5$, $R^6$, $R^{7p}$, $R^{8p}$, $R^{11p}$, $R^{12p}$, v, w and x are as defined above, in the presence of a base, to obtain a compound of the formula (IV-4b):

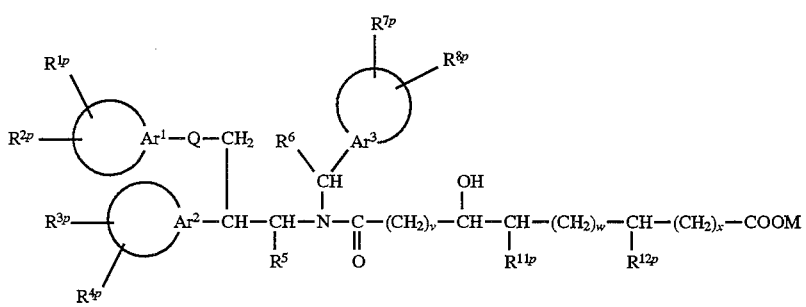
(IV-4b)

wherein M is a hydrogen atom or an alkali metal atom; and

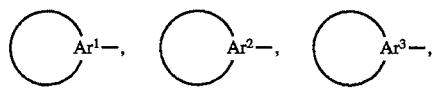

Q, $R^{1p}$, $R^{2p}$, $R^{3p}$, $R^{4p}$, $R^5$, $R^6$, $R^{7p}$, $R^{8p}$, $R^{11p}$, $R^{12p}$, v, w and x are as defined, then reacting thereto a diazo compound of the formula

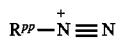

wherein $R^{pp}$ is a lower alkyl group, a lower alkenyl group, an aralkyl group or a lower alkoxycarbonylalkyl group, or an alkylating agent of the formula $R^{pp}$-Z wherein $R^{pp}$ and Z are as defined above.

Isolation and purification of the compound of the formula (I), (I-1), (I-2), (I-3) or (I-4), obtained by the above process can be conducted by a single use or a proper combination of conventional separating means such as column chromatography employing silica gel, adsorbent resin, etc., liquid chromatography, solvent extraction and recrystallization-reprecipitation.

The compound of the formula (I), (I-1), (I-2), (I-3) or (I-4) can be converted to a pharmaceutically acceptable salt or ester by a conventional method. Reversely, the conversion from the salt or ester to a free carboxylic acid can also be conducted by a conventional method.

Further, compounds of the present invention can all be prepared by the processes similar to the above processes by using the starting materials corresponding to the desired compounds.

The compounds of the formulas (II), (III), (V), (VI), (VII), (VIII), (IX), (X), (XI) and (XII) may be commercially available or can be prepared in accordance with the methods disclosed in literatures (J. Med. Chem., 10, 717 (1967); ibid., 725; J. Chem. Soc. Perkin I, 1636 (1978); Chem. Lett., 191 (1980); ibid., 375 (1984); J. Chem. Soc. Chem. Commun., 579 (1984); J. Am. Chem. Soc., 104, 5716 (1982)) or methods similar thereto, or in accordance with the following processes or the methods disclosed in Reference Examples.

Process A

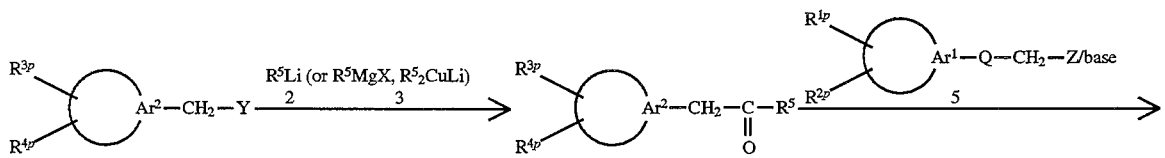

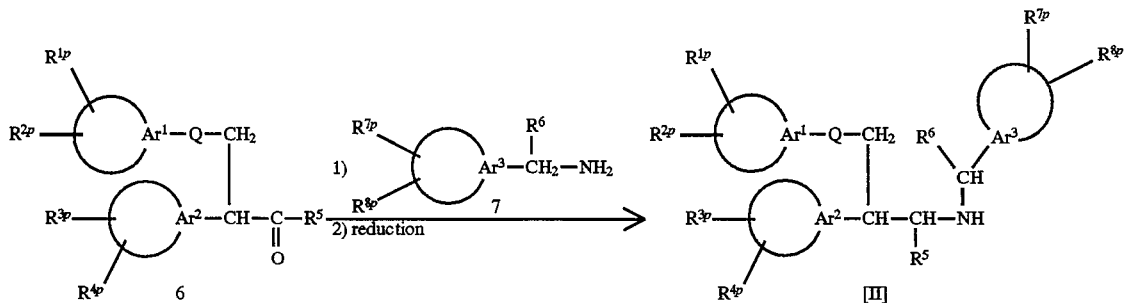

In the above formulas,

Q, $R^{1p}$, $R^{2p}$, $R^{3p}$, $R^{4p}$, $R^5$, $R^6$, $R^{7p}$ and $R^{8p}$ are as defined above; X is a halogen atom; Y is a cyano group, a carboxyl group, a lower alkoxycarbonyl group, a chloroformyl group or an N-methoxy-N-methylcarbamoyl group; Z is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group.

By this process, the desired compound (II) can be prepared by reacting a nitrile or a carboxylic acid derivative of the formula 1 with an alkyl lithium of the formula 2 or an alkyl Grignard reagent (or an alkyl Gilman reagent) of the formula 3 to obtain a ketone compound 4, then reacting an alkylating agent of the formula 5 to the ketone compound 4 to produce a compound of the formula 6, then reacting the compound 6 with an amine compound of the formula 7, followed by reduction.

The above reaction steps will be described in detail referring to suitable reaction conditions, etc.

The first step of preparing the ketone compound 4 is conducted usually by reacting 1 mol or an excess molar amount, preferably from 1 to 5 mols of the alkyl lithium reagent 2 or the alkyl Grignard reagent (or the alkyl Gilman reagent in the case where the substituent Y of the compound 1 is a chloroformyl group) 3 to 1 mol of the starting material compound 1 in a solvent inert to the reaction such as tetrahydrofuran, ethyl ether or benzene, if necessary followed by hydrolysis under an acidic condition.

The reaction temperature is usually from −80° C. to the boiling point of the solvent used for the reaction, preferably from −70° C. to 50° C. The reaction time is usually from 5 minutes to 48 hours, preferably from 30 minutes to 24 hours.

When the substituent Y in the formula of the starting material compound 1 is a cyano group, it may be necessary to conduct a hydrolytic reaction under an acidic condition after completion of the reaction, and such a hydrolyric reaction is conducted in e.g. methanol, ethanol, tetrahydrofuran or a solvent mixture thereof with water in the presence of an acid such as hydrochloric acid, sulfuric acid or p-toluenesulfonic acid.

The reaction temperature is usually from 0° C. to the boiling point of the solvent used for the reaction, and the reaction time is from 30 minutes to 24 hours.

The step of preparing the compound of the formula 6 from the ketone compound 4, can be conducted by reacting an equimolar amount or an excess molar amount, preferably from 1 to 2 mols, of the alkylating agent of the formula 5 to the ketone compound 4 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis (trimethylsilyl)amide; an alkyl lithium such as methyl lithium, butyl lithium or tert-butyl lithium; an alkali metal alkoxide such as sodium methoxide, sodium ethoxide or potassium tert-butoxide; or an alkali metal hydroxide such as sodium hydroxide, potassium hydroxide or lithium hydroxide.

The base is used usually in an amount of 1 mol or an excess molar amount, preferably from 1 to 5 mols, per mol of the starting material alkylating agent 5.

The reaction temperature is usually from −100° C. to the boiling point of the solvent used for the reaction, preferably from −80° C. to 100° C. The reaction time is usually from 10 minutes to 48 hours, preferably from 30 minutes to 24 hours.

The step of preparing the desired compound (II) from the compound of the formula 6 can be conducted usually in an inert solvent such as methanol, ethanol, benzene, ethyl ether or tetrahydrofuran by reacting 1 mol or an excess molar amount, preferably from 1 to 2 mols, of the amine compound of the formula 7 to 1 mol of the compound of the formula 6 to preliminarily form an imine, which is subsequently reduced.

The reaction temperature in the process for forming the above imine is usually from 0° C. to the boiling point of the solvent used for the reaction, preferably from room temperature to 100° C. The reaction time is usually from 5 minutes to 48 hours, preferably from 30 minutes to 24 hours. After the formation of the imine, the reaction solution may be used as it is to the subsequent step of the reduction reaction, or the reaction solution may be distilled or subjected to a conventional separation means to isolate the imine compound, which is then subjected to the subsequent reduction.

The reduction can be carried out by using a metal hydride complex such as sodium borohydride, sodium cyanoborohydride or lithium aluminum hydride, or by catalytic reduction employing a palladium-carbon catalyst or a Raney nickel catalyst.

When a metal hydride complex is used as a reducing agent, the reducing agent is used usually in an amount of 1 mol or an excess molar amount, preferably from 1 to 5 mols, per mol of the above imine.

For the reduction, an inert solvent, for example, an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene; or a mixture of such solvents, can be used appropriately as a solvent depending upon the type of the reducing agent.

The reaction temperature is usually from 0° C. to room temperature, and the reaction time is usually from 1 hour to 6 hours.

Further, in this process, it is also possible to react an alkylating agent of the formula 5 to the nitrile or carboxylic acid derivative of the formula 1 to preliminarily produce an alkyl compound and then to react an alkyl lithium of the formula 2 or an alkyl Grignard reagent (or an alkyl Gilman reagent) of the formula 3 to the alkyl compound to obtain a compound of the formula 6. Such a reaction can be conducted under the conditions similar to the above Process A. Accordingly, the reaction conditions described for the above Process A may all be used as the reaction conditions for this reaction.

The compounds of the formulas 1, 2, 3, 5 and 7 may be commercially available or can be produced by a proper combination, as the case requires, of the methods disclosed in Reference Examples, or conventional methods or methods similar thereto.

Process B

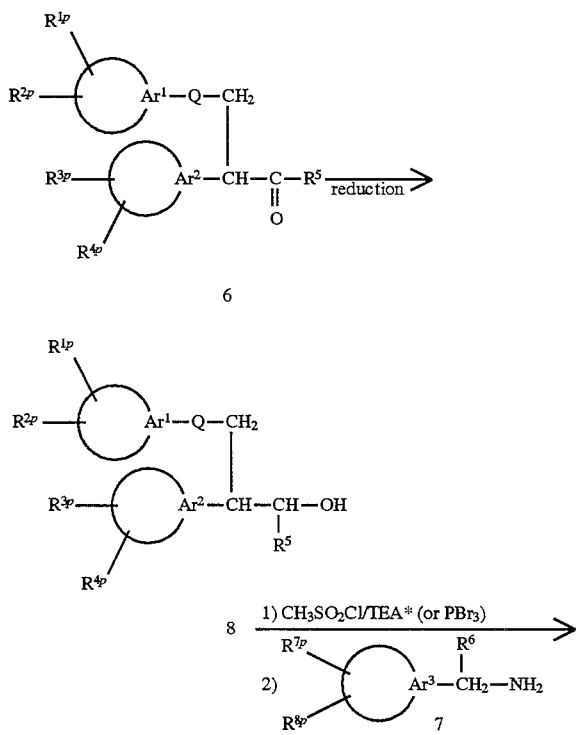

-continued

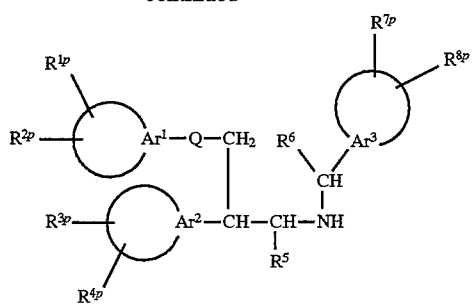

*triethylamine

In the above formulas,

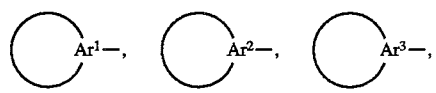

Q, $R^{1p}$, $R^{2p}$, $R^{3p}$, $R^{4p}$, $R^5$, $R^6$, $R^{7p}$ and $R^{8p}$ are as defined above.

According to this process, the desired compound (II) can be prepared by reacting a reducing agent such as a metal hydride complex to a compound of the formula 6 to obtain an alcohol compound 8 and reacting an amine compound of the formula 7 to the alcohol compound 8.

The above reaction steps will be described in detail referring to suitable reaction conditions, etc.

The reaction for reducing the compound of the formula 6 to the alcohol compound 8 can be conducted usually by using a metal hydride complex such as sodium borohydride, diisobutyl aluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the starting material compound 6.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutyl aluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction temperature and the reaction time vary depending upon the stability and the susceptibility to the reduction reaction of the starting material ketone compound 6, the type of the reducing agent and the type of the solvent. However, the reaction temperature is usually from $-80°$ C. to $100°$ C. preferably from $-70°$ C. to $40°$ C. and the reaction time is usually from 5 minutes to 2 days, preferably from 30 minutes to 24 hours.

The step of preparing the desired compound (II) from a compound of the formula 8 can be carried out by reacting a sulfonating agent such as methanesulfonyl chloride to the alcohol compound of the formula 8 in the presence of a base, or reacting a halogenating agent such as thionyl chloride or phosphorus tribromide thereto, to convert the hydroxyl group in the formula to a leaving group, followed by reacting an amine compound of the formula 7.

The reaction for introducing the leaving group can be conducted usually by reacting 1 mol or an excess molar amount, preferably from 1 to 2 mols, of a sulfonating agent and a base such as triethylamine to 1 mol of the alcohol compound 8 in an inert solvent such as methylene chloride, from $-20°$ C. to $80°$ C. and the reaction time is usually from 5 minutes to 48 hours, preferably from 30 minutes to 24 hours.

Then, the step of reacting an amine compound 7 to the compound having the leaving group introduced, obtained by the above reaction, can be conducted usually by employing 1 mol or an excess molar amount, preferably from 1 to 50 mols, of the amine compound 7 per mol of the starting compound having the leaving group, in an inert solvent such as methylene chloride, chloroform, benzene, ethyl ether or tetrahydrofuran.

If necessary, this reaction can be conducted in the presence of a base other than the amine compound of the formula 7.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from $-50°$ C. to $150°$ C., preferably from $-20°$ C. to $100°$ C., and the reaction time is usually from 5 minutes to 7 days, preferably from 10 minutes to 24 hours.

Process C

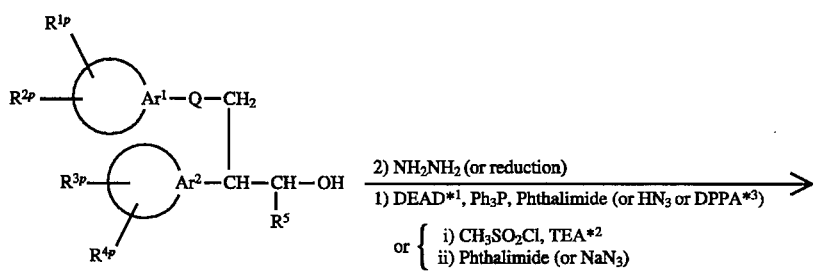

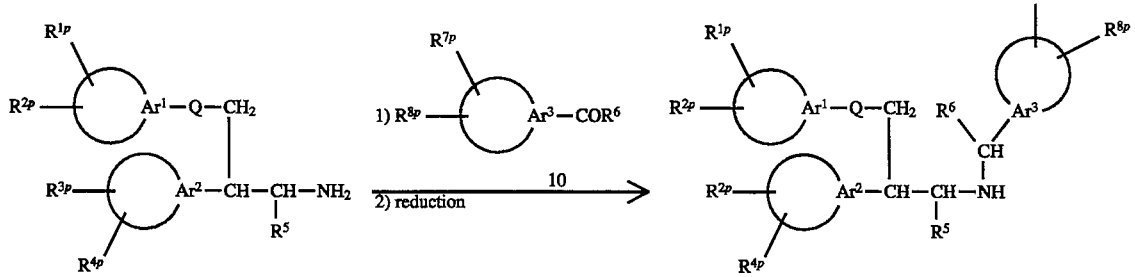

*¹diethyl azodicarboxylate
*²triethylamine
*³diphenylphosphoryl azide chloroform, benzene, tetrahydrofuran or ethyl acetate, or using 1 mol or an excess molar amount, preferably from 1 to 5 mols, of a halogenating agent.

The reaction temperature is usually from $-70°$ C. to the boiling point of the solvent used for the reaction, preferably In the above formulas,

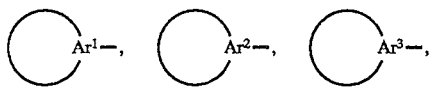

Q, $R^{1p}$, $R^{2p}$, $R^{3p}$, $R^{4p}$, $R^5$, $R^6$, $R^{7p}$ and $R^{8p}$ are as defined above.

According to this process, the desired compound (II) can be prepared by firstly reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, then reacting phthalimide (or sodium azide) in the presence of a base, to the alcohol compound of the formula 8, to obtain a phthalimide-protected form (or an azide compound) of the amine compound 9, then reacting hydrazine (or a reducing agent) to remove the phthalimide group (or reduce the azide group) to obtain an amine product of the formula 9, and finally reacting a compound of the formula 10 to the compound 9, followed by reduction.

The above reaction steps will be described in detail referring to suitable reaction conditions, etc.

For the step of producing the amine compound of the formula 9 from the alcohol compound 8, various synthetic methods and reaction conditions well known in organic synthetic chemistry for converting alcohol compounds to amines, may be employed. For example, it is preferred to employ a Mitsunobu reaction using diethyl azodicarboxylate, triphenylphosphine and phthalimide (or hydrogen azide or diphenylphosphoryl azide) or a method which comprises sulfonylation with a sulfonylation agent such as methanesulfonyl chloride in the presence of a base such as triethylamine, then reacting phthalimide (or sodium azide) in the presence of a base, and then treating the obtained phthalimide compound with hydrazine (or reducing the azide compound).

The above reactions are conducted usually in a solvent inert to the reaction. The inert solvent may, for example, preferably be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of the sulfonylation followed by the reaction with phthalimide (or sodium azide); an alcohol such as methanol or ethanol in the next step of the phthalimide-removing reaction with hydrazine; an ether such as ethyl ether or tetrahydrofuran in the case where a metal hydride complex is used as the reducing agent in the reduction reaction of the azide compound; water-containing tetrahydrofuran in the case where phosphine reduction is conducted with triphenylphosphine or the like; and an alcohol such as methanol or ethanol in the reduction by catalytic reduction.

With respect to the amounts of the reagents to be used, in the above Mitsunobu reaction, each of diethyl azodicarboxylate, triphenylphosphine and phthalimide (or hydrogen azide or diphenylphosphoryl azide) is used in an amount of 1 mol or an excess molar amount, preferably from 1 to 5 mols, per mol of the starting material alcohol compound 8. In the reaction with the phthalimide (or sodium azide) after the sulfonylation, the sulfonylation agent such as methanesulfonyl chloride is used in an amount of 1 mol or an excess molar amount, preferably from 1 to 2 mols, per mol of the alcohol compound 8, and the base such as triethylamine used at that time is usually in an amount of 1 mol or an excess molar amount, preferably from 1 to 2 mols, per mol of the sulfonylation agent. In the next step of the reaction with phthalimide (or sodium azide) in the presence of a base, 1 mol or an excess molar amount, preferably from 1 to 5 mols of each of phthalimide and the base (or sodium azide) is used per mol of the starting material sulfonylation agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimide group with hydrazine, hydrazine is used in an amount of 1 mol or an excess molar amount, preferably from 1 to 10 mols, per mol of the phthalimide compound as the starting material compound. In the reduction of the azide compound with a metal hydride complex or with triphenylphosphine, the reducing agent is used usually in an amount of 1 mol or an excess molar amount, preferably from 1 to 2 mols, per mol of the azide compound.

In the case of the above Mitsunobu reaction, the reaction temperature is usually from −70° C. to 100° C., preferably from −20° C. to 50° C., and the reaction time is usually from 5 minutes to 48 hours, preferably from 30 minutes to 24 hours. In the reaction for removing the phthalimide group by hydrazine, the reaction temperature is usually from 0° C. to the boiling point of the solvent used for the reaction, preferably from room temperature to 100° C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from −70° C. to 150° C. preferably from −20° C. to 50° C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from 30° C. to 100° C. and the reaction time is usually from 10 minutes to 48 hours, preferably from 30 minutes to 24 hours. Further, in the case of the reduction by catalytic reduction, the reaction temperature is usually from 0° C. to 100° C., preferably from room temperature to 50° C. and the reaction time is usually from 10 minutes to 48 hours, preferably from 10 minutes to 24 hours.

The step for producing the desired compound (II) from the compound of the formula 9 is carried out usually by preliminarily forming an imine by reacting 1 mol or an excess molar amount, preferably from 1 to 2 mols of the compound of the formula 10 to 1 mol of the compound of the formula 9 in an inert solvent such as methanol, ethanol, benzene, ethyl ether or tetrahydrofuran, and then reducing it.

This step can be carried out in the same manner as the step for producing the desired compound (II) from the compound of the formula 6 in the above process A. Accordingly, with respect to the reaction conditions, etc., similar modes may be employed.

Further, the compound of the formula 10 may be commercially available or can be produced by a proper combination, as the case requires, of the methods disclosed in Reference Examples, or conventional methods or methods similar thereto.
Process D
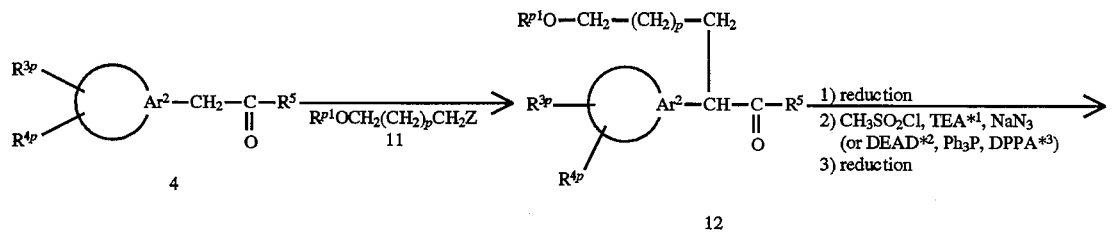
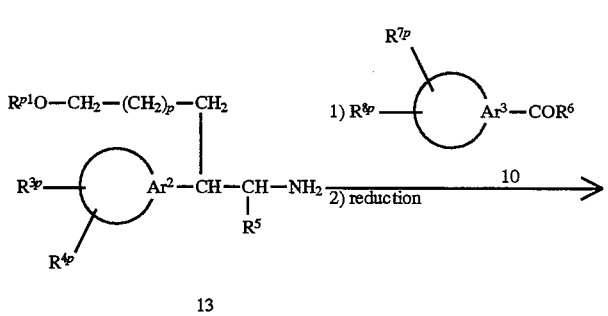
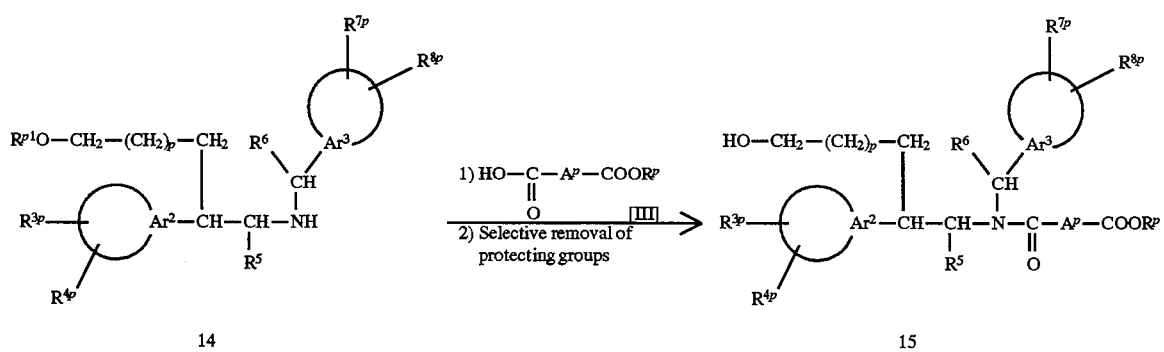
*[1] triethylamine
*[2] diethyl azodicarboxylate
*[3] diphenylphosphoryl azide
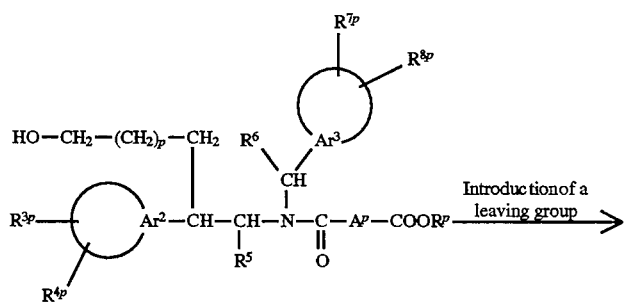

-continued

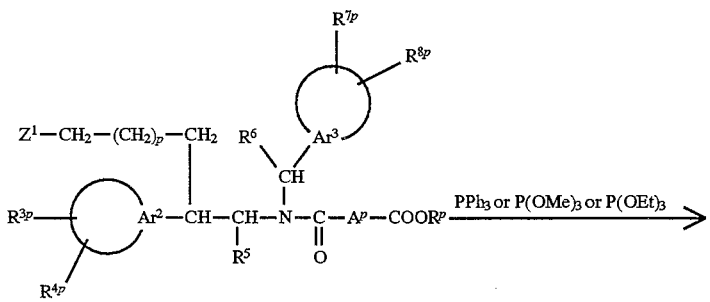

16

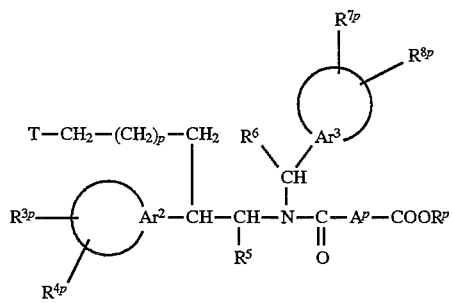

[VI]

In the above formulas, $R^{1p}$ means a hydroxyl-protecting group; and

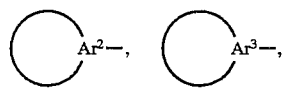

$A^p$, p, T, Z, $Z^1$, $R^{3p}$, $R^{4p}$, $R^5$, $R^6$, $R^{7p}$, $R^{8p}$ and $R^p$ are as defined above.

According to this process, the desired compound (VI) can be prepared by firstly reacting an alkylating agent of the formula 11 to a ketone compound of the formula 4 to obtain a compound of the formula 12, reacting a reducing agent such as a metal hydride complex to the compound 12 to obtain an alcohol compound, then reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, and then reacting phthalimide (or sodium azide) in the presence of a base, to obtain a phthalimide-protected form (or an azide compound) of the amine compound 13, then reacting hydrazine (or a reducing agent) to remove the phthalimide group (or reduce the azide group) to obtain an amine compound of the formula 13, reacting a compound of the formula 10 to the compound 13, followed by reduction to obtain a compound of the formula 14, reacting a carboxylic acid of the formula (III) or its reactive derivative to the compound 14, then selectively removing the protecting group represented by $R^{p1}$ to obtain a compound of the formula 15, then introducing a leaving group to the compound 15 to obtain a compound of the 16, and finally reacting triphenylphosphine, trimethyl phosphite or triethyl phosphite to the compound 16.

The hydroxyl-protecting group of $R^{p1}$ may be the hydroxyl-protecting groups mentioned above with respect to process 1.

The step of producing a compound of the formula 12 from a ketone compound of the formula 4, can be carried out in the same manner as the step of producing the compound of the formula 6 from the ketone of the formula 4 in the above process A. Accordingly, with respect to the reaction conditions, etc., similar conditions may be employed.

In the step of producing the amine compound of the formula 13 after reacting a reducing agent such as a metal hydride complex to the compound of the formula 12 to obtain an alcohol compound, the step of converting the compound of the formula 12 to the alcohol compound can be carried out in the same manner as the step of reducing the compound of the formula 6 to the alcohol compound 8 in the above process B. Accordingly, with respect to the reaction conditions, etc., similar conditions may be employed. Further, the step of producing an amine compound of the formula 13 from the obtained alcohol, can be carried out in the same manner as in the step of producing the amine compound 9 from the alcohol compound of the formula 8 in the above process C. Accordingly, with respect to the reaction conditions, etc., similar conditions may be employed.

The step of producing a compound of the formula 14 from the amine compound of the formula 13, can be carried out in the same manner as in the step of producing a compound of the formula (II) from the amine of the formula 9 in the above process C. Accordingly, with respect to the reaction conditions, etc., similar conditions may be employed.

In the step of producing a compound of the formula 15 from the compound of the formula 14, the reaction of the compound of the formula 14 with the carboxylic acid of the formula (III) or its reactive derivative, can be carried out in the same manner as the reaction of the compound of the formula (II) with the carboxylic acid of the formula (III) or its reactive derivative in the above process 1. Accordingly, with respect to the reaction conditions, etc., similar conditions may be employed.

For the step of selectively removing the protective group represented by $R^{p1}$ from the compound obtained by the above reaction, various methods may suitably be selected depending upon the type and the characteristics of the protecting group. Namely, utilizing the difference in the stability against an acid, a base or reduction between $R^{p1}$ and other protecting groups, the protecting group can selectively be removed by a conventional means such as an acid, a base or reduction. With respect to specific conditions for such a reaction, the methods disclosed in known literatures, such as "Protective Groups in Organic Synthesis, T. W. Greene, John Siley & Sons (1981)", may, for example, be used.

The step of producing a compound of the formula 16 by introducing a leaving group to the compound of the formula 15 can be carried out in the same manner as in the method of introducing a leaving group to the compound of the formula 8 in the above process B by using, for example, a halogenating agent such as thionyl chloride, phosphorus trichloride, phosphorus pentachloride, phosphorus oxychloride, phosphorus tribromide, oxalyl chloride or phosgene, or a sulfonating agent such as methanesulfonyl chloride, p-toluenesulfonyl chloride or benzenesulfonyl chloride. Accordingly, with respect to the reaction conditions, etc., similar conditions may be employed.

The step of producing the desired compound (VI) from the compound of the formula 16, can be carried out by reacting triphenylphosphine, trimethyl phosphite or triethyl phosphite, to the compound of the formula 16.

When a triphenylphosphine is reacted, the above reaction is carried out usually in an inert solvent which does not affect the reaction. As such an inert solvent, toluene or xylene is, for example, preferred.

The triphenylphosphine is used usually in an amount of 1 mol or an excess molar amount, preferably from 1 to 5 mols, per mol of the compound 16.

The reaction temperature is usually from room temperature to the boiling point of the solvent used for the reaction, preferably from 80° C. to 150° C. The reaction time is usually from 5 minutes to 7 days, preferably from 1 hour to 24 hours.

Likewise, when trimethyl phosphite or triethyl phosphite is reacted to the compound 16, the above reaction is conducted usually in an inert solvent which does not affect the reaction, or more preferably, an excess trimethyl phosphite or triethyl phosphite is used as both the solvent and the reactant.

The reaction temperature is usually from room temperature to the boiling point of the solvent for the reaction, preferably from 80° C. to 150° C., and the reaction time is usually from 5 minutes to 7 days, preferably from 1 hour to 24 hours.

Further, the compound of the formula 11 may be commercially available, or may be produced by a proper combination, as the case requires, of the methods disclosed in Reference Examples, or conventional methods or methods similar thereto.

Process E

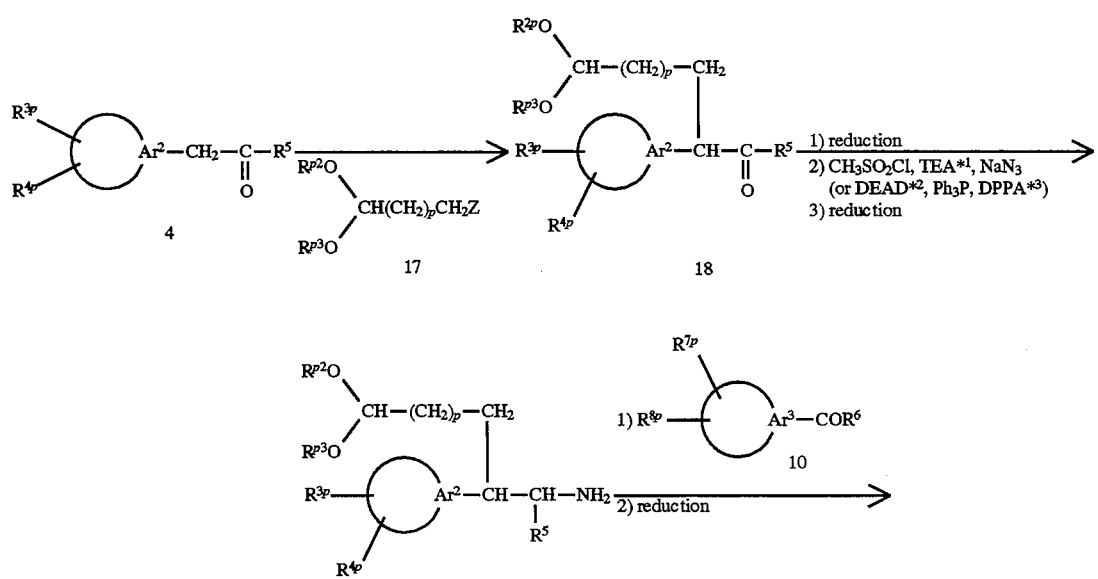

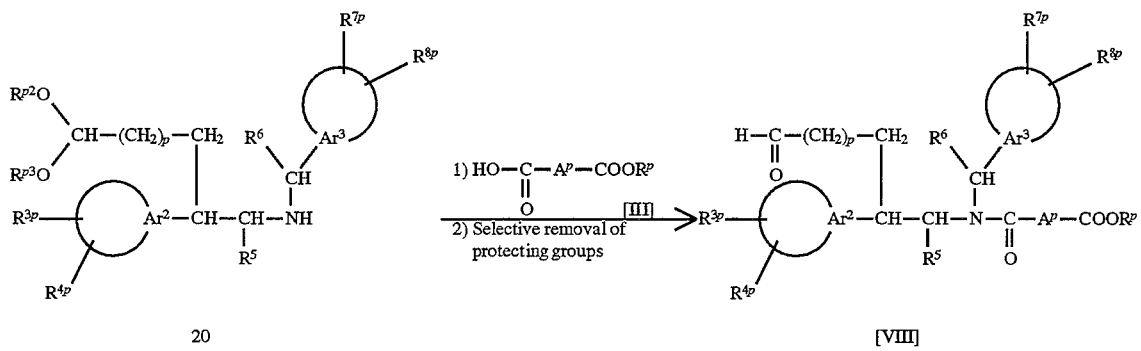

*1 triethylamine
*2 diethyl azodicarboxylate
*3 diphenylphosphoryl azide

In the above formulas, each of $R^{p2}$ and $R^{p3}$ which are the same or different, is a methyl group or an ethyl group, or $R^{p2}$ and $R^{p3}$ together represent an ethylene group; and

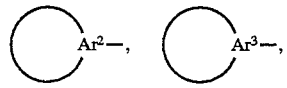

$A^p$, p, Z, $R^{3p}$, $R^{4p}$, $R^5$, $R^6$, $R^{7p}$, $R^{8p}$ and $R^p$ are as defined above.

According to this process, the desired compound (VIII) can be prepared by firstly reacting an alkylating agent of the formula 17 to a ketone compound of the formula 4 to obtain a compound of the formula 18, reacting a reducing agent such as a metal hydride complex to the compound 18 to obtain an alcohol compound, then reacting diethyl azodicarboxylate, triphenylphosphine and phthalimide (or hydrogen azide or diphenylphosphoryl azide), or reacting a sulfonylation agent such as methanesulfonyl chloride in the presence of a base such as triethylamine and then reacting phthalimide (or sodium azide) in the presence of a base, to obtain a phthalimide-protected form (or an azide compound) of the amine compound 19, then reacting hydrazine (or a reducing agent) to remove the phthalimide group (or reduce the azide group) to obtain an amine compound of the formula 19, reacting a compound of the formula 10 to the compound 19, followed by reduction to obtain a compound of the formula 20, reacting a carboxylic acid of the formula (III) or its reactive derivative to the compound 20, and then selectively removing the protecting groups represented by $R^{p2}$ and $R^{p3}$.

Removal of such protecting groups is usually preferably conducted in the presence of an acid such as hydrochloric acid, sulfuric acid or p-toluenesulfonic acid in a solvent such as water-containing methanol, water-containing ethanol or water-containing tetrahydrofuran.

The reaction temperature is usually from −20° C. to 100° C., preferably from 0° C. to 50° C., and the reaction time is usually from 5 minutes to 48 hours, preferably from 10 minutes to 24 hours.

The respective steps up to the production of the desired compound (VIII) from the ketone compound of the formula 4 can be carried out in the same manner as the respective steps for the production of the compound of the formula 15 from the ketone compound of the formula 4 in the above process D. Accordingly, with respect to the reaction conditions, etc., the same conditions as in the corresponding respective steps can be employed.

Further, the compound of the formula 17 may be commercially available, or can be produced by a proper combination, as the case requires, of the methods disclosed in Reference Examples, or conventional methods or methods similar thereto.

Process F

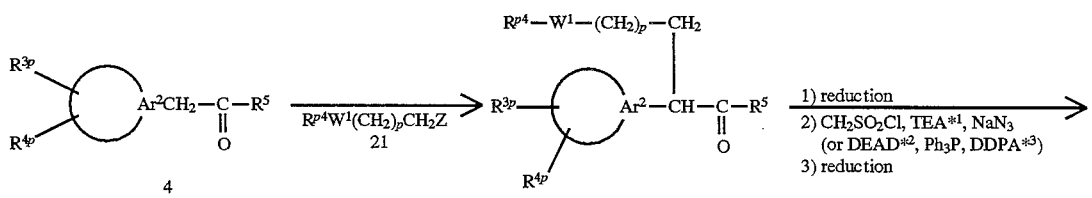

-continued

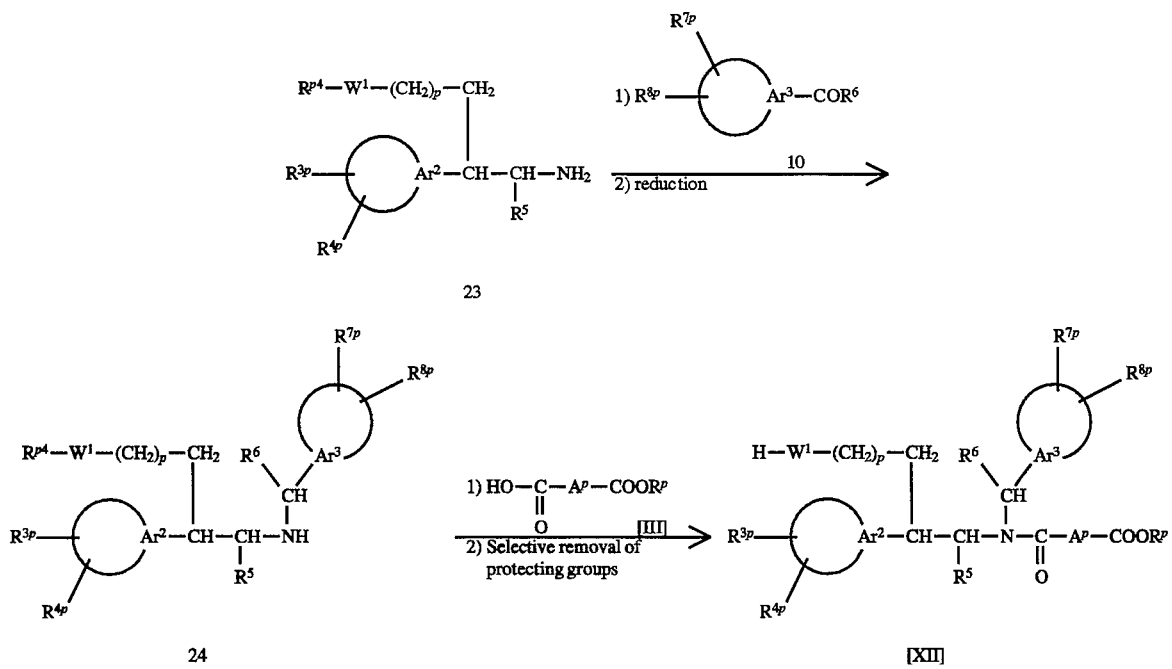

*¹triethylamine
*²diethyl azodicarboxylate
*³diphenylphosphoryl azide

In the above formulas, $R^{p4}$ represents a hydroxyl-protecting group when $W^1$ is an oxygen atom; or a mercapto-protecting group when $W^1$ is a sulfur atom; and

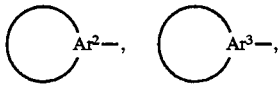

$A^p$, p, $W^1$, z, $R^{3p}$, $R^{4p}$, $R^5$, $R^6$, $R^{7p}$, $R^{8p}$ and $R^p$ are as defined above.

According to this process, the desired compound (XII) can be prepared by firstly reacting an alkylating agent of the formula 21 to a ketone compound of the formula 4 to obtain a compound of the formula 22, reacting a reducing agent such as a metal hydride complex to the compound 22 to obtain an alcohol compound, then reacting diethyl azodicarboxylate, triphenylphosphine and phthalimide (or hydrogen azide or diphenylphosphoryl azide), or reacting a sulfonylation agent such as methanesulfonyl chloride in the presence of a base such as triethylamine and then reacting phthalimide (or sodium azide) in the presence of a base, to obtain a phthalimide-protected form (or an azide compound) of the amine compound 23, then reacting hydrazine (or a reducing agent) to remove the phthalimide group (or reduce the azide group) to obtain an amine of the formula 23, reacting a compound of the formula 10 to the compound 23, followed by reduction to obtain a compound of the formula 24, reacting a carboxylic acid of the formula (III) or its reactive derivative to the compound 24, and then selectively removing the protecting group represented by $R^{p4}$.

When $R^{p4}$ is a hydroxyl-protecting group, as such a hydroxyl-protecting group, the hydroxyl-protecting groups disclosed above with respect to process 1 may be employed.

When $R^{p4}$ is a mercapto-protecting group, as such a mercapto-protecting group, the hydroxyl-protecting groups disclosed above with respect to process 1 can be employed.

The respective steps up to the production of the desired compound (XII) from the ketone compound of the formula 4 can be carried out in the same manner as the respective steps for the production of the compound of the formula 15 from the ketone compound of the formula 4 in the above process D. Accordingly, with respect to the reaction conditions, etc., the same conditions as in the corresponding respective steps can be employed.

Further, the compound of the formula 21 may be commercially available, or can be produced by a proper combination, as the case requires, of the methods disclosed in Reference Examples, or conventional methods or methods similar thereto.

Process G $$HO-(CH_2)_p-CH_2-\underset{\underset{R^5}{|}}{\overset{\overset{R^6}{|}}{Ar^2-CH-CH-N}}-\underset{\overset{\|}{O}}{C}-A^p-COOR^p \quad \text{[XII-a]}$$

(with Ar³ ring bearing R⁷ᵖ, R⁸ᵖ)

Introduction of a leaving group →

$$Z^1-(CH_2)_p-CH_2-\underset{\underset{R^5}{|}}{\overset{\overset{R^6}{|}}{Ar^2-CH-CH-N}}-\underset{\overset{\|}{O}}{C}-A^p-COOR^p \quad \text{[X]}$$

In the above formulas,

Ar²—, Ar³—, $A^p$, p, $Z^1$, $R^{3p}$, $R^{4p}$, $R^5$, $R^6$, $R^{7p}$, $R^{8p}$ and $R^p$ are as defined above.

According to this process, the desired compound (X) can be prepared by introducing a leaving group to the compound of the formula (XII-a).

This step can be carried out in the same manner as the method of introducing a leaving group to the compound of the formula 15 in the above process D. Accordingly, with respect to the reaction conditions, etc., similar conditions may be employed.

A compound of the formula (VII):

$$Ar^1-(CH_2)_n-CH_2-T \quad \text{(VII)}$$

(bearing $R^{1p}$, $R^{2p}$)

wherein

Ar¹—, n, T, $R^{1p}$ and $R^{2p}$ are as defined above, can be prepared from a compound of the formula (XIII):

$$Ar^1-(CH_2)_n-CH_2-Z^1 \quad \text{(XIII)}$$

(bearing $R^{1p}$, $R^{2p}$)

wherein

Ar¹—, n, $Z^1$, $R^{1p}$ and $R^{2p}$ are as defined above, in accordance with the method for producing a compound of the formula (VI) from the compound of the formula 16 in process D.

Further, the compound of the formula (XIII) may be commercially available, or can be prepared by a proper combination, as the case requires, of the methods disclosed in Reference Examples, or conventional methods or methods similar thereto.

Process H $$R^aCH_2-COOR^b + \underset{26}{\underset{HC}{\overset{R^c}{\underset{\|}{C}}\underset{COOR^e}{\diagdown}}{\overset{COOR^d}{\diagup}}} \xrightarrow{\text{base}}$$

25

$$R^b-OOC-\underset{}{\overset{R^a}{\underset{|}{CH}}}-\underset{\underset{COOR^e}{|}}{CH}-\overset{R^c}{\underset{|}{CH}}-COOR^d \xrightarrow{\text{deprotection}}$$

27

$$HOOC-\overset{R^a}{\underset{|}{CH}}-\underset{\underset{COOR^e}{|}}{CH}-\overset{R^c}{\underset{|}{CH}}-COOR^d \quad \text{[III-a]}$$

In the above formulas, each of $R^a$ and $R^c$ which are the same or different, is a hydrogen atom, a lower alkyl group, an aryl group or an aralkyl group; each of $R^d$ and $R^e$ which are the same or different, is a carboxyl-protecting group; and $R^b$ is a tert-butyl group, a benzyl group, a benzhydryl group or a trityl group.

Process H is a process for preparing a carboxylic acid derivative of the formula (III-a) among the compounds of the above formula (III).

According to this process, the desired carboxylic acid derivative (III-a) can be prepared by conducting a so-called Michael addition reaction which comprises reacting a maleic acid derivative or a fumaric acid derivative of the formula 26 to an ester derivative having a readily removable carboxyl-protecting group $R^b$, represented by the formula 25, in the presence of a base, and then removing the carboxyl-protecting group $R^b$ from the obtained Michael addition product 27 under a mild condition.

As the carboxyl-protecting group for $R^d$ and $R^e$, a lower alkyl group such as a tert-butyl group, or a benzhydryl group, is preferred.

The protecting group $R^b$ is preferably the one which can readily be removed under a mild condition of catalytic reduction or weakly acidic condition and which is stable under the Michael addition reaction condition, such as a tert-butyl group, a benzyl group, a benzhydryl group or a trityl group.

The above Michael addition reaction can be conducted by reacting the compound of the formula 26 in an amount of 1 mol or an excess molar amount, preferably from 1 to 2 mols, to 1 mol of the compound of the formula 25 in the presence of a base such as sodium hydride, butyl lithium, lithium diisopropylamide or lithium bis(trimethylsilyl)amide usually in an inert solvent such as benzene, ethyl ether or tetrahydrofuran.

Such a base is used usually in an amount of 1 mol or a slightly excess molar amount, preferably from 1 to 1.5 mols, per mol of the compound of the formula 26.

The reaction temperature is usually from −100° C. to 100° C. preferably from −80° C. to room temperature, and the reaction time is usually from 5 minutes to 24 hours, preferably from 10 minutes to 10 hours.

The reaction conditions for the reaction for removing the protecting group from the compound of the formula 27 to form the desired carboxylic acid derivative (III-a), vary depending upon the type of the protecting group, etc. For example, when the protecting group is a tert-butyl group, a benzhydryl group or a trityl group, a method may be employed wherein the compound is treated with an acid such as acetic acid, formic acid, trifluoroacetic acid or hydrochloric acid, preferably within a temperature range of from −20° C. to 50° C. for from 10 minutes to 24 hours in the absence of a solvent or usually in an inert solvent such as methylene chloride, anisole, tetrahydrofuran, methanol or ethanol or a solvent mixture thereof with water.

For example, when the protecting group is a benzyl group, a benzhydryl group or a trityl group, a method may be employed wherein the compound is catalytically reduced with a catalyst such as a palladium-carbon catalyst or a Raney nickel catalyst preferably under a hydrogen pressure of from 1 to 20 kg/cm² preferably within a temperature range of from 0° C. to 40° C. for from 10 minutes to 24 hours usually in an inert solvent such as methanol, ethanol, dioxane, water or acetic acid, or a solvent mixture thereof.

Among compounds of the formula (III-a), an optically active compound of the formula (III-1b):

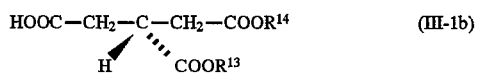 (III-1b)

or the formula (III-2b):

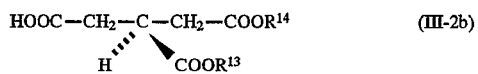 (III-2b)

wherein each of $R^{13}$ and $R^{14}$ which are the same or different, is a carboxyl-protecting group, can be obtained by reacting a racemic mixture of the compound of the formula (III-b):

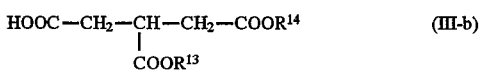 (III-b)

wherein $R^{13}$ and $R^{14}$ are as defined above, with cinchonidine or quinine to obtain a mixture of two diastereomers, then separating and collecting either one of the diastereomers by utilizing the difference in the solubility as between the two diastereomers, followed by recovering the free carboxylic acid by treating with an acid.

Separation of the diastereomer mixture may be conducted in an organic solvent such as carbon tetrachloride or isopropyl ether. Usually, the mixture of the diastereomers is dissolved in a solvent in a hot state, and the solution is gradually cooled to utilize the solubility difference for separation of the diastereomers.

Further, either one of the diastereomers thus obtained is treated with an acid such as hydrochloric acid to obtain an optically active compound of the formula (III-1b) or (III-2b).

The compounds of the formula 25 and 26 may be commercially available or can be produced by a proper combination, as the case requires, of the methods disclosed in Reference Examples, or conventional methods or methods similar thereto.

Process I

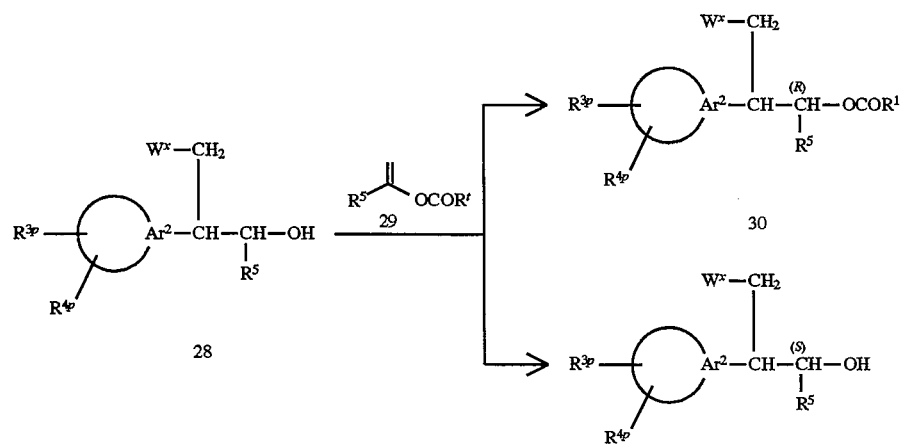

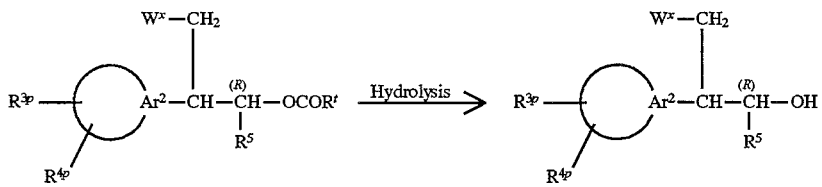

30 → 32

In the above formulas, $W^x$ is

(wherein

Q, $R^{1p}$ and $R^{2p}$ are as defined above), $R^{p4}$—$W^1$—$(CH_2)_{p'}$— (wherein p' is an integer of from 0 to 4; and $R^{p4}$ and $W^1$ are as defined above) or

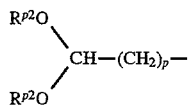

(wherein $R^{p2}$, $R^{p3}$ and p are as defined above); $R^s$ is a hydrogen atom or a methyl group; $R^r$ is a lower alkyl group, an aryl group or a lower alkenyl group; and

$R^{3p}$, $R^{4p}$ and $R^5$ are as defined above.

Process I is a process for preparing an optically active substance 31 or 32 of an alcohol compound 28 obtainable as the above formula 8 or a reduction product of the formula 12, 18 or 22.

According to this process, the desired optically active alcohol compounds 31 and 32 can be prepared by reacting a vinyl ester derivative of the formula 29 to a racemic alcohol derivative of the formula 28 in the presence of a lipase, separating the obtained optically active ester derivative 30 and the optically active alcohol derivative, and then hydrolyzing the ester group with respect to the optically active ester derivative 30.

$R^r$ of the vinyl ester derivative of the formula 29 is preferably a lower alkyl group such as a methyl group or an ethyl group; an aryl group such as a phenyl group or a naphthyl group; or an aralkyl group such as a benzyl group or a 2-phenylethyl group. Particularly preferred is a methyl group, i.e. a case wherein the compound of the formula 29 is vinyl acetate or isopropenyl acetate.

The above optical resolution reaction by lipase can be conducted usually in an inert solvent such as methylene chloride, chloroform, ethyl ether, tetrahydrofuran, benzene, toluene, hexane, heptane or acetonitrile, or by using the starting material vinyl ester derivative of the formula 29 itself as the solvent.

The vinyl ester derivative 29 is used usually in an amount of 1 mol or in a large excess molar amount, preferably from 1 to 100 mols, per mol of the starting material compound 28, and the amount of the lipase as the catalyst is from 0.01 to 100%, preferably from 0.1 to 20%, by weight, relative to the compound 28.

The type of the lipase is preferably a lipase derivative from Pseudomonas sp. such as Toyothium LIP™ (manufactured by Toyobo).

Further, the above enzymatic reaction tends to be accelerated, when the reaction is carried out in the presence of a base. As a base to be used for this purpose, an organic base such as triethylamine or diisopropylethylamine, is preferred.

The base is used usually in an amount of 0.01 mol or a slightly excess molar amount, preferably from 0.1 to 1.5 mols, relative to the starting material compound 28.

The reaction temperature is usually from 0° C. to 50° C., preferably from room temperature to 40° C. The reaction time is usually from 30 minutes to 7 days, preferably from 1 hour to 48 hours.

The hydrolytic reaction of the ester of the formula 30 can be conducted by a common method well known in the organic synthetic chemistry under an acidic or basic condition.

To demonstrate the usefulness of the compounds of the present invention, 50% inhibitory concentrations ($IC_{50}$ values) of the compounds of the present invention against the protein-farnesyl transferase (PFT) activities, were obtained.

Inhibitory activities against protein-farnesyl transferase (1) Preparation of PFT PFT was separated in such a manner that a soluble fraction of rat's brain was fractionated by means of 30%–50% saturated ammonium sulfate, further dialyzed and then subjected to column chromatography by Q-cephalose™ (manufactured by Pharmacia) (Reiss et al, Cell, vol. 62, p. 81–88 (1990)).

(2) Method for measuring PFT activities

Measurement of PFT activities was conducted by using, as a prenyl acceptor, H-ras protein or a substance that biotin was added to N-terminal of a peptide corresponding to a 7 amino acid residue at C terminal of K-rasB protein (biotin-added Lys-Thr-Ser-Cys-Val-Ile-Met) and, as a prenyl doner, [$^3$H]-labeled farnesylpyrophosphate (FPP) (Reiss et al, Methods: A Companion to a Methods in Enzymology, vol. 1, No. 3, p. 241–245 (1990)).

The [$^3$H]-labeled farnesylpyrophosphate (22.5 Ci/mmol) was purchased from New England Nuclear Co. Non-labeled farnesylpyrophosphate was chemically synthesized from ditriethylammonium phosphate, trans-trans-farnesol and trichloroacetonitrile and purified by XAD-2-resin column and diethylaminoethylcellulose (Cornforth et al, Methods in Enzymology, vol. 15, p. 385–390 (1969)).

H-ras protein was expressed in Escherichia coli and purified (Gibbs et al, Proc. Natl. Acad. Sci., vol. 81, p. 5704–5708 (1984)).

The PFT reaction solution containing H-ras protein as the prenyl acceptor was 25 µl, and its composition was 50 mM Hepes pH7.5/50 µM $ZnCl_2$/5 mM $MGCl_2$/20 mM KCl/5mM DTT/0.6 µM all trans [$^3$H]-farnesylpyrophosphate/25 µM H-ras protein/PFT derived from rat brain (Q-sephalose fraction). The reaction temperature was 37° C., the preincubation time was 10 minutes, and the reaction time was 20 minutes.

The PFT reaction solution containing biotin-added Lys-Thr-Ser-Cys-Val-Ile-Met as the prenyl acceptor, was 25 µl, and its composition was 50 mM tris-Cl pH7.5/50 µM $ZnCl_2$/5 mM $MGCl_2$/20 mM KCl/1 mM DTT/0.2% n-octyl-β-D-glucopyranoside/0.6 µM all trans [$^3$H]-farnesylpyrophosphate/3.6 µM biotin-added Lys-Thr-Ser-Cys-Val-Ile-Met/PFT derived from rat brain (Q-sephalose fraction). The reaction temperature was 37° C., the preincubation time was 10 minutes, and the reaction time was 20 minutes.

The enzymatic reaction product containing H-ras protein as the prenyl acceptor, was analyzed by SDS-PAGE (sodium dodecylsulfate/polyacrylamide gel electrophoresis). The [$^3$H]-labeled enzymatic reaction product was boiled for 3 minutes in a buffer solution containing 2% SDS/50 mM Tris-Cl pH6.8/10% sucrose/5% 2-mercaptoethanol, then subjected to electrophoresis with a slab gel of 12% polyacrylamide, whereby the [$^3$H]-labeled H-ras protein was fluorography-enhanced by EN3HANCE™ (manufactured by New England Nuclear Co.) and then visualized by autoradiography (James et al, Science, vol. 260, No. 25, p. 1937–1942 (1993)).

The measurement of PFT activities using H-ras protein as the prenyl receptor, was also analyzed by a rapid separate method. The mixed solution for measurement wherein no prenyl doner was present, was preincubated, and a prenyl group transferring reaction was initiated by an addition of [$^3$H]-FPP and terminated at an appropriate time by an addition of 0.5 ml of 4% SDS. Further, 0.5 ml of 30% trichloroacetic acid was added thereto and thoroughly mixed. Then, the reaction solution was left to stand at 4° C. for 60 minutes to let H-ras protein precipitate. This reaction solution was subjected to filtration under reduced pressure by Whatman GF/B filter. The filter was washed 6 times with 2 ml of 6% trichloroacetic acid, and mixed with 8 ml of scintillation cocktail (Clearsol I™, manufactured by Nacalai Tesque Co.). Then, counting was carried out by a Beckmann TRI-CARB2500TR scintillation counter.

Measurement of PFT activities was also carried out by using biotin-added Lys-Thr-Ser-Cys-Val-Ile-Met as the prenyl acceptor. The mixed solution for measurement containing biotin-added Lys-Thr-Ser-Cys-Val-Ile-Met as the prenyl acceptor and containing no prenyl doner, was preliminarily thermally equilibrated, and then a prenyl group transferring reaction was initiated by an addition of [$^3$H]-FPP and terminated at an appropriate time by an addition of 0.2 ml of 2 mg/ml bovine serum albumin/2% sodium dodecylsulfate/150 mM NaCl. Further, 0.02 ml of avidin agarose (Pierce) was added thereto, and the mixture was shaked for 30 minutes to let the [$^3$H]-farnesyl group-transferred biotin-added Lys-Thr-Ser-Cys-Val-Ile-Met sufficiently bond to the avidin agarose. Then, avidin agarose was washed four times with 1 ml of 2 mg/ml bovin serum albumin (BSA)/4% sodium dodecylsulfate/150 mM NaCl, and mixed with 1 ml of scintillation cocktail (Clearsol I™, manufactured by Nacalai Tesque). Then, counting was carried out by a Beckmann TRI-CARB2500TR scintillation counter.

The biotin-added Lys-Thr-Ser-Cys-Val-Ile-Met heptapeptide used as an artificial substrate, was synthesized in a solid phase by an Applied biosystems model 431A peptide synthesizer, and an α-amino terminal of the solid phase Lys-Thr-Ser-Cys-Val-Ile-Met heptapeptide which was bound to a resin, was biotin-modified by N-hydroxysuccinimide biotin, then cut off from the resin and purified by reversed phase high performance liquid chromatography (HPLC).

The addition of the compound of the present invention to the PFT reaction system was carried out by preliminarily adding dimethyl sulfoxide in an amount of 1% by volume (0.25 µl) of the reaction solution.

The 50% inhibitory concentrations ($IC_{50}$ values) of the compounds of the present invention against PFT activities, were obtained, and the results are shown in the following Table.

TABLE 1

| 50% inhibitory concentrations against PFT activities | |
|---|---|
| Compound | $IC_{50}$ (nM) |
| Example 34 | 0.53 |
| Example 45 | 0.15 |
| Example 59 | 0.46 |

PHARMACOLOGICAL TEST EXAMPLE 2

(Inhibitory activities against farnesyl-modification of Ras protein)

Using the compounds of the present invention, inhibitory activities against farnesyl-modification of Ras protein in NIH3T3 cells transformed by activated ras gene, were measured.

The NIH3T3 cells transformed by activated ras gene, were seeded on a culture plate and cultured for 3 days. Then, a compound of the preset invention in a predetermined concentration was added to the culture. In accordance with the method disclosed in J. Biol. Chem., vol. 268, p. 18415 (1993), the cells were cultured for 24 hours and then taken off from the plate, and the cells were dissolved. After centrifugal separation for 5 minutes under 12000 g, the supernatant was used as a cell extract. The cell extract was subjected to SDS polyacrylamide gel electrophoresis to separate farnesyl-modified Ras protein and non-farnesyl-modified Ras protein. The protein on the gel was transferred onto a nitrocellulose membrane, and an anti-Ras protein antibody was reacted as a probe (primary antibody reaction). An anti-primary antibody, a peroxidase inclusion (secondary antibody), was reacted, and then Ras protein was detected by a chemical fluorescence enhancing kit. The proportion of non-farnesyl-modified Ras protein was quantified by a densitometer and taken as the inhibitory activity.

The 50% inhibitory concentrations ($IC_{50}$ values) of the compounds of the present invention against farnesyl-modification of Ras protein are shown in Table 2.

TABLE 2

| | 50% inhibitory concentrations against farnesyl-modification of Ras protein |
|---|---|
| Compound | IC$_{50}$ (µ/M) |
| Example 45 | 7.7 |
| Example 46 | 18 |
| Example 69 | 4.5 |

PHARMACOLOGICAL TEST EXAMPLE 3

(Antitumor effects to transformed cells (NIH/ras) using active type human Ha-ras)

The compound of the present invention exhibits excellent antitumor effects, as shown by the following Pharmacological Test Example.

The antitumor effects of the compound of the present invention against NIH/ras cells are shown in Table 3.

TABLE 3

Antitumor effects of the compound of the present invention against NIH/ras

| Tumor [1] | Compound | Dose [2] Intra-peritoneal (mg/kg/injection) | Weight of tumor [3] Average (g) ± standard deviation | Growth inhibition [4] (%) |
|---|---|---|---|---|
| NIH/ras | Example 69 | 0 | 0.22 ± 0.07 | 0 |
| | | 10 | 0.17 ± 0.09 | 23 |
| | | 30 | 0.09 ± 0.05** | 59 |

[1] Tumor inoculation: 10$^6$ cells were transplanted subcutaneously to a nude mouse.
[2] Dose: Each dose was intra-peritonealy administered once a day from the first day to the sixth day after the inoculation of the cells.
[3] Weight of tumor: On the seventh day after inoculation of the cells, the tumors were weighed.
[4] Growth inhibition: (1-(average weight of tumor of the treated group/average weight of tumor of the control group)) × 100
*and **: Statistical analysis by t-test are 5% and 1%, respectively.

From the forgoing results, the compounds of the present invention have excellent inhibitory activities against protein-farnesyl transferase (PFT) and thus useful as antitumor agents, for example, against colon cancers, pancreatic cancers, myloid leukemias, lung cancer, carcinoma cutaneum or thyroid gland cancer, particularly against pancreatic cancers.

The compound of the formula (I) of the present invention can be orally or parenterally administered, and it may be formulated into a formulation suitable for such administration, so that it can be used as an antitumor agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount.

These formulations may further contain therapeutically effective other compounds.

When the compound of the present invention is used as an antitumor agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.002 to 10 mg/kg per day for an adult all at once or in a few times in a divided fashion.

EXAMPLES and REFERENCE EXAMPLES

Now, the present invention will be described in further detail with reference Examples and Reference Examples. However, the present invention is by no means restricted by such Examples.

Example 1

Preparation of N-{(1RS,2RS,4E)-2-(4-chlorophenyl)-1-methyl-5-(2-naphthyl)-4-pentenyl)-N-(2-naphthylmethyl)carbamoylmethylsuccinic acid 237 mg of N-((1RS,2RS,4E)-2-(4-chlorophenyl)-1-methyl-5-(2-naphthyl)-4-pentenyl}-2-naphthylmethylamine obtained in Reference Example 1 was dissolved in 2 ml of methylene chloride, and 105 mg of chloroformylmethylsuccinic anhydride and 83 µl of triethylamine were added thereto, followed by stirring at room temperature for one hour. The reaction solution was evaporated to dryness under reduced pressure, and then, the residue was dissolved in 3 ml of tetrahydrofuran. 3 ml of a 1N sodium hydroxide aqueous solution was added thereto, followed by stirring at room temperature for one hour. The reaction solution was acidified by an addition of 4 ml of 1N hydrochloric acid, and then extracted by an addition of ethyl acetate. The organic layer was washed with a saturated sodium chloride aqueous solution and then dried over anhydrous magnesium sulfate. The drying agent was filtered off, and then the solvent was distilled off under reduced pressure. The residue was purified by silica gel column chromatography (chloroform/methanol=50/1) and then treated with a mixed solution of methylene chloride and hexane to obtain 235 mg (yield: 74%) of the above identified compound as white powder.

$^1$H-NMR(CDCl$_3$+CD$_3$OD)δ:0.93 and 1.00(total 3H, each d, J=5.1Hz and 6.5Hz), 2.25–3.53(8H, m), 4.48–4.95(3H, m), 5.30–5.62, 5.64–5.77, 5.85–6.00, 6.29–6.40(total 2H, each m), 6.92–7.98(18H, m)

FAB-MS:634(M+H)

Compounds of Examples 2 to 21 were prepared in the same manner as in Example 1 except that instead of N-{(1RS,2RS,4E)-2-(4-chlorophenyl)-1-methyl-5-(2-naphthyl)-4-pentenyl}-2-naphthylmethylamine used as the starting material in the above reaction, the corresponding amine derivatives were employed.

Example 2

N-{(1RS,2RS,4E)-2-(4-chlorophenyl)-1-methyl-5-(1-naphthyl)-4-pentenyl}-N-(2-naphthylmethyl)-carbamoylmethylsuccinic acid $^1$H-NMR(CDCl$_3$+CD$_3$OD)δ:0.95 and 1.00(total 3H, each d, J=6.1Hz and 6.3Hz), 2.32–3.54(8H, m), 4.26–4.93(3H, m), 5.30–5.44, 5.70–5.82(total 1H, each m), 6.51 and 6.82 (total 1H, each dd, J=6.6Hz, 15.0Hz and 3.9Hz, 10.4Hz), 6.91–7.88(18H, m)

FAB-MS:634(M+H)

Example 3

N-{(1RS,2RS)-2-(4-chlorophenyl)-1-methyl-5-(2-naphthyl)pentyl}-N-(2-naphthylmethyl)carbamoylmethyl-succinic acid $^1$H-NMR(CDCl$_3$+CD$_3$OD)δ:0.80–0.85, 0.92(total 3H, m and d, J=6.6Hz), 1.08–1.74(4H, m), 2.27–3.47 (8H, m), 4.11–5.35 (3H, m), 6.83–7.86(18H, m)

FAB-MS:634(M–H)

Example 4

N-{(1RS,2RS)-2-(4-chlorophenyl)-1-methyl-4-(2-naphthoxy)butyl}-N-(2-naphthylmethyl) carbamoylmethyl-succinic acid $^1$H-NMR(CDCl$_3$+CD$_3$OD)δ:0.80–0.95(3H, m), 1.89–3.89(8H, m), 4.58–4.93(5H, m), 6.74–7.89(18H, m)

FAB-MS:638(M+H)

Example 5

N-{(1RS,2RS)-2-(4-chlorophenyl)-1-methyl-4-(2-naphthyl)butyl)-N-(2-naphthylmethyl) carbamoylmethyl-succinic acid $^1$H-NMR(CDCl$_3$+CD$_3$OD)δ:0.72–0.84(3H, m), 1.73–3.52(10H, m), 3.95–5.30(3H, m), 6.93–7.84(18H, m)

FAB-MS:622(M+H)

Example 6

N-{(1RS,2RS)-2-(4-chlorophenyl)-1-methyl-6-(2-naphthyl)hexyl}-N-(2-naphthylmethyl) carbamoylmethyl-succinic acid $^1$H-NMR(CDCl$_3$+CD$_3$OD)δ:0.85 and 0.89(total 3H, each d, J=6.5Hz and 6.7Hz), 0.93–1.72(6H, m), 2.25–3.48(8H, m), 4.03–5.30(3H, m), 7.02–7.82(18H, m)

FAB-MS:650(M+H)

Example 7

N-{(1RS,2RS)-2-(4-chlorophenyl)-1-methyl-5-phenyl-4-pentynyl}-N-(2-naphthylmethyl) carbamoylmethylsuccinic acid $^1$H-NMR(CDCl$_3$+CD$_3$OD)δ:0.82–0.99(3H, m), 2.55–2.84(5H, m), 2.98–3.30(2H, m), 3.32–3.47(1H, m), 4.44–5.45(3H, m), 7.18–7.87(16H, m)

FAB-MS:582(M+H)

Example 8

N-{(1RS,2RS,4E)-2-(4-methoxyphenyl)-1-methyl-5-(2-naphthyl)-4-pentenyl}-N-(2-naphthylmethyl) carbamoyl-methylsuccinic acid $^1$H-NMR(CDCl$_3$+CD$_3$OD)δ:0.85–1.00(3H, m), 2.25–3.45(8H, m), 4.20–4.30, 4.40–4.60, 4.55–4.75 and 5.49–5.85(total 6H, each m), 5.90–6.05(1H, m), 6.36 and 6.38(total 1H, each d,each J=15.9Hz), 6.80–7.89(18H, m)

FAB-MS:630(M+H)

Example 9

N-{(1RS,2RS,4E)-1-methyl-2-(4-methylphenyl)-5-(2-naphthyl)-4-pentenyl}-N-(2-naphthylmethyl) carbamoyl-methylsuccinic acid $^1$H-NMR(CDCl$_3$)δ:0.85–1.00(3H, m), 2.05–3.70 and 4.15–4.87(total 11H, each m), 5.45–5.60 and 5.68–5.83(1H, each m), 5.90–6.15 and 6.30–6.44(total 1H, each m), 6.95–7.90(18H, m)

FAB-MS:614(M+H)

Example 10

N-{(1RS,2RS,4E)-1-methyl-5-(2-naphthyl)-2-(4-nitrophenyl)-4-pentenyl}-N-(2-naphthylmethyl) carbamoyl-methylsuccinic acid $^1$H-NMR(CDCl$_3$)δ:0.74–0.90 and 1.11(total 3H, m and brd, J=5.3Hz), 2.10–3.54(8H, m), 4.12–4.88(3H, m), 5.12–5.30, 5.52–5.64, 5.69–5.87 and 6.17–6.32(total 2H, each m), 6.80–8.07(18H, m)

FAB-MS:645(M+H)

Example 11

N-{(1RS,2RS,4E)-2-(4-fluorophenyl)-1-methyl-5-(2-naphthyl)-4-pentenyl}-N-(2-naphthylmethyl) carbamoyl-methylsuccinic acid $^1$H-NMR(CD$_3$OD)δ:0.85–1.01(3H, m), 2.30–3.45(8H, m), 4.30–4.50, 4.60–5.05, 5.30–5.50 and 5.50–5.70(total 3H, each m), 5.80–6.00(1H, m), 6.26(1H, d, J=15.5Hz), 6.86–7.93(18H, m)

FAB-MS:618(M+H)

Example 12

N-{(1RS,2RS,4E)-1-methyl-5-(2-naphthyl)-2-(4-trifluoromethylphenyl)-4-pentenyl}-N-(2-naphthylmethyl)carbamoylmethylsuccinic acid $^1$H-NMR(CDCl$_3$)δ:0.89 and 0.93(total 3H, each d, J=5.5Hz and 6.4Hz), 2.20–3.56(8H, m), 4.10–4.26 and 4.95–5.40(total 1H, each brs), 4.38–4.92(total 2H, m), 5.25–5.35 and 5.80–6.00(total 1H, each m), 5.69 and 6.33 (total 1H, each dd, J=10.2Hz, 15.5Hz and 11.2Hz, 15.5Hz), 6.90–7.82(18H, m)

FAB-MS:668(M+H)

Example 13

N-{(1RS,2RS,4E)-1-methyl-5-(2-naphthyl)-2-phenyl-4-pentenyl}-N-(2-naphthylmethyl) carbamoylmethylsuccinic acid $^1$H-NMR(CDCl$_3$)δ:0.92 and 0.95(total 3H, each d, J=6.1Hz and 6.9Hz), 2.22–3.60(8H, m), 4.12–4.26 and 4.90–5.40(total 1H, each brs), 4.38–4.82(2H, m), 5.45–5.60 and 5.93–6.08(total 1H, each m), 5.80 and 6.41(total 1H, each dd, J=9.3Hz, 15.5Hz and 8.3Hz, 15.4Hz), 7.09–7.83 (19H, m)

FAB-MS:600(M+H)

Example 14

N-{(1RS,2RS,4E)-1-methyl-2-(6-methyl-3-pyridyl)-5-(2-naphthyl)-4-pentenyl)-N-(2-naphthylmethyl) carbamoyl-methylsuccinic acid $^1$H-NMR(CD$_3$OD)δ:0.85–1.10(3H, m), 2.40–3.50(8H, m), 2.70(3H, s), 4.50–5.40(3H, m), 5.65–6.40(2H, m), 6.80–8.00(15H, m), 8.35–8.70(2H, m)

FAB-MS:615(M+H)

EXAMPLE 15

N-{(1RS,2RS,6E)-2-(4-chlorophenyl)-1-methyl-7-phenyl-6-heptenyl}-N-(2-naphthylmethyl) carbamoylmethylsuccinic Acid $^1$H-NMR(CDCl$_3$+CD$_3$OH)δ:0.87 and 0.90(total 3H, each d, each J=6.9 Hz), 1.02–2.20(4H, m), 2.48–3.51(8H, m), 4.06–5.35(3H, m), 5.77–6.33(2H, m), 7.07–7.81(16H, m)

FAB-MS:612(M+H)

EXAMPLE 16

N-{(1RS,2RS,6E)-2-(4-chlorophenyl)-1-methyl-7-(2-naphthyl)-6-heptenyl}-N-(2-naphthylmethyl) carbamoylmethylsuccinic Acid $^1$H-NMR(CDCl$_3$)δ:0.80–1.00(3H, m), 1.05–3.40(12H, m), 3.95–5.20(3H, m), 5.83–6.51(2H, m), 6.98–7.85(18H, m)

FAB-MS:662(M+H)

EXAMPLE 17

N-{(1RS,2RS,4E)-2-(4-chlorophenyl)-1-methyl-5-(2-naphthyl)-4-pentenyl}-N-(3-quinolylmethyl) carbamoylmethylsuccinic acid $^1$H-NMR(CDCl$_3$)δ:0.72–0.90(3H, m), 2.26–3.64(8H, m), 4.10–5.37(3H, m), 5.53–5.66 and 5.78–5.83(total 1H, each m), 5.99 and 6.27(total 1H, brd and dd, J=15.9 Hz and 4.8 Hz, 15.3 Hz), 6.76–7.85(13H, m), 8.05 and 8.13(total 2H, each d, each J=9.9 Hz), 8.08–8.50(2H, m), 8.88, 8.92 and 8.97(total 1H, each brs)

FAB-MS:635(M+H)

EXAMPLE 18

N-{(1RS,2RS,4E)-2-(4-chlorophenyl)-1-methyl-5-(2-naphthyl)-4-pentenyl}-N-(3,4-difluorobenzyl) carbamoylmethylsuccinic Acid $^1$H-NMR(CDCl$_3$)δ:0.84 and 0.89(total 3H, each d, J=7.1 Hz and 6.6 Hz), 2.30–3.92(8H, m), 4.09–4.73 and 4.75–5.40 (total 3H, each m), 5.66–5.79 and 5.89–6.02(total 1H, each m), 6.18 and 6.39(total 1H, each dd, J=6.7 Hz, 15.6 Hz and 6.1 Hz, 15.8 Hz), 6.82–7.74(14H, m)

FAB-MS:620(M+H)

EXAMPLE 19

N-(2-benzoxazolylmethyl)-N-{(1RS,2RS,4E)-2-(4-chlorophenyl)-1-methyl-5-(2-naphthyl)-4-pentenyl}-carbamoylmethylsuccinic Acid $^1$H-NMR(CDCl$_3$)δ:0.83–1.05(3H, m), 2.41–3.80(8H, m), 4.19–5.30(3H, m), 5.72–5.91(1H, m), 6.07–6.30(1H, m), 7.10–7.72(15H, m)

FAB-MS:625(M+H)

EXAMPLE 20

N-(2-benzo[b]thienylmethyl)-N-{(1RS,2RS,4E)-2-(4-chlorophenyl)-1-methyl-5-(2-naphthyl)-4-pentenyl}-carbamoylmethylsuccinic Acid $^1$H-NMR(CDCl$_3$)δ:0.87–1.05(3H, m), 2.38–3.80(8H, m), 4.02–5.20(2H, m), 5.48–5.67, 5.83–6.00, 6.20–6.34 and 6.51–6.57(total 2H, each m), 6.91–7.82(16H, m)

FAB-MS:640(M+H)

EXAMPLE 21

N-{(1RS,2RS,4E)-1-methyl-2-(3,4-methylenedioxyphenyl)-5-(2-naphthyl)-4-pentenyl}-N-(2-naphthylmethyl)carbamoylmethylsuccinic Acid $^1$H-NMR(CDCl$_3$)δ:0.90 and 0.95(total 3H, each d, J=6.3 Hz and 6.7 Hz), 2.40–3.20 and 3.30–3.60(total 8H, each m), 4.00–4.20 and 4.30–4.90(total 3H, each m), 5.40–5.60 and 5.70–6.10(total 3H, each m), 6.30–6.40 and 6.50–6.80(total 4H, each m), 7.00–7.20 and 7.20–7.80(total 14H, each m)

FAB-MS:644(M+H)

EXAMPLE 22

Preparation of (2R*)-2-[N-{(1S*,2S*,4E)-2-(4-chlorophenyl)-1-methyl-5-(2-naphtyl)-4-pentenyl}-N-(2-naphthylmethyl)carbamoylmethyl]succinic Acid 190 mg of N-{(1S*,2S*,4E)-2-(4-chlorophenyl)-1-methyl-5-(2-naphtyl)-4-pentenyl}-2-naphthylmethylamine obtained in Reference Example 2, 75 mg of 4-dimethylaminopyridine and 175 mg of 1,2-di-tert-butyl (R*)-1,2,3-propane tricarboxylate obtained in Reference Example 3, were dissolved in 7 ml of methylene chloride, and 117 mg of 1-ethyl-3-(3-dimethylaminopropyl) carbodiimide hydrochloride was added under cooling with ice with stirring, followed by stirring at room temperature for 4 hours. The reaction solution was diluted with methylene chloride and then sequentially washed with 1N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by medium pressure liquid chromatography (Lobar column™, sizeB, Lichroprep™Si60F, manufactured by Merck Co.; hexane/ethyl acetate=10/1→5/1) to obtain 274 mg (yield: 92%) of a di-tert-butyl ester of the above-identified compound.

240 mg of the ester obtained as described above, was dissolved in 5 ml of formic acid and stirred at room temperature for one hour. Then, formic acid was distilled off under reduced pressure. Toluene was added to the residue, and evaporation to dryness was again conducted under reduced pressure. The residue was treated with methylene chloride-hexane to obtain 191 mg (yield: 94%) of the above-identified compound as white crystalline powder, mp: 125°–127° C., $[\alpha]_D^{20}$+73.4° (c 1.0, methanol).

$^1$H-NMR(CDCl$_3$+CD$_3$OH)δ:0.92 and 0.97(total 3H, each d, each J=6.6 Hz), 2.20–3.55(8H, m), 4.15–4.30(1H, m), 4.47 and 4.72(total 1H, each d, J=18.3 Hz and 17.7 Hz), 4.74 and 4.85(total 1H, each d, J=18.3 Hz and 17.7 Hz), 5.45 and 5.95(total 1H, each dt, J=15.6 Hz, 7.8 Hz and 15.6 Hz, 6.3 Hz), 5.75 and 6.38(total 1H, each d, each J=15.6 Hz), 6.99–7.88(18H, m)

FAB-MS:635(M+H)

Compounds of Example 23 to 25 were prepared in the same manner as in Example 22 except that instead of N-{(1S*,2S*,4E)-2-(4-chlorophenyl)-1-methyl-5-(2-naphthyl)-4-pentenyl}-2-naphthylmethylamine and/or 1,2-di-tert-butyl (R*)-1,2,3-propanetricarboxylate, used as the starting material in the above reaction, N-{(1R*,2R*,4E)-2-(4-chlorophenyl)-1-methyl-5-(2-naphthyl)-4-pentenyl}-2-naphthylmethylamine and/or 1,2-di-tert-butyl (S*)-1,2,3-propanetricarboxylate was used.

EXAMPLE 23

(2R*)-2-[N-{(1R*,2R*,4E)-2-(4-chlorophenyl)-1-methyl-5-(2-naphthyl)-4-pentenyl}-N-(2-naphthylmethyl)carbamoylmethyl]succinic Acid mp: 158°–161° C. $[\alpha]_D^{20}$–81.4° (c 1.0, methanol).

$^1$H-NMR(CDCl$_3$+CD$_3$OH)δ:0.93 and 0.98(total 3H, each d, each J=6.6 Hz), 2.23–3.56(8H, m), 4.15–4.30(1H, m), 4.52 and 4.69(total 1H, each d, each J=18.3 Hz), 4.69 and 4.86(total 1H, each d, each J=18.3 Hz), 5.45 and 5.95(total 1H, each dt, J=15.3 Hz, 7.2 Hz and 15.9 Hz, 6.6 Hz), 5.74 and 6.37(total 1H, each d, J=15.3 Hz and 15.9 Hz), 6.96–7.86(18H, m)

FAB-MS:635(M+H)

EXAMPLE 24

(2S*)-2-[N-{(1R*,2R*,4E)-2-(4-chlorophenyl)-1-methyl-5 -(2-naphthyl)-4-pentenyl}-N-(2-naphthylmethyl)carbamoylmethyl]succinic Acid mp125°–127° C. $[\alpha]_D^{20}$–80.3° (c 1.0, methanol).

$^1$H-NMR(CDCl$_3$+CD$_3$OD)δ:0.92 and 0.97(total 3H, each d, each J=6.6 Hz), 2.20–3.55(8H, m), 4.15–4.30(1H, m), 4.47 and 4.72(total 1H, each d, J=18.3 Hz and 17.7 Hz), 4.72 and 4.85(total 1H, each d, J=18.3 Hz and 17.7 Hz), 5.45 and 5.95(total 1H, each dt, J=15.6 Hz, 7.8 Hz and 15.6 Hz, 6.3 Hz), 5.75 and 6.38(total 1H, each d, each J=15.6 Hz), 6.99–7.88(18H, m)

FAB-MS:635(M+H)

EXAMPLE 25

(2S*)-2-[N-{(1S*,2S*,4E)-2-(4-chlorophenyl)-1-methyl-5-(2-naphthyl)-4-pentenyl}-N-(2-naphthylmethyl)carbamoylmethyl]succinic Acid mp156°–158° C. $[\alpha]_D^{20}$+83.4° (c 1.0, methanol).

$^1$H-NMR(CDCl$_3$+CD$_3$OH)δ:0.93 and 0.98(total 3H, each d, each J=6.6 Hz), 2.20–3.55(8H, m), 4.15–4.30(1H, m),4.52 and 4.69(total 1H, each d, J=18.3 Hz and 15.9 Hz), 4.71 and 4.86(total 1H, each d, J=15.3 Hz and 15.9 Hz), 5.42 and 5.87(total 1H, each dt, J=15.6 Hz, 7.2 Hz and 15.9 Hz, 6.6 Hz), 5.75 and 6.38(total 1H, each d, J=15.6 Hz and 15.9 Hz), 6.96–7.86(18H, m)

FAB-MS:635(M+H)

EXAMPLE 26

Preparation of 5-[N-{(1RS,2RS,4E)-2-(4-chlorophenyl)-1-methyl-5-(2-naphthyl)-4-pentenyl}-N-(2-naphthylmethyl)-carbamoyl]pentanoic Acid 69 mg of N-{(1RS,2RS,4E)-2-(4-chlorophenyl)-1-methyl-5-(2-naphthyl)-4-pentenyl}-2-naphthylmethylamine obtained in Reference Example 1, 38 mg of monoethyl adipate and 27 mg of 4-dimethylaminopyridine, were dissolved in 2 ml of methylene chloride, and 42 mg of 1-ethyl-3-(3-dimethylaminopropyl)carbodiimide hydrochloride was added thereto, followed by stirring at room temperature for 24 hours. The reaction solution was diluted with ethyl ether, then sequentially washed with 1N hydrochloric acid, a saturated sodium hydrogencarbonate aqueous solution and a saturated sodium chloride aqueous solution, and dried over anhydrous magnesium sulfate. The drying agent was filtered off, and then, the solvent was distilled off under reduced pressure. The residue was purified by silica gel column chromatography (hexane/ethyl acetate=5/1). Then, the obtained ethyl ester of the above identified compound was added to a mixture of 1 ml of 1N sodium hydroxide aqueous solution and 1 ml of ethanol, followed by stirring at room temperature overnight. The reaction solution was acidified by an addition of 2 ml of 1N hydrochloric acid and then extracted by an addition of ethyl ether. The organic layer was washed with a saturated sodium chloride aqueous solution and then dried over anhydrous magnesium sulfate. The drying agent was filtered off, and then, the solvent was distilled off. The residue was purified by silica gel thin layer chromatography (Kieselgel™ 60F$_{254}$, Art 5744, manufactured by Merck Co.: chloroform/methanol=10/1) to obtain 67 mg (yield: 76%) of the above-identified compound.

$^1$H-NMR(CDCl$_3$)δ:0.92 and 0.97(total 3H, each d, J=6.8 Hz and 6.6 Hz), 1.50–1.95(4H, m), 2.20–2.90(7H, m), 2.90–3.10, 4.10–4.25(total 1H, each brs), 4.48 and 4.90(total 1H, each d, each J=18.3 Hz), 4.57(1H, d, J=18.3 Hz), 5.42 and 5.98(total 1H, dt, each J=7.3 Hz, 15.9 Hz), 5.70 and 6.36(total 1H, each d, each J=15.9 Hz), 6.95–7.90(18H, m)

FAB-MS:604(M+H)

EXAMPLE 27

Preparation of (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinic Acid and (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl]succinic Acid (1) Preparation of Di-tert-butyl (2R*)-2-[N-{(1RS,2RS)-4,4-diethoxy-1-methyl-2-(3,4-methylenedioxyphenyl)butyl}-N-(2-naphthylmethyl)carbamoylmethyl]succinate 436 mg of N-{(1RS,2RS)-4,4-diethoxy-1-methyl-2-(3,4-methylenedioxyphenyl)butyl}-2-naphthylmethylamine obtained in a manner similar to Reference Example 1, 346 mg of 1,2-di-tert-butyl (R*)-1,2,3-propanetricarboxylate obtained in Reference Example 3 and 122 mg of 4-dimethylaminopyridine, were dissolved in 5 ml of methylene chloride, and 249 mg of 1-ethyl-3-(3-dimethylaminopropyl)carbodiimide hydrochloride was added thereto, followed by stirring at room temperature for 14 hours. The reaction solution was diluted with ethyl acetate, then, sequentially washed with 1N hydrochloric acid, saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=10/1→5/1) to obtain 636 mg (yield: 90%) of the above-identified compound as a colorless foam.

(2) Preparation of Di-tert-butyl (2R*)-2-[N-{(1RS,2RS)-3-formyl-1-methyl-2-(3,4-methylenedioxyphenyl)propyl}-N-(2-naphthylmethyl)carbamoylmethyl]succinate 636 mg of di-tert-butyl (2R*)-2-[N-{(1RS,2RS)-4,4-diethoxy-1-methyl-2-(3,4-methylenedioxyphenyl)butyl}-N-(2-naphthylmethyl)carbamoylmethyl]succinate was dissolved in 12 ml of tetrahydrofuran, and 3 ml of 2N hydrochloric acid was added thereto, followed by stirring at room temperature for 3 hours. To the reaction solution, a saturated sodium hydrogencarbonate aqueous solution was added, and the mixture was extracted with ethyl acetate. Then, the organic layer was washed with a saturated sodium chloride aqueous solution and dried over anhydrous magnesium sulfate. The drying agent was filtered off, and then, the solvent was distilled off under reduced pressure to obtain 567 mg (yield: quantitative) of the above-identified compound as colorless oily substance.

(3) Preparation of Di-tert-butyl (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinate 53 mg of 60% oily sodium hydride was suspended in 5 ml of tetrahydrofuran, and 634 mg of 2-benzoxazolylmethyl(triphenyl)phosphonium bromide was added thereto, followed by stirring at room temperature for 30 minutes. 5 ml of a tetrahydrofuran solution containing 563 mg of di-tert-butyl (2R*)-2-[N-{(1RS,2RS)-3-formyl-1-methyl-2-(3,4-methylenedioxyphenyl)propyl}-N-(2-naphthylmethyl)carbamoylmethyl]succinate was added thereto, followed by stirring at room temperature for 12 hours. Then, water was added to the reaction solution, and the mixture was extracted with ethyl acetate. The organic layer was washed with a saturated sodium chloride aqueous solution and then dried over anhydrous magnesium sulfate. The drying agent was filtered off, and then, the solvent was distilled off under reduced pressure. The residue was purified by silica gel chromatography (hexane/ethyl acetate=10/1→5/1) to obtain 528 mg (yield: 79%) of the above-identified compound and 105 mg (yield: 16%) of Z-isomer of the above-identified compound, respectively, as a colorless foam.

(4) Preparation of (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinic Acid 486 mg of di-tert-butyl (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinate was dissolved in 10 ml of formic acid, followed by stirring at room temperature for 12 hours. Then, formic acid was distilled off under reduced pressure to obtain 412 mg (yield: quantitative) of the above-identified compound as white solid.

$^1$H-NMR(CDCl$_3$)δ:0.91–1.00(3H, m), 2.30–3.70(8H, m), 4.20–5.30(3H, m), 5.90–5.94(2H, m), 6.43(1H, d, J=15.7 Hz), 6.57–6.76(4H, m), 7.26–7.84(11H, m)

FAB-MS:635(M+H)

By the same treatment as above except that di-tert-butyl (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl]succinate was used, Z-isomer of the above-identified compound was obtained.

Compounds of Examples 28 to 44 were prepared in the same manner as in Example 27 except that instead of N-{(1RS,2RS)-4,4-diethoxy-1-methyl-2-(3,4-methylenedioxyphenyl)butyl}-2-naphthylmethylamine and/ or 1,2-di-tert-butyl (R*)-1,2,3-propanetricarboxylate and/or 2-benzoxazolylmethyl(triphenyl)phosphonium bromide, used as the starting material in the above reaction, the corresponding amine derivative and/or the carboxylic acid derivative and/or the phosphonium salt derivative, was used.

EXAMPLE 28

(2R*)-2-[N-(2-benzo[b]furanylmethyl)-N-{(1RS,2RS,4E)-5-(2-benzoxazolyl)-1-methyl-2-(3,4-methylenedioxyphenyl)-4-pentenyl}carbamoylmethyl]succinate $^1$H-NMR(CD$_3$OH)δ:0.99 and 1.09(total 3H, each d, J=6.6 Hz and 7.5 Hz), 2.40–3.40(8H, m), 4.25–4.35 and 4.60–5.00 (total 3H, each m), 5.90 and 5.93(total 2H, each s), 6.03, 6.05 and 6.11(total 1H, each d, J=16.0 Hz, 16.0 Hz and 16.3 Hz), 6.53–6.61(1H, m), 6.70–6.92(4H, m), 7.10–7.60(8H, m)

FAB-MS:625(M+H)

EXAMPLE 29

(2R*)-2-[N-(2-benzo[b]thienylmethyl)-N-{(1RS,2RS,4E)-5-(2-benzoxazolyl)-1-methyl-2-(3,4-methylenedioxyphenyl)-4-pentenyl}carbamoylmethyl]succinic Acid $^1$H-NMR(CD$_3$OD)δ:1.02–1.10(3H, m), 2.44–3.40(8H, m), 4.20–4.30 and 4.72–5.05(total 3H, each m), 5.76, 5.81, 6.24, and 6.26(total 1H, each d, J=16.1 Hz, 15.5 Hz, 16.2 Hz and 16.2 Hz), 5.91 and 5.92(total 2H, each s), 6.31–6.39 and 6.61–6.71(total 1H, each m), 6.73–6.91(3H, m), 7.10–7.82 (9H, m)

FAB-MS:641(M+H)

EXAMPLE 30

(2R*)-2-[N-[(1RS,2RS,4E)-5-(2-benzoxazolyl)-2-{3,4-bis(methoxycarbonyl)phenyl}-1-methyl-4-pentenyl]-N-(2-naphthylmethyl)carbamoylmethyl] succinic Acid $^1$H-NMR(CD$_3$COCD$_3$)δ:0.90–1.06(3H, m), 2.60–3.60 (8H, m), 4.52–5.12(3H, m), 5.96–6.76(2H, m), 7.23–8.05 (14H, m)

FAB-MS:637(M+H)

EXAMPLE 31

(2R*)-2-[N-(2-benzo[b]thienylmethyl)-N-{(1RS,2RS,4E)-5-(2-benzoxazolyl)-2-(4-methoxycarbonylphenyl)-1-methyl-4-pentenyl}carbamoylmethyl]succinic Acid $^1$H-NMR(CDCl$_3$)δ:0.84–1.08(3H, m), 2.30–3.68(8H, m), 3.90(3H, s), 4.20–5.43(3H, m), 5.99–6.58(2H, m), 7.13–7.77(11H, m), 7.95–8.10(2H, m)

FAB-MS:655(M+H)

EXAMPLE 32

(2R*)-2-[N-(2-benzo[b]furanylmethyl)-N-{(1RS,2RS,4E)-5-(2-benzoxazolyl)-2-(4-methoxycarbonylphenyl)-1-methyl-4-pentenyl}carbamoylmethyl]succinic Acid $^1$H-NMR(CDCl$_3$)δ:0.85–1.04(3H, m), 2.47–3.63(8H, m), 3.88(3H, s), 4.20–5.34(3H, m), 6.09–6.74(3H, m), 7.07–7.62(10H, m)

FAB-MS:639(M+H)

EXAMPLE 33

(2R*)-2-[N-(2-benzo[b]thienylmethyl)-N-{(1RS, 2RS,4E)-5-(2-benzoxazolyl)-2-(4-cyanophenyl)-1-methyl-4-pentenyl}carbamoylmethyl]succinic Acid $^1$H-NMR(CD$_3$COCD$_3$)D:1.04, 1.10 and 1.11(total 3H, each d, J=6.6 Hz, 6.6 Hz and 6.3 Hz), 2.59–6.63(8H, m), 4.47–5.52(3H, m), 4.47–5.52(3H, m), 5.90–6.71(2H, m), 7.23–7.90(13H, m)

FAB-MS:622(M+H)

EXAMPLE 34

(2R*)-2-[N-(5-benzo[b]thienylmethyl)-N-{(1RS, 2RS,4E)-5-(2-benzoxazolyl)-2-(4-methoxycarbonylphenyl)-1-methyl-4-pentenyl}carbamoylmethyl]succinic Acid $^1$H-NMR(CD$_3$COCD$_3$)δ:0.87–1.03(3H, m), 2.56–3.62 (8H, m), 3.84(3H, s), 4.34–5.05(3E, m), 5.95–6.71(2H, m), 7.23–8.04(13H, m)

FAB-MS:655(M+H)

EXAMPLE 35

N-{(1RS,2RS,4E)-5-(3-chloro-4-methylphenyl)-2-(4-chlorophenyl)-1-methyl-4-pentenyl}-N-(2-naphthylmethyl)carbamoylmethylsuccinic Acid $^1$H-NMR(CD$_3$OD)δ:0.80–0.95 and 0.99(total 3H, m and d, J=6.1 Hz), 2.21 and 2.25(total 3H, each s), 2.20–3.50(8H, m), 4.30–5.45(3H, m), 5.62–5.80(1H, m), 6.01(1H, d, J=15.7 Hz), 6.45–6.70, 6.80–7.60 and 7.80–7.90(total 14H, each m)

FAB-MS:632(M+H)

EXAMPLE 36

N-{(1RS,2RS,4Z)-5-(3-chloro-4-methylphenyl)-2-(4-chlorophenyl)-1-methyl-4-pentenyl}-N-(2-naphthylmethyl)carbamoylmethylsuccinic Acid $^1$H-NMR(CD$_3$OD)δ:0.75–0.90(3H, m), 2.35(3H, s), 2.30–3.40(8H, m), 4.20–4.90(3H, m), 5.00–5.15 and 5.25–5.40(total 1H, each m), 6.07, 6.10 and 6.21(total 1H, each d, each J=11.7 Hz), 6.90–7.05, 7.05–7.30, 7.30–7.50 and 7.60–7.90(total 14H, each m)

FAB-MS:632(M+H)

EXAMPLE 37

N-{(1RS,2RS,4E)-5-(2-benzo[b]furanyl)-2-(4-chlorophenyl)-1-methyl-4-pentenyl}-N-(2-naphthylmethyl)carbamoylmethylsuccinic Acid $^1$H-NMR(CD$_3$OH)δ:0.85–0.95 and 0.97(total 3H, m and d, J=6.6 Hz), 2.30–3.50(8H, m), 4.30–4.40 and 4.60–5.00 (total 3H, m), 5.44, 5.51 and 5.99(total 1H, each d, each J=15.9 Hz), 5.52–5.70 and 5.94–6.06(total 1H, each m), 6.10, 6.15 and 6.36(total 1H, each d, each J=2.0 Hz), 7.05–7.60 and 7.75–7.90(total 15H, m)

FAB-MS:624(M+H)

EXAMPLE 38

N-{(1RS,2RS,4Z)-5-(2-benzo[b]furanyl)-2-(4-chlorophenyl)-1-methyl-4-pentenyl}-N-(2-naphthylmethyl)carbamoylmethylsuccinic Acid $^1$H-NMR(CD$_3$OD)δ:0.83–1.00(3H, m), 2.50–3.50(8H, m), 4.40–5.25 and 5.35–5.50(total 3H, each m), 6.04, 6.07 and 6.16(total 1H, each d, each J=12.0 Hz), 6.57, 6.60 and 6.63(total 1H, each s), 7.15–7.90(15H, m)

FAB-MS:624(M+H)

EXAMPLE 39

N-{(1RS,2RS,4E)-5-(2-benzoxazolyl)-2-(4-chlorophenyl)-1-methyl-4-pentenyl}-N-(2-naphthylmethyl)carbamoylmethyl-succinic Acid $^1$H-NMR(CDCl$_3$)δ:0.80–1.02(3H, m), 2.25–3.75(8H, m), 4.19–5.40(3H, m), 6.03–6.61(2H, m), 6.97–7.86(15H, m)

FAB-MS:625(M+H)

EXAMPLE 40

N-{(1RS,2RS,4Z)-5-(2-benzoxazolyl)-2-(4-chlorophenyl)-1-methyl-4-pentenyl}-N-(2-naphthylmethyl)carbamoylmethyl-succinic Acid $^1$H-NMR(CDCl$_3$)δ:0.76–0.97(3H, m), 2.30–3.60(8H, m), 4.40–5.40(3H, m), 5.80–6.60(2H, m), 6.95–8.05(15H, m)

FAB-MS:625(M+H)

EXAMPLE 41

N-{(1RS,2RS,4E)-5-(2-benzimidazolyl)-2-(4-chlorophenyl)-1-methyl-4-pentenyl}-N-(2-naphthylmethyl)carbamoylmethylsuccinic Acid $^1$H-NMR(CD$_3$OH)δ:0.91–0.97(3H, m), 2.44–2.84(5H, m), 3.00–3.66(4H, m), 4.45–5.10(2H, m), 6.12–6.53(2H, m), 7.16–7.19(2H, m), 7.25–7.34(5H, m), 7.44–7.46(4H, m), 7.71–7.88(4H, m)

FAB-MS:622(M+H)

EXAMPLE 42

N-{(1RS,2RS,4E)-2-(4-chlorophenyl)-1-methyl-5-(3,4-methylenedioxyphenyl)-4-pentenyl}-N-(2-naphthylmethyl)carbamoylmethylsuccinic Acid $^1$H-NMR(CDCl$_3$)δ:0.80–1.00(3H, m), 2.10–3.20 and 3.30–3.70(total 8H, each m), 4.35–4.80(3H, m), 5.10–5.30 and 5.60–5.70(total 1H, each m), 5.86 and 5.88(total 2H, each s), 5.50–5.60, 6.11 and 6.14(total 1H, m, d and d, J=15.6 Hz and 15.9 Hz), 6.20–6.35 and 6.50–6.70(total 3H, each m), 7.00–7.80(11H, m)

FAB-MS:628(M+H)

EXAMPLE 43

N-{(1RS,2RS,4E)-5-(2-benzothiazolyl)-2-(4-chlorophenyl)-1-methyl-4-pentenyl}-N-(2-naphthylmethyl)carbamoylmethylsuccinic Acid $^1$H-NMR(CDCl$_3$)δ:0.75–1.00(3H, m), 2.20–3.70(8H, m), 4.20–5.40(3H, m), 5.75–5.85 and 6.10–6.30(total 1H, m), 6.39, 6.43, 6.74 and 6.76(total 1H, each d, each J=15.9 Hz), 7.00–8.20(15H, m)

FAB-MS:641(M+H)

EXAMPLE 44

N-{(1RS,2RS,4E)-5-(2-benzoxazolyl)-2-(4-cyanophenyl)-1-methyl-4-pentenyl}-N-(2-naphthylmethyl)carbamoylmethylsuccinic Acid $^1$H-NMR(CD$_3$COCD$_3$)δ:0.84–1.01(3H, m), 2.50–3.78 (8H, m), 4.16–5.22(3H, m), 5.77–6.10 and 6.37(total 1H, m and brd, J=16.3 Hz), 6.62–6.73 and 6.89–7.06(total 1H, each m), 7.31–7.95(15H, m)

FAB-MS:616(M+H)

EXAMPLE 45

Preparation of 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic Acid (1) Preparation of Triethyl 4-[N-{(1RS,2RS,4E)-4,4-diethoxy-1-methyl-2-(3,4-methylenedioxyphenyl)-4-pentenyl}-N-(2-naphthylmethyl)carbamoyl]-1,2,3-butanetricarboxylate 80 mg of N-{(1RS,2RS)-4,4-diethoxy-1-methyl-2-(3,4-methylenedioxyphenyl)butyl}-2-naphthylmethylamine obtained in a manner similar to Reference Example 1, 100 mg of 2,3,4-triethyl 1,2,3,4-butanetetracarboxylate obtained in Reference Example 12 and 27 mg of 4-dimethylaminopyridine were dissolved in 5 ml of methylene chloride, and 43 mg of 1-ethyl-3-(3-dimethylaminopropyl)carbodiimide hydrochloride was added thereto, followed by stirring at room temperature overnight. The reaction solution was diluted with ethyl acetate and then sequentially washed with 1N hydrochloric acid, a saturated sodium hydrogencarbonate aqueous solution and a saturated sodium chloride aqueous solution. The organic layer was dried over anhydrous magnesium sulfate. The drying agent was filtered off, and then, the solvent was distilled off under reduced pressure. The residue was roughly purified by silica gel column chromatography (ethyl acetate) and then purified by medium pressure liquid chromatography (Lobar column™, size B, Lichroprep™Si60, manufactured by Merck Co.; hexane/ethyl acetate=2/1) to obtain 54 mg (yield: 40%) of the above-identified compound as a colorless foam.

(2) Preparation of 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic Acid The N-acylated compound obtained in the above step (1) was treated in the same manner as in Example 27 to obtain triethyl 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylate. The obtained ester was dissolved in 1 ml of tetrahydrofuran, and then 0.5 ml of a 3N sodium hydroxide aqueous solution was added thereto. The mixture was left to stand at room temperature overnight. The reaction solution was diluted with ethyl acetate and then acidified by an addition of 1N hydrochloric acid, and it was washed with a saturated sodium chloride aqueous solution and then dried over anhydrous magnesium sulfate. The drying agent was filtered off, and then, the solvent was distilled off under reduced pressure. The residue was purified by medium pressure liquid chromatography (Lobar column™, size A, RP-8, manufactured by Merck Co.; acetonitrile/0.1% trifluoroacetic acid aqueous solution=1/1) to obtain 14 mg (yield: 52%) of the above-identified compound as white powder.

$^1$H-NMR(CDCl$_3$+CD$_3$OD)δ:0.80–1.00(3H, m), 2.30–3.75(9H, m), 4.20–5.30(3H, m), 5.85–5.95(2H, m), 6.40–6.80(5H, m), 7.20–7.50(6H, m), 7.55–7.85(5H, m)

FAB-MS:693(M+H)

Compounds of Examples 46 to 50 were obtained in the same manner as in Example 45 except that instead of 2,3,4-triethyl 1,2,3,4-butanetetracarboxylate used as the starting material in the above reaction, the corresponding carboxylic acid derivative was used.

EXAMPLE 46

3-[N-{(1RS,2RS,4E)-5-(2-benzoxazolyl)-1-methyl-2-(3,4-methylenedioxyphenyl)-4-pentenyl}-N-(2-naphthylmethyl)-carbamoyl]-1,2,2-propanetricarboxylic Acid $^1$H-NMR(CD$_3$COCD$_3$)δ:0.82–1.04(3H, m), 2.50–3.90 (7H, m), 5.93–7.97(21H, m)

FAB-MS:679(M+H)

EXAMPLE 47

(2S,3R)-4-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]-3-carboxy-2-hydroxybutanoic Acid $^1$H-NMR(CDCl$_3$)δ:0.99 and 1.09(total 3H, each d, J=7.0 Hz and 6.6 Hz), 2.16–2.98(5H, m), 3.32–3.70(1H, m), 4.02–5.02(3H, m), 5.23–6.10(3H, m), 6.35–6.95(5H, m), 7.10–7.92(11H, m)

FAB-MS:651(M+H)

EXAMPLE 48

4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-carboxy-4-methoxybutanoic Acid $^1$H-NMR(CD$_3$COCD$_3$)δ:0.98–1.14(3H, m), 2.58–3.76 (6H, m), 3.36, 3.40, 3.45, 3.47, 3.56 and 3.65(total 3H, each s), 4.50–5.20(4H, m), 5.93–5.96(2H, m), 6.14–6.50(1H, m), 6.60–7.00(4H, m), 7.30–8.10(11H, m)

FAB-MS:665(M+H)

EXAMPLE 49

5-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-4-carboxy-3-carboxymethylpentanoic Acid $^1$H-NMR(CD$_3$COCD$_3$)δ:0.80–1.15(3H, m), 2.25–3.65 (11H, m), 4.30–5.30(3H, m), 5.90–6.60(2H, m), 6.10–7.03 (5H, m), 7.26–7.70(6H, m), 7.75–8.05(5H, m)

FAB-MS:707(M+H)

EXAMPLE 50

1-[N-{(1RS,2RS,4E)-5-(2-benzoxazolyl)-2-(4-methoxycarbonylphenyl)-1-methyl-4-pentenyl}-N-(2-naphthylmethyl)carbamoyl]-1,2,3-propanetricarboxylic Acid $^1$H-NMR(CD$_3$COCD$_3$)δ:0.82–1.10(3H, m), 2.60–3.90 (10H, m), 4.51–5.30(3H, m), 5.87–6.75(2H, m), 7.10–8.16 (15H, m)

FAB-MS:693(M+H)

EXAMPLE 51

Preparation of (3R*)- and (3S*)-4-[N-{(1RS,2RS, 4E)-5-(2-benzoxazolyl)-1-methyl-2-(3,4-methylenedioxyphenyl)-4 -pentenyl}-N-(2-naphthylmethyl)carbamoyl]-3-methoxybutanoic Acid Methyl (3RS)-4-[N-{(1RS,2RS,4E)-5-(2-benzoxazolyl)-1-methyl-2-(3,4-methylenedioxyphenyl)-4-pentenyl}-N-(2- naphthylmethyl)carbamoyl]-3-methoxybutanoate obtained in the same manner as in Example 45 except that monomethyl (RS)-3-methoxygultarate was used instead of 2,3,4-triethyl 1,2,3,4-butanetetracarboxylate used in Example 45, was separated by silica thin layer chromatography (Kieselgel™60F$_{254}$, Art™5744; hexane/ethyl acetate=2/1) to obtain (3R$^*$)- and (3S$^*$)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-methoxybutanoic acid methyl esters. 9.9 mg of the (3R$^*$)-isomer and 9.5 mg of the (3S$^*$)-isomer were, respectively, dissolved in a mixed solution of 1 ml of tetrahydrofuran and 0.5 ml of water, and 6.5 mg of lithium hydroxide monohydrate was added thereto. The mixtures were left to stand overnight at room temperature. The respective reaction solutions were diluted with ethyl ether and acidified by an addition of 2N hydrochloric acid, washed with a saturated sodium chloride aqueous solution and then dried over anhydrous magnesium sulfate. The drying agent was filtered off, and then, the solvent was distilled off under reduced pressure. The respective residues were purified by silica gel thin layer chromatography (Kieselgel™60F$_{254}$, Art™5744; chloroform/methanol=10/1) to obtain 7.5 mg (yield: 77%) of the above-identified compound named as the (3R$^*$)-isomer for the sake of convenience and 8.7 mg (yield: 97%) of the above-identified compound named as the (3S$^*$)-isomer, respectively as white powders.

(3R$^*$)-isomer $^1$H-NMR(CDCl$_3$)δ:0.83–1.06(3H, m), 2.41–3.06(7H, m), 3.38 and 3.51(total 3H, each s), 4.02–5.40(4H, m), 5.94(2H, s), 6.19–7.88(18H, m)

FAB-MS:621(M+H)

(3S$^*$)-isomer $^1$H-NMR(CDCl$_3$)δ:0.85–1.02(3H, m), 2.48–3.31(7H, m), 3.42 and 3.52(total 3H, each s), 4.17–5.35(4H, m), 5.94 and 5.96(total 2H, each s), 6.12–7.88(18H, m)

FAB-MS:621(M+H)

EXAMPLE 52

Preparation of N-{(1RS,2RS,4E)-5-(2-benzoxazolyl)-2-(4-carboxyphenyl)-1-methyl-4-pentenyl}-N-(2-naphthylmethyl) carbamoylmethylsuccinic Acid 8 mg of N-{(1RS,2RS,4E)-5-(2-benzoxazolyl)-2-(4-methoxycarbonylphenyl)-1-methyl-4-pentenyl}-N-(2-naphthylmethyl)carbamoylmethylsuccinic acid obtained in a manner similar to Example 27, was dissolved in 1 ml of methanol, and 0.5 ml of a 1N sodium hydroxide aqueous solution was added thereto. The mixture was left to stand at room temperature overnight. The reaction solution was diluted with ethyl acetate, then acidified by an addition of 1N hydrochloric acid, washed with a saturated sodium chloride aqueous solution and then dried over anhydrous magnesium sulfate. The drying agent was filtered off, and then, the solvent was evaporated to dryness under reduced pressure to obtain 8 mg (yield: quantitative) of the above-identified compound as slightly yellow powder.

$^1$H-NMR(CD$_3$COCD$_3$+CDCl$_3$)δ:0.80–1.00(3H, m), 2.50–3.80(8H, m), 4.40–5.20(3H, m), 5.90–6.10, 6.60–7.00 and 6.37(total 2H, m and d, J=15.9 Hz), 7.20–8.10(15H, m)

FAB-MS:635(M+H)

EXAMPLE 53

Preparation of N-{(1RS,2RS,4E)-5-(2-benzoxazolyl)-1-methyl-2-{4-(N-methylcarbamoyl) phenyl}-4-pentenyl]-N-(2-naphthylmethyl) carbamoylmethylsuccinic Acid 86 mg of di-tert-butyl N-{(1RS,2RS,4E)-5-(2-benzoxazolyl)-2-(4-methylcarbonylphenyl)-1-methyl-4-pentenyl}-N-(2-naphthylmethyl)carbamoylmethylsuccinate obtained in a manner similar to Example 27, was dissolved in a mixed solution of 1 ml of tetrahydrofuran and 0.5 ml of water, and 49 mg of lithium hydroxide monohydrate was added thereto, followed by stirring at room temperature for 3 hours. The reaction solution was diluted with ethyl acetate, then acidified by an addition of 1N hydrochloric acid, washed with a saturated sodium chloride aqueous solution and then dried over anhydrous magnesium sulfate. The drying agent was filtered off, and then, the solvent was distilled off under reduced pressure. The residue was dissolved in 1 ml of methylene chloride, and 50 μl of triethylamine and 17 μl of isobutyl chloroformate were added thereto, followed by stirring at 0° C. for 30 minutes. 5 ml of a 40% monomethylamine-methanol solution, was added thereto, followed by stirring at room temperature for one hour. Then, the reaction solution was evaporated to dryness under reduced pressure, and the residue was purified by silica gel column chromatography (chloroform/methanol= 50/1→10/1) to obtain 47 mg (yield: 51%) of the above-identified compound i.e. the di-tert-butyl ester, as a colorless foam.

42 mg of the N-methylcarbamoyl compound obtained as described above, was dissolved in 1 ml of formic acid, and the solution was stirred at room temperature overnight and then evaporated to dryness under reduced pressure. Toluene was added to the residue, and evaporation to dryness under reduced pressure was again carried out, whereupon the product was purified by silica gel thin layer chromatography (Kieselgel™60F$_{254}$, Art™5744; chloroform/methanol/ acetic Acid=200/20/1) to obtain 32 mg (yield: 90%) of the above-identified compound as white powder.

$^1$H-NMR(CDCl$_3$)δ:0.75–1.00(3H, m), 2.20–3.70(8H, m), 2.93 and 2.95(total 3H, each s), 4.20–5.40(3H, m), 5.97, 6.03, 6.35 and 6.36(total 1H, each d, each J=15.9 Hz), 6.10–6.30 and 6.40–6.80(total 2H, each m), 7.10–8.00(15H, m)

FAB-MS:648(M+H)

EXAMPLE 54

Preparation of (2R$^*$)-2-[N-{(1RS,2RS,4E)-5-(2-benzoxazolyl)-2-(4-hydroxy-3-methoxyphenyl)-1-methyl-4-pentenyl}-N-(2-naphthylmethyl) carbamoylmethylsuccinic Acid 50 mg of di-tert-butyl (2R$^*$)-2-[N-{(1RS,2RS,4E)-5-(2-benzoxazolyl)-2-(3-methoxy-4-methoxymethyloxyphenyl)-1-methyl-4-pentenyl}-N-(2-naphthylmethyl) carbamoylmethyl]-succinate prepared in a manner similar to Example 27, was dissolved in 2 ml of formic acid, followed by stirring at room temperature overnight. Then, the reaction solution was evaporated to dryness under reduced pressure. Toluene was added to the residue, and evaporation to dryness under reduced pressure was again conducted to obtain 44 mg (yield: quantitative) of the above-identified compound as white powder.

$^1$H-NMR(CD$_3$COCD$_3$)δ:0.92–1.04(3H, m), 2.55–3.50 (8H, m), 3.82(3H, s), 4.40–5.10(3H, m), 6.02–7.95(16H, m)

FAB-MS:637(M+H)

EXAMPLE 55

Preparation of N-{(1RS,2RS,4E)-2-(4-hydroxymethylphenyl)-1-methyl-5-(2-naphthyl)-4-pentenyl}-N-(2-naphthylmethyl) carbamoylmethylsuccinic Acid 44 mg of N-{(1RS,2RS,4E)-2-(4-methoxycarbonylphenyl)-1-methyl-5-(2-naphthyl)-4- pentenyl}-2-naphthylmethylamine prepared in a manner similar to Reference Example 1 was dissolved in 1.5 ml of tetrahydrofuran, and 7 mg of lithium aluminum hydride was added thereto under cooling with ice with stirring, followed by stirring at the same temperature for 15 minutes. The reaction solution was diluted with ethyl ether, and then 5 g of moistened sodium fluoride was added thereto, followed by stirring at room temperature for 30 minutes. Insoluble matters were filtered off, and then, the filtrate was dried over anhydrous magnesium sulfate. The drying agent was filtered off, and then, the solvent was distilled off under reduced pressure. The residue was dissolved in 1 ml of methylene chloride, and 31 mg of chloroformylmethylsuccinic anhydride and 24 μl of triethylamine were added thereto, followed by stirring at room temperature for one hour. The reaction solution was evaporated to dryness under reduced pressure, and then the residue was dissolved in 1 ml of tetrahydrofuran and 0.5 ml of methanol, and 0.5 ml of a 1N sodium hydroxide aqueous solution was added thereto. The mixture was left to stand at room temperature overnight. The reaction solution was diluted with ethyl acetate and then acidified by an addition of 1N hydrochloric acid. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ ethyl acetate=1/1→chloroform/methanol=30/1) to obtain 42 mg (yield: quantitative) of the above-identified compound as slightly yellow powder.

$^1$H-NMR(CD$_3$COCD$_3$)δ:0.92 and 1.01(total 3H, each d, J=6.9 Hz and 6.6 Hz), 2.46–3.63(8H, m), 3.65–4.50(1H, m), 4.59 and 4.60(total 2H, each s), 4.76–5.04(2H, m), 5.52–5.67, 6.03 and 6.09(total 1H, m, td and td, each J=7.2 Hz, 16.0 Hz), 5.75–5.90 and 6.41(total 1H, m and d, J=16.0 Hz), 7.00–8.00(18H, m)

FAB-MS:630(M+H)

EXAMPLE 56

Preparation of N-{(1RS,2RS,4E)-2-(4-aminophenyl)-1-methyl-5-(2-naphthyl)-4-pentenyl}-N-(2-naphthylmethyl)carbamoylmethylsuccinic Acid 99 mg of di-tert-butyl N-{(1RS,2RS,4E)-1-methyl-5-(2-naphthyl)-2-(4-nitrophenyl)-4-pentenyl}-N-(2-naphthylmethyl)carbamoylmethylsuccinate as an intermediate of Example 10 was dissolved in 16 ml of 50% water-containing ethanol, and 146 mg of iron powder was added thereto, followed by heating to 60° C. Then, one drop of concentrated hydrochloric Acid was added thereto, and the mixture was heated and refluxed for one hour with stirring. The reaction solution was filtered through a cerite filter, and the filtrate was evaporated to dryness under reduced pressure and purified by silica gel column chromatography (hexane/ ethyl acetate=4/1) to obtain 99 mg of a di-tert-butyl ester of the above-identified compound.

18 mg of the amino compound thus obtained was dissolved in 3 ml of tetrahydrofuran, and 1 ml of a 3N sodium hydroxide aqueous solution was added, followed by heating at 80° C. for 2 hours. The reaction solution was left to cool, then acidified by an addition of 1N hydrochloric acid and extracted by an addition of ethyl acetate. The extract solution was washed with a saturated aqueous sodium chloride solution and then dried over anhydrous magnesium sulfate. The drying agent was filtered off, and the solvent was distilled off under reduced pressure. The residue was purified by column chromatography (Empore™ (manufactured by 3M Indastorial and Electronic Sector Co.); chloroform/ methanol=10/1) to obtain 9 mg (yield: 62%) of the above-identified compound as white solid.

$^1$H-NMR(CD$_3$OD)δ:0.90 and 1.00(total 3H, each d, J=6.9 Hz and 6.6 Hz), 2.20–3.47(8H, m), 4.25–5.00(3H, m), 5.30–6.05 and 6.27(total 2H, m and d, J=15.5 Hz), 6.60–6.80, 6.90–7.05, 7.25–7.70 and 7.80–7.90(18H, each m)

FAB-MS:615(M+H)

EXAMPLE 57

Preparation of Disodium (3RS,4RS)-4-[N-{(1RS, 2RS,4E)-5-(2-benzoxazolyl)-1-methyl-2-(3,4-methylenedioxyphenyl)-4-pentenyl}-N-(2-naphthylmethyl)carbamoyl]-3-carboxyl-4-hyroxybutanoate (1) Preparation of (2RS,3RS)-2-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylic Acid 47 mg of tert-butyl (2RS,3RS)-2-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylate prepared in a manner similar to Example 27 except that (2RS,3RS)-3-tert-butoxycarbonyl-5-oxotetrahydrofuran-2-carboxylic acid obtained in Reference Example 4 was used, instead of the 1,2-di-tert-butyl (R*)-1,2,3,-propanetricarboxylate in Example 27, was dissolved in 1 ml of formic acid, and the solution was left to stand at room temperature overnight. The reaction solution was distilled under reduced pressure. Then, toluene was added to the residue, followed by distillation again. The product was purified by silica gel column chromatography (hexane/ethyl acetate=2/1)→chloroform/ methanol=50/1) to obtain 20 mg (yield: 46%) of the above-identified compound as white solid.

$^1$H-NMR(CDCl$_3$)δ:0.99 and 1.10(total 3H, each d, J=6.2 Hz, 6.3 Hz), 2.50–3.10(5H, m), 4.15–4.25 and 4.37–4.47 (total H, each m), 4.50–5.35(4H, m), 5.73, 5.75, 5.88 and 5.94(total 2H, each s), 6.07 and 6.36(total 1H, each d, each J=15.8 Hz), 6.60–6.75(4H, m), 7.25–7.82(11H, m)

FAB-MS:633(M+H)

(2) Disodium (3RS,4RS)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-carboxy-4-hydroxybutanoate 8 mg of the lactone thus obtained was dissolved in a mixed solution of 1 ml of methanol and 1 ml of tetrahydrofuran, and 26 μl of a 1N sodium hydroxide aqueous solution was added under cooling with ice with stirring, followed by stirring at room temperature for 10 minutes. The reaction solution was evaporated to dryness under reduced pressure to obtain 10 mg (yield: quantitative) of the above-identified compound as white solid.

$^1$H-NMR(CDCl$_3$)δ:0.91 and 1.03(total 3H, each d, J=6.0 Hz and 6.7 Hz), 2.35–3.40(6H, m), 4.60–5.10(4H, m), 5.86 and 5.90(total 2H, each s), 5.90–6.95(5H, m), 7.28–8.01 (11H, m)

FAB-MS:695(M+H)

Compound of Examples 58 to 60 were prepared in the same manner as in Example 57 except that instead of (2RS,3RS)-3-tert-butoxycarbonyl-5-oxotetrahydrofuran-2-carboxylic acid used as the starting material in the above reaction, the corresponding carboxylic acid derivatives were employed.

EXAMPLE 58

N-{(1RS,2RS,4E)-5-(2-benzoxazolyl)-1-methyl-2-(3,4-methylenedioxyphenyl)-4-pentenyl}-N-(2-naphthylmethyl)-5-oxotetarhydrofuran-2-carboxyamide $^1$H-NMR(CDCl$_3$)δ:1.02 and 1.10(total 3H, each d, J=7.0 Hz and 6.7 Hz), 2.37–3.00(7H, m), 4.25–5.45(4H, m), 5.94–5.96(2H, m), 6.33(1H, d, J=16.2 Hz), 6.63–6.77(4H, m), 7.24–7.89(11H, m)

FAB-MS:589(M+H)

EXAMPLE 59

Sodium 4-[N-{(1RS,2RS,4E)-5-(2-benzoxazolyl)-1-methyl-2-(3,4-methylenedioxyphenyl)-4-pentenyl}-N-(2-naphthylmethyl)]carbamoyl-4-hydroxybutanoate $^1$H-NMR(CD$_3$OD)δ:0.96–1.09(3H, m), 1.85–2.77(7H, m), 2.95–3.55(1H, m), 4.50–5.15(3H, m), 5.87–5.90(2H, m), 6.00–6.40(1H, m), 6.64–6.93(4H, m), 7.26–7.92(11H, m)

FAB-MS:629(M+H)

EXAMPLE 60

4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-2-oxotetrahydrofuran-3-yl Acetic Acid $^1$H-NMR(CDCl$_3$)δ:1.00–1.10(3H, m), 2.50–3.80, 4.10–4.20 and 4.30–4.90(total 12H, each m), 5.91–5.96(2H, m), 6.00 and 6.43(total 1H, each d, each J=16.2 Hz), 6.58–6.70(4H, m), 7.26–7.84(11H, m)

FAB-MS:647(M+H)

EXAMPLE 61

Preparation of (2R*)-2-[N-{(1R*,2R*,4E)-5-(2-benzoxazolyl)-2-(4-methoxycarbonylphenyl)-1-methyl-4-pentenyl}-N-(2-naphthylmethyl) carbamoylmethyl]succinic acid and (2R*)-2-[N-{(1S*,2S*,4E)-5-(2-benzoxazolyl)-2-(4-methoxy-carbonylphenyl)-1-methyl-4-pentenyl)-N-(2-naphthylmethyl)carbamoylmethyl]succinic Acid (1) Preparation of Di-tert-butyl (2R*)-2-[N-{(1RS,2RS)-4,4-diethoxy-2-(4-methoxycarbonylphenyl)-1-methylbutyl}-N-(2-naphthylmethyl)carbamoylmethyl]succinate 485 mg of N-{(1RS,2RS)-4,4-diethoxy-2-(4-methoxycarbonylphenyl)-1-methylbutyl}-2-naphthylmethylamine prepared in a manner similar to Reference Example 1, 374 mg of 1,2-di-tert-butyl (R*)-1,2,3,-propanetricarboxylate prepared in Reference Example 3 and 98 mg of 4-dimethylaminopyridine, were dissolved in 5 ml of methylene chloride, and 621 mg of 1-ethyl-3-(3-dimethylaminopropyl)carbodiimide hydrochloride was added thereto, followed by stirring at room temperature for 3 hours. The reaction solution was diluted with methylene chloride and then sequentially washed with a 10% citric acid aqueous solution, a saturated sodium hydrogencarbonate aqueous solution and a saturated sodium chloride aqueous solution. The organic layer was dried over anhydrous magnesium sulfate. The drying agent was filtered off, and then, the solvent was distilled off under reduced pressure. The residue was purified by silica gel column chromatography (hexane/ethyl acetate=3/1) to obtain 275 mg (yield: 93%) of the above-identified compound as colorless oily substance.

(2) Preparation of Di-tert-butyl (2R*)-2-[N-{(1RS,2RS)-3-formyl-2-(4-methoxycarbonylphenyl)-1-methylpropyl}-N-(2-naphthylmethyl)carbamoylmethyl]succinate 725 mg of di-tert-butyl (2R*)-2-[N-{(1RS,2RS)-4,4-diethoxy-2-(4-methoxycarbonylphenyl)-1-methylbutyl}-N-(2-naphthylmethyl)carbamoylmethyl]succinate was dissolved in 15 ml of tetrahydrofuran, and 3.5 ml of 1N hydrochloric acid was added thereto, followed by stirring at 40° C. for 3 hours. A saturated sodium hydrogencarbonate aqueous solution was added to the reaction solution, and the mixture was extracted with ethyl acetate. Then, the organic layer was washed with a saturated sodium chloride aqueous solution and dried over anhydrous magnesium sulfate. The drying agent was filtered off, and then, the solvent was distilled off under reduced pressure to obtain 650 mg (yield: quantitative) of the above-identified compound as colorless oily substance.

(3) Preparation of Di-tert-butyl (2R*)-2-[N-{(1R*,2R*,4E)-5-(2-benzoxazolyl)-2-(4-methoxycarbonylphenyl)-1-methyl-4-pentenyl}-N-(2-naphthylmethyl)carbamoylmethyl]succinate and di-tert-butyl (2R*)-2-[N-{(1S*,2S*,4E)-5-(2-benzoxazolyl)-2-(4-methoxycarbonylphenyl)-1-methyl-4-pentenyl}-N-(2-naphthylmethyl)carbamoyl]succinate 58 mg of 60% oily sodium hydride was suspended in 4 ml of tetrahydrofuran, and 690 mg of 2-benzoxazolyl methyl (triphenyl)phosphonium bromide was added, followed by stirring at room temperature for 20 minutes. 3 ml of a tetrahydrofuran solution containing 629 mg of di-tert-butyl (2R*)-2-[N-{(1RS,2RS)-3-formyl-2-(4-methoxycarbonylphenyl)-1-methylpropyl}-N-(2-naphthylmethyl)carbamoylmethyl]succinate, was added thereto, followed by stirring at room temperature for 10 hours. Then, the reaction solution was acidified by an addition of 1N hydrochloric acid and extracted with ethyl ether. The organic layer was washed with a saturated sodium chloride aqueous solution and then dried over anhydrous magnesium sulfate. The drying agent was filtered off, and then, the solvent was distilled off under reduced pressure. The residue was roughly purified by medium pressure liquid chromatography (Lobar column™, size B, Lichroprep™Si60, manufactured by Merck Co.); hexane/ethyl acetate=3/1) and then separated by means of high performance liquid chromatography (Senshu Pak™, Silica-5301-N; hexane ethyl acetate=3/1), whereby two kinds of the above-identified compounds which are in the relationship of diastereomers, were obtained in amounts of 133 mg (yield: 18%) and 133 mg (yield: 18%), respectively, as colorless oily substances.

(4) Preparation of (2R*)-2-[N-{(1R*,2R*,4E)-5-(2-benzoxazolyl)-2-(4-methoxycarbonylphenyl)-1-methyl-4-pentenyl}-N-(2-naphthylmethyl)carbamoylmethyl]succinic acid and (2R*)-2-[N-{(1S*,2S*,4E)-5-(2-benzoxazolyl)-2-(4-methoxycarbonylphenyl)-1-methyl-4-pentenyl}-N-(2-naphthylmethyl)carbamoylmethyl Succinic Acid By conducting the same reaction as in Example 27(4), the above-identified compounds i.e. two diastereomers were obtained, respectively, as white powders. (2R*)-2-[N-{(1R*,2R*,4E)-5-(2-benzoxazolyl)-2-(4-methoxycarbonylphenyl)-1-methyl-4-pentenyl}-N-(2-naphthylmethyl)carbamoylmethyl]succinic Acid $^1$H-NMR(CD$_3$COCD$_3$)δ:0.94 and 1.01(total 3H, each d, J=6.3 Hz and 6.6 Hz), 2.60–3.14(6H, m), 3.30–3.49(2H, m), 3.84(3H, s), 4.50–4.62 and 4.80–5.50(total 1H, each m), 4.84–5.09(2H, m), 6.00 and 6.34(total 1H, each d, J=16.9 Hz and 16.2 Hz), 6.25–6.34 and 6.67(total 1H, m and dt, J=7.2 Hz, 16.2 Hz), 7.26–7.33(2H, m), 7.40–7.65(7H, m), 7.82–7.98(6H, m)

mp121°–122° C.

FAB-MS:649(M+H)

(2R*)-2-[N-{(1S*,2S*,4E)-5-(2-benzoxazolyl)-2-(4-methoxycarbonylphenyl)-1-methyl-4-pentenyl}-N-(2-naphthylmethyl)carbamoylmethyl]succinic Acid $^1$H-NMR(CD$_3$COCD$_3$)δ:0.93 and 1.00(total 3H, each d, J=6.4 Hz and 6.6 Hz), 2.60–3.51(8H, m), 3.84(3H, s), 4.51–4.62 and 4.80–5.30(total 1H, each m), 4.86(1H, brdd, J=6.3 Hz, 14.7 Hz), 5.04(1H, d, J=15.8 Hz), 6.03 and 6.34(total 1H, each d, J=16.0 Hz and 16.5 Hz), 6.30–6.41 and 6.67(total 1H, m and dt, J=7.1 Hz, 16.0 Hz), 7.27–7.34(2H, m), 7.41–7.65(7H, m), 7.82–8.01(6H, m)

mp115°–116° C.

FAB-MS:649(M+H)

Compounds of Examples 62 and 63 were prepared in the same manner as in Example 61 except that di-tert-butyl (2R*)-2-[N-(2-benzo[b]thienylmethyl)-N-{(1RS,2RS)-4,4-diethoxy-1-methyl-2-(3,4-methylenedioxyphenyl)butyl}carbamoylmethyl]succinate was used instead of di-tert-butyl (2R*)-2-[N-{(1RS,2RS)-4,4-diethoxy-2-(4-methoxycarbonylphenyl)-1-methylbutyl}-N-(2-naphthylmethyl)carbamoylmethyl]succinate used as the starting material for the above reaction.

EXAMPLE 62

(2R*)-2-[N-(2-benzo[b]thienylmethyl)-N-{(1S*,2S*,4E)-5-(2-benzoxazolyl)-1-methyl-2-(3,4-methylenedioxyphenyl)-4-pentenyl)carbamoylmethyl]succinic Acid $^1$H-NMR(CD$_3$OD)δ:1.03 and 1.09(total 3H, each d, J=7.0 Hz and 7.6 Hz), 2.45–3.34(8H, m), 4.26–4.28 and 4.71–5.05 (total 3H, each m), 5.77 and 6.26(total 1H, each d, J=16.2 Hz and 15.8 Hz), 5.91 and 5.92(total 2H, each s), 6.33 and 6.66(total 1H, each dt, J=8.5 Hz, 15.8 Hz and 8.0 Hz, 15.7 Hz), 6.74–6.90(3H, m), 7.10–7.82(9H, m)

FAB-MS:641(M+H)

EXAMPLE 63

(2R*)-2-[N-(2-benzo[b]thienylmethyl)-N-{(1R*,2R*,4E)-5-(2-benzoxazolyl)-1-methyl-2-(3,4-methylenedioxyphenyl)-4-pentenyl}carbamoylmethyl]succinic Acid $^1$H-NMR(CD$_3$OD)δ:1.03 and 1.08(total 3H, each d, J=6.7 Hz and 6.5 Hz), 2.50–3.50(8H, m), 4.25–4.31 and 4.71–4.94 (total 3H, each m), 5.80 and 6.24(total 1H, each d, each J=15.8 Hz), 5.91 and 5.92(total 2H, each s), 6.36 and 6.64(total 2H, each dr, J=7.6 Hz, 16.1 Hz and 7.6 Hz, 16.4 Hz), 6.69–6.91(3H, m), 7.12–7.83(9H, m)

FAB-MS:641(M+H)

EXAMPLE 64

Preparation of (2R*)-2-[N-{(1RS,2RS)-5-(2-benzoxazolyl)-1-methyl-2-(3,4-methylenedioxyphenyl)pentyl}-N-(2-naphthylmethyl)carbamoylmethyl]succinic Acid 100 mg of di-tert-butyl (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl] succinate obtained in Example 27(3), was dissolved in 3 ml of ethanol, and 11 mg of a 10% palladium-carbon catalyst, followed by catalytic reduction for 24 hours at room temperature under hydrogen atmospheric pressure. The catalyst was filtered off, and then, the solvent was distilled off under reduced pressure. The residue was purified by silica gel column chromatography (hexane/ethyl acetate=7/1→4/1) to obtain 72 mg (yield: 68%) of the di-tert-butyl derivative of the above compound as colorless oily substance.

72 mg of the ester thus obtained was dissolved in 2 ml of formic acid, followed by stirring at room temperature for 12 hours. Then, the formic acid was distilled off under reduced pressure to obtain 63 mg (yield: quantitative) of the above-identified compound as white solid.

$^1$H-NMR(CDCl$_3$)δ:0.86–0.96(3H, m), 1.30–1.70(4H, m), 2.30–3.60 and 3.98–4.10(total 8H, each m), 4.40–5.20(3H, m), 5.84–5.93(2H, m), 6.40–6.46 and 6.56–6.73(3H, m), 7.16–7.60 and 7.70–7.83(11H, m)

FAB-MS:637(M+H)

Compounds of Examples 65 and 66 were prepared in the same manner as in Example 64 except that instead of di-tert-butyl (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl] succinate used as the starting material in the above reaction, di-tert-butyl (2R*)-2-[N-(2-benzo[b]thienylmethyl)-N-{(1RS,2RS,4Z)-5-(2-benzoxazolyl)-1-methyl-2-(3,4-methylenedioxyphenyl)-4-pentenyl}carbamoylmethyl] succinate and di-tert-butyl (2R*)-2-[N-{(1R*,2R*,4Z)-5-(2-benzoxazolyl)-2-(4-methoxycarbonylphenyl)-1-methyl-4-pentenyl}-N-(2-naphthylmethyl)carbamoylmethyl] succinate, were used.

EXAMPLE 65

(2R*)-2-[N-(2-benzo[b]thienylmethyl)-N-{(1RS,2RS)-5-(2-benzoxazolyl)-1-methyl-2-(3,4-methylenedioxyphenyl)-pentyl}carbamoylmethyl] succinic Acid $^1$H-NMR(CD$_3$OH)δ:0.95–1.05(3H, m), 1.27–1.60(4H, m), 2.30–3.40(8H, m), 4.10–4.20 and 4.60–5.00(total 3H, each m), 5.90(2H, s), 6.72–6.90(3H, m), 7.10–7.80(9H, m)

FAB-MS:643(M+H)

EXAMPLE 66

(2R*)-2-[N-{(1R*,2R*)-5-(2-benzoxazolyl)-2-(4-methoxycarbonylphenyl)-1-methylpentyl}-N-(2-naphthylmethyl)carbamoylmethyl]succinic Acid $^1$H-NMR(CD$_3$COCD$_3$)δ:0.83–0.92 and 0.95(total 3H, m and d, J=6.0 Hz), 1.04–2.30(4H, m), 2.54–3.47(8H, m), 3.86(3H, s), 4.37–4.48 and 4.90–5.40(total 1H, each m), 4.74–4.93(2H, m), 7.28–7.36(2H, m), 7.37–7.67(7H, m), 7.78–7.97(6H, m)

FAB-MS:651(M+H)

EXAMPLE 67

Preparation of Disodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-carboxy-4-hydroxybutanoate (1) Preparation of Tert-butyl (2S,3S)-2-[N-{(1R,2R)-4,4-diethoxy-1-methyl-2-(3,4-methylenedioxyphenyl)butyl}-N-(2-naphthylmethyl)carbamoyl]-5-oxotetrahydrofuran-3-carboxylate 61 mg of N-{(1R,2R)-4,4-diethoxy-1-methyl-2-(3,4-methylenedioxyphenyl)butyl}-2-naphthylmethylamine prepared in the same manner as in Reference Example 1 except that instead of (2RS,3SR,5E)-3-(4-chlorophenyl)-6-(2-naphthyl)-5-hexen-2-ol in Reference Example 1, (2S,3R)-5,5-diethoxy-3-(3,4-methylenedioxyphenyl)pentan-2-ol obtained in Reference Example 10 was used, 35 mg of (2S,3S)-3-tert-butoxycarbonyl-5-oxotetrahydrofuran-2-carboxylic acid obtained in Reference Example 11 and 83 μl of triethylamine, were dissolved in 2ml of chloroform, and 0.5 ml of a chloroform solution containing 34 mg of 2-chloro-1,3-dimethylimidazolinium chloride was added thereto under cooling with ice, followed by stirring at the same temperature for 30 minutes. The reaction solution was poured into water and extracted with ethyl acetate. The extract solution was dried over anhydrous magnesium sulfate. The drying agent was filtered off, and then, the solvent was distilled off under reduced pressure. The residue was purified by silica gel column chromatography (hexane/ethyl acetate=1/3) to obtain 87 mg (yield: 96%) of the above-identified compound as colorless oily substance.

(2) Preparation of Disodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-carboxy-4-hydroxybutanoate Using the N-acylated derivative product of the above step (1), the above-identified compound was prepared in the same manner as in Example 57.

$^1$H-NMR(CD$_3$OD)δ:0.83–1.08(3H, m), 2.30–3.20(6H, m), 4.53–5.10(4H, m), 5.85 and 5.89(total 2H, each s), 5.80–6.95(4H, m), 7.20–8.06(12H, m)

FAB-MS:695(M+H)

EXAMPLE 68

Preparation of Sodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-ethoxycarbonyl-4-hydroxybutanoate (1) Preparation of Ethyl (2S,3S)-2-[N-{(1R,2R,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylate 155 mg of (2S,3S)-2-[N-{(1R,2R,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylic acid prepared by deprotecting the ester of the compound of Example 67(1) with formic acid, 13.5 mg of ethanol and 36.0 mg of 4-dimethylaminopyridine, were dissolved in 2 ml of chloroform, and 57.0 mg of 1-ethyl-3-(3-dimethylaminopropyl)carbodiimide hydrochloride was added thereto, followed by stirring at room temperature overnight. The reaction solution was poured into water and extracted with chloroform. The extract solution was dried over anhydrous magnesium sulfate. The drying agent was filtered off, and then, the solvent was distilled off under reduced pressure. The residue was purified by silica gel column chromatography (hexane/ethyl acetate=2/1) to obtain 123 mg (yield: 76%) of the above-identified compound as slightly yellow oily substance.

(2) Preparation of Sodium (3S,4S)-4-[N-{(1R,2R,4E)-5-(2 -benzoxazolyl)-1-methyl-2-(3,4-methylenedioxyphenyl)-4-pentenyl}-N-(2-naphthylmethyl)carbamoyl]-3-ethoxycarbonyl-4-hydroxybutanoate 120 mg of ethyl (2S,3S)-2-[N-{(1R,2R,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylate was dissolved in a mixed solution of 5 ml of tetrahydrofuran and 2 ml of water, and 182 µl of a 1N sodium hydroxide aqueous solution was added thereto, followed by stirring at room temperature overnight. The solvent was distilled off, and the residue was purified by silica gel column chromatography (chloroform/methanol=20/1→10/1) to obtain 33.0 mg (yield: 26%) of the above-identified compound as a colorless foam.

$^1$H-NMR(CD$_3$OD)δ:0.94 and 1.08(total 3H, each d, J=6.1 Hz and 6.6 Hz), 1.19 and 1.29(total 3H, each t, each J=7.1 Hz), 2.35–3.15(5H, m), 3.38–3.56(1H, m), 4.14 and 4.23 (total 2H, each q, each J=7.1 Hz), 4.48–5.15(4H, m), 5.75 and 6.17(total 2H, each s), 6.50–6.86(3H, m), 7.23–8.00 (12H, m)

FAB-MS:679(M+H)

EXAMPLE 69

Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoic Acid (1) Preparation of Methyl (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxybutanoate 193 mg of tert-butyl (2S,3S)-2-[N-{(1R,2R,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylate obtained in Example 67(1) was dissolved in a mixed solution of 5 ml of tetrahydrofuran and 2 ml of water, and 0.31 ml of a 1N sodium hydroxide aqueous solution was added thereto, followed by stirring at room temperature for 15 hours. The reaction solution was acidified (about pH 4) by an addition of 1N hydrochloric acid and then extracted with ethyl acetate. The extract solution was dried over anhydrous magnesium sulfate. The drying agent was filtered off, and then, the solvent was distilled off under reduced pressure. The obtained carboxylic acid was dissolved in ethyl acetate, and a slightly excess amount of diazomethane was added at room temperature. The solvent was distilled off under reduced pressure, and the residue was purified by silica gel column chromatography (hexane/ethyl acetate—2/1) to obtain 202 mg (yield: quantitative) of the above-identified compound as colorless oily substance.

(2) Preparation of Methyl 4-[N-{(1R,2R,4E)-5-(2-benzoxazolyl)-1-methyl-2-(3,4-methylenedioxyphenyl)-4 -pentenyl}-N-(2-naphthylmethyl)carbamoyl]-3-tert-butoxycarbonyl-4-hydroxy-3-butenoate 36 mg of methyl (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxybutanoate was dissolved in 2 ml of chloroform, and 42 mg of a Dess-Martin reagent (periodenane) was added thereto, followed by stirring at room temperature for 1 hour. The reaction solution was poured into a mixed solution of a saturated sodium hydrogencarbonate aqueous solution and a saturated sodium thiosulfate aqueous solution and extracted with ethyl acetate. The organic layer was washed with a saturated sodium chloride aqueous solution and then dried over anhydrous magnesium sulfate. The drying agent was filtered off, and then, the solvent was distilled off under reduced pressure. The residue was purified by silica gel thin layer chromatography (Kieselgel™60F$_{254}$, Art™5744; hexane/ethyl acetate=3/2) to obtain 14.7 mg (yield: 41%) of the above-identified compound as colorless oily substance.

(3) Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoic Acid 9.9 mg of methyl 4-[N-{(1R,2R,4E)-5-(2-benzoxazolyl)-1-methyl-2-(3,4-methylenedioxyphenyl)-4 -pentenyl}-N-(2-naphthylmethyl)carbamoyl]-3-tert-butoxycarbonyl-4-hydroxy-3-butenoate was dissolved in a mixed solution of 3 ml of tetrahydrofuran and 1 ml of water, and 140 µl of a 1N sodium hydroxide aqueous solution was added thereto, followed by stirring at room temperature for 4 hours. The reaction solution was acidified by an addition of 1N hydrochloric acid and extracted with ethyl acetate. The extract solution was dried over anhydrous magnesium sulfate. The drying agent was filtered off, and then, the solvent was distilled off under reduced pressure. The residue was purified by silica gel thin layer chromatography (Kieselgel™60F$_{254}$, Art™5744; chloroform/methanol=10/1) to obtain 6.9 mg (yield: 70%) of above-identified compound as a colorless foam.

$^1$H-NMR(CDCl$_3$)δ:0.96–1.06(3H, m), 1.41–1.51(9H, m), 2.30–3.29(5H, m), 4.15–4.98(4H, m), 5.88–6.34(3H, m), 6.41–6.74(4H, m), 7.21–7.88(11H, m)

FAB-MS:705(M+H)

Compounds of Examples 70 to 76 were prepared by treating in the same manner as in Example 69 the esters obtained by the same treatment as in Example 68(1) except that instead of the ethanol used in Example 68, the corresponding alcohols were used.

EXAMPLE 70

4-[N-{(1R,2R,4E)-5-(2-benzoxazolyl)-1-methyl-2-(3,4-methylenedioxyphenyl)-4-pentenyl}-N-(2 naphthylmethyl)carbamoyl]-4-hydroxy-3-methoxycarbonyl-3-butenoic Acid $^1$H-NMR(CDCl$_3$)δ:0.82–1.07(3H, m), 1.91–3.37(5H, m), 3.62–5.01(7H, m), 5.89–6.32(3H, m), 6.48–6.79(4H, m), 7.23–7.89(11H, m)
FAB-MS:663(M+H)

EXAMPLE 71

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-isopropoxycarbonyl-3-butenoic Acid $^1$H-NMR(CDCl$_3$)δ:0.98–1.07(3H, m), 1.14–1.32(6H, m), 2.32–3.67(5H, m), 4.18–5.21(5H, m), 5.89–6.34(3H, m), 6.41–6.71(4H, m), 7.21–7.89(11H, m)
FAB-MS:691(M+H)

EXAMPLE 72

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-cyclohexyloxycarbonyl-4-hydroxy-3-butenoic Acid $^1$H-NMR(CDCl$_3$)δ:0.85–1.08(3H, m), 1.13–1.90(10H, m), 2.23–3.66(5H, m), 4.17–5.01(5H, m), 5.89–6.32(3H, m), 6.42–6.75(4H, m), 7.21–7.90(11H, m)
FAB-MS:731(M+H)

EXAMPLE 73

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(2-methoxyethoxy)carbonyl-3-butenoic Acid $^1$H-NMR(CDCl$_3$)δ:0.94–1.10(3H, m), 2.27–3.40(8H, m), 3.54–3.69(2H, m), 4.03–5.00(6H, m), 5.89–6.31(3H, m), 6.49–6.78(4H, m), 7.24–7.89(11H, m)
FAB-MS:707(M+H)

EXAMPLE 74

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-benzyloxycarbonyl-4-hydroxy-3-butenoic Acid $^1$H-NMR(CDCl$_3$)δ:0.83–1.06(3H, m), 2.29–3.40(5H, m), 3.97–4.99(4H, m), 5.14–5.30(2H, m), 5.88–6.34(3H, m), 6.42–6.77(4H, m), 7.20–7.84(16H, m)
FAB-MS:739(M+H)

EXAMPLE 75

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-cyclopentyloxycarbonyl-4-hydroxy-3-butenoic Acid $^1$H-NMR(CDCl$_3$)δ:0.97–1.09(3H, m), 1.50–1.90(8H, m), 2.30–3.20(5H, m), 4.20–5.00(4H, m), 5.18–5.35(1H, m), 5.89–5.92(2H, m), 6.04–6.32(1H, m), 6.45–6.75(4H, m), 7.23–7.88(11H, m)
FAB-MS:717(M+H)

EXAMPLE 76

4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(3-tetrahydrofuranyloxycarbonyl)-3-butenoic Acid $^1$H-NMR(CDCl$_3$)δ:0.80–1.10(3H, m), 2.00–3.70(7H, m), 3.70–4.00(4H, m), 4.00–5.00(4H, m), 5.40–5.50(1H, m), 5.88 and 5.93(total 2H, each s), 6.00–6.70(5H, m), 7.20–7.90(11H, m)
FAB-MS:705(M+H)

EXAMPLE 77

Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(2-hydroxy-1-hydroxymethylethoxycarbonyl)-3-butenoic Acid Instead of ethanol used in Example 68, 1,3-bis(tert-butyldimethylsilyloxy)-2-propanol was used, and the obtained ester was subjected to the same reaction as in Example 69, followed by deprotecting the silyl group, to obtain the above-identified compound.

$^1$H-NMR(CDCl$_3$)δ:0.80–1.00(3H, m), 2.20–5.00(14H, m), 5.85–5.95(2H, m), 6.00–6.80(5H, m), 7.20–7.90(11H, m)
FAB-MS:723(M+H)

EXAMPLE 78

Preparation of 3-allyloxycarbonyl-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-butenoic Acid 69 mg of disodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-carboxy-4-hydroxybutanoate obtained in Example 67, was dissolved in 3 ml of dimethylformamide, and 19 µl of allyl bromide was added thereto, followed by stirring for 6 hours. Then, 19 µl of allyl bromide was additionally added, followed by further stirring for 15 hours. The reaction solution was poured into water, extracted with ethyl ether and then dried over anhydrous magnesium sulfate. The drying agent was filtered off, and then, the solvent was distilled off under reduced pressure. The residue was purified by silica gel column chromatography (hexane/ethyl acetate=3/2). The obtained diallyl ester was treated in the same manner as in Example 69(2) and (3) to obtain 17 mg (yield: 25%) of the above-identified compound as colorless oily substance.

$^1$H-NMR(CDCl$_3$)δ:0.96–1.07(3H, m), 2.30–3.68(5H, m), 4.16–5.40(8H, m), 5.71–6.71(8H, m), 7.20–7.89(11H, m)
FAB-MS:689(M+H)

EXAMPLE 79

Preparation of 4-[N-{(1R,2R,4E)-5-(2-benzoxazolyl)-2-(3,4-methylenedioxyphenyl)-1-methyl-4-pentenyl}-N-(2-naphthylmethyl)carbamoyl]-3-carboxymethylcarbonyl-4-hydroxy-3-butenoic Acid The above-identified compound was obtained as white solid by conducting the same reaction as in Example 78 by using tert-butyl bromoacetate and disodium (3RS,4SR)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-carboxy-4-hydroxybutenoate obtained in the same manner as in Example 69 except that instead of (2S,3S)-3-tert-butoxycarbonyl-5-oxotetrahydrofuran-2-carboxylic acid in Example 67, (2RS,3SR)-3-tert-butoxycarbonyl-5-oxotetrahydrofuran-2-carboxylic acid obtained in Reference Example 14, was used.

$^1$H-NMR(CD$_3$OD)δ:0.95–1.13(3H, m), 2.00–2.69(5H, m), 4.02–5.60(6H, m), 5.80–6.80(7H, m), 7.22–8.10(11H, m).

FAB-MS:729(M+Na)

EXAMPLE 80

Preparation of 5-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-ethoxycarbonyl-5-hydroxy-4-pentenoic Acid (1) Preparation of Ethyl 5-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-ethoxycarbonyl-5-hydroxypentanoate N-{(1R,2R)-4,4-diethoxy-1-methyl-2-(3,4-methylenedioxyphenyl)butyl}-2-naphthylmethylamine obtained in the same manner as in Reference Example 1 except that instead of (2RS,3SR,5E)-3-(4-chlorophenyl)-6-(2-naphthyl)-5-hexen-2-ol in Reference Example 1, (2S,3R)-5,5-diethoxy-3-(3,4-methylenedioxyphenyl)pentan-2-ol was used, and 2,4-diethyl 1-acetoxy-1,2,4-butanetricarboxylate obtained in Reference Example 13, were subjected to a condensation reaction in the same manner as in Example 67(1), followed by the same treatment as in Example 57(2) and (3), to obtain ethyl 5-acetoxy-5-[N-{(1R,2R,4E)-5-(2-benzoxazolyl)-1-methyl-2-(3,4-methylenedioxyphenyl)-4-petenyl}-N-(2-naphthylmethyl)carbamoyl]-4-ethoxycarbonylpentanoate. 71 mg of such an ethyl ester was dissolved in 2 ml of ethanol, and 7 mg of sodium ethoxide was added thereto, followed by stirring at room temperature for one hour. The reaction solution was poured into water and extracted with ethyl acetate. Then, the organic layer was dried over anhydrous magnesium sulfate. The drying agent was filtered off, and then, the solvent was distilled off under reduced pressure. The residue was purified by silica gel column chromatography (hexane/ethyl acetate=2/1) to obtain 23 mg (yield: 34%) of the above-identified compound.

(2) Preparation of 5-N-{(1R,2R,4E)-5-(2-benzoxazolyl)-1-methyl-2-(3,4-methylenedioxyphenyl)-4-pentenyl}-N-(2-naphthylmethyl)carbamoyl]-4-ethoxycarbonyl-5-hydroxy-4-pentenoic Acid The compound of the above step (1) was treated in the same manner as in Example 69(2) and (3) to obtain the above-identified compound as colorless oily substance.

$^1$H-NMR(CDCl$_3$)δ:0.97–1.09(3H, m), 1.22–1.32(3H, m), 2.14–2.95(7H, m), 4.19–5.01(6H, m), 5.89–6.74(7H, m), 7.22–7.90(11H, m)

FAB-MS:691(M+H)

EXAMPLE 81

Preparation of 5-N-{(1R,2R,4E)-5-(2-benzoxazolyl)-1-methyl-2-(3,4-methylenedioxyphenyl)-4-pentenyl}-N-(2-naphthylmethyl)carbamoyl]-4-tert-butoxycarbonyl-5-hydroxy-4-pentenoic Acid Instead of 2,4-diethyl 1-acetoxy-1,2,4-butane tricarboxylate in Example 80, 2,4-di-tert-butyl 1-acetoxy-1,2,4-butane tricarboxylate (synthesized in the same manner as in Reference Example 13 using di-tert-butyl glutarate as the starting material) was used and treated in the same manner as in Example 80 to obtain tert-butyl 5-acetoxy-5-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-tert-butoxycarbonylpentanoate. Then, using an aqueous sodium hydroxide solution, the acetoxy group was converted to a hydroxyl group, followed by the same reaction as in Example 80(2) to obtain the above-identified compound.

$^1$H-NMR(CDCl$_3$)δ:0.80–1.05(3H, m), 1.22–1.52(9H, m), 1.80–2.90(7H, m), 4.10–5.38(6H, m), 5.88–6.74(7H, m), 7.25–7.92(11H, m)

FAB-MS:719(M+H)

EXAMPLE 82

Preparation of 4-N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-hydroxymethyl-3-butenoic Acid (1) Preparation of (3S,4S)-4-N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxymethyl-2-oxotetrahydrofuran 95 mg of (2S,3S)-2-[N-{(1R,2R)-4,4-diethoxy-1-methyl-2-(3,4-methylenedioxyphenyl)butyl}-N-(2-naphthylmethyl)carbamoyl]-5-oxotetrahydrofuran-3-carboxylic acid obtained by deprotecting the ester of the compound of Example 67(1) with formic acid, was dissolved in 3 ml of tetrahydrofuran, and 42 µl of triethylamine and 39 µl of isobutyl chloroformate were added thereto under cooling with ice. Stirring was continued at the same temperature for 30 minutes, and then 38 mg of sodium borohydride was added, followed by stirring at room temperature for 30 minutes. The reaction solution was poured into water and extracted with ethyl acetate. Then, the organic layer was dried over anhydrous magnesium sulfate. The drying agent was filtered off, and then, the solvent was distilled off under reduced pressure. The residue was purified by silica gel thin layer chromatography (Kieselgel™60F$_{254}$, Art™5744; hexane/ethyl acetate=1/2) to obtain 39 mg (yield: 42%) of the above-identified compound as colorless oily substance.

(2) Preparation of (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-tert-butyldimethylsilyloxymethyl-2-oxotetrahydrofuran 56 mg of (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxymethyl-2-oxotetrahydrofuran was dissolved in 3 ml of dimethylformamide, and 16 mg of imidazole and 27 mg of tert-butyldimethylsilyl chloride were added thereto, followed by stirring at room temperature for 18 hours. The reaction solution was poured into water and extracted with ethyl ether. The extract solution was dried over anhydrous magnesium sulfate. The drying agent was filtered off, and then, the solvent was distilled off under reduced pressure. The residue was purified by silica gel column chromatography (hexane/ethyl acetate=2/1) to obtain 39 mg (yield: 75%) of the above-identified compound as colorless oily substance.

(3) Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-hydroxymethyl-3-butenoic Acid Using the compound obtained in the above step (2), the same reaction as in Example 69 was carried out, followed by deprotecting the silyl group to obtain the above-identified compound.

$^1$H-NMR(CDCl$_3$)δ:1.01–1.13(3H, m), 2.19–5.22(11H, m), 5.71–6.79(7H, m), 7.19–7.88(11H, m).

FAB-MS:635(M+Na)

EXAMPLE 83

Preparation of 4-[N-{(1RS,2RS,5E)-6-(2-benzoxazolyl)-1-methyl-2-(3,4-methylenedioxyphenyl)-5-hexenyl}-N-(2-naphthylmethyl)carbamoyl]-3-tert-butoxycarbonyl-4-hydroxy-3-butenoic Acid N-[(1RS,2RS)-5-(1,3-dioxolan-2-yl)-1-methyl-2-(3,4-methylenedioxyphenyl)butyl]-2-naphthylmethylamine obtained in the same manner as in Reference Example 1 and (2RS,3RS)-3-tert-butoxycarbonyl-5-oxotetrahydrofuran-2-carboxylic acid obtained in Reference Example 4 were used and subjected to a condensation reaction in the same manner as in Example 67(1) to obtain an acylated product, which was treated in the same manner as in Example 27(2) and (3) to obtain tert-butyl (4RS,5RS)-5-[N-{(1RS,2RS,5E)-6-(2-benzoxazolyl)-1-methyl-2-(3,4-methylenedioxyphenyl)-5-hexenyl}-N-(2-naphthylmethyl)carbamoyl]-2-oxotetrahydrofuran-4-carboxylate. By using the tert-butyl ester, the above-identified compound was obtained in the same manner as in Example 69.

$^1$H-NMR(CDCl$_3$)δ:0.80–1.10(3H, m), 1.40–1.50(9H, m), 1.50–2.00(4H, m), 2.60–3.60(3H, m), 4.10–5.00(4H, m), 5.80–7.00(7H, m), 7.20–7.90(11H, m).

FAB-MS:718(M+H)

EXAMPLE 84

Preparation of (2S*,3R*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butane tricarboxylic Acid and (2R*,3S*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butane tricarboxylic Acid (1) Preparation of Triethyl (2RS,3SR)-4-[N-{(1R,2R)-4,4-diethoxy-1-methyl-2-(3,4-methylenedioxyphenyl)butyl}-N-(2-naphthylmethyl)carbamoyl]-1,2,3-butanetricarboxylate 150 mg of N-{(1R,2R)-4,4-diethoxy-1-methyl-2-(3,4-methylenedioxyphenyl)butyl}-2-naphthylmethylamine obtained in the same manner as in Reference Example 1 using (2S,3R)-5,5-diethoxy-3-(3,4-methylenedioxyphenyl)pentan-2-ol obtained in Reference Example 10 instead of the (2RS,3SR,5E)-3-(4-chlorophenyl)-6-(2-naphthyl)-5-hexen-2-ol in Reference Example 1, 120 mg of 2,3,4-triethyl (2RS,3SR)-1,2,3,4-butanetetracarboxylate obtained in Reference Example 12, and 205 μl of triethylamine, were dissolved in chloroform, and 1 ml of a chloroform solution containing 83 mg of 2-chloro-1,3-dimethylimidazolium chloride was added thereto under cooling with ice, followed by stirring at the same temperature for 30 minutes and further by stirring at room temperature for 30 minutes. The reaction solution was poured into water and extracted with ethyl acetate. The extract solution was washed with a saturated sodium hydrogencarbonate aqueous solution and then dried over anhydrous magnesium sulfate. The drying agent was filtered off, and then, the solvent was distilled off under reduced pressure. The residue was purified by silica gel column chromatography (hexane/ethyl acetate=5/1→2/1) to obtain 200 mg (yield: 80%) of the above-identified compound as colorless oily substance.

(2) Preparation of (2S*,3R*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butane tricarboxylic Acid and (2R*,3S*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butane tricarboxylic Acid 196 mg of the N-acylated product obtained in the above step (1) was treated in the same manner as in Example 27 to obtain triethyl (2RS,3SR)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butane tricarboxylate, and the obtained ester was separated into two types of compounds which are in the relation of diastereomers, by means of high performance liquid chromatography (Senshu Pak™, Silica-5301-N; hexane/ethyl acetate=2/1), whereby the esters of the above-identified compounds named as the (2S*,3R*)-isomer (the component eluting first in the high performance liquid chromatography) and the (2R*,3S*)-isomer (the component eluting later in the high performance liquid chromatography) were obtained in amounts of 85 mg (yield: 39%) and 97 mg (yield: 44%), respectively, as colorless oily substances. Then, they were separately dissolved in tetrahydrofuran, and a solution having 30 equivalents of lithium hydroxide monohydrate dissolved in water, was added thereto, followed by stirring at room temperature for 8 hours. Then, tetrahydrofuran was distilled off under reduced pressure to obtain uniform aqueous solutions, and stirring was further continued for 2 days. The reaction solutions were acidified by an addition of 1N hydrochloric acid and extracted with ethyl acetate. Then, the extract solutions were dried over anhydrous sodium sulfate. The drying agent was filtered off, and then, the solvent was distilled off under reduced pressure. The residues were purified by medium pressure liquid chromatography (Lobar column™, size B, RP-8, manufactured Merck Co.; acetonitrile/0.1% trifluoroacetic acid aqueous solution=1/1), followed by crystallization from hexane/ethyl acetate to obtain 53 mg (yield: 69%) of the above-identified compound named as the (2S*,3R*)-isomer and 59 mg (yield: 70%) of the above-identified compound named as the (2R*,3S*)-isomer, respectively, as white powders.

(2S*,3R*)-isomer $^1$H-NMR(CD$_3$OD)δ:0.80–1.00(3H, m), 2.30–3.60(9H, m), 4.30–5.00(3H, m), 5.80–6.00(2H, m), 6.10–6.40(1H, m), 6.60–6.90(4H, m), 7.20–8.00(11H, m)

FAB-MS:693(M+H)

(2R*,3S*)-isomer $^1$H-NMR(CD$_3$OD)δ:0.80–1.05(3H, m), 2.30–3.60(9H, m), 4.30–5.00(3H, m), 5.85–6.00(2H, m), 6.20–6.40(1H, m), 6.50–6.90(4H, m), 7.20–7.90(11H, m)

FAB-MS:693(M+H)

REFERENCE EXAMPLE 1

Preparation of N-{(1RS,2RS,4E)-2-(4-chlorophenyl)-1-methyl-5-(2-naphthyl)-4-pentenyl}-2-naphthylmethylamine (1) Preparation of (E)-3-(4-chlorophenyl)-6-(2-naphthyl)-5-hexen-2-one 2.56 g of p-chlorophenylacetone was dissolved in a mixed solution of 5 ml of dimethylformamide and 5 ml of benzene, and a dimethylformamide 8 ml/benzene 8 ml solution containing 0.62 g of 60% oily sodium hydride and 3.50 g of (E)-3-(2-naphthyl)-2-propenyl bromide, was added under cooling with ice with stirring, followed by stirring at room temperature for 2 hours. The reaction solution was acidified by an addition of 1N hydrochloric acid and extracted by an addition of water and ethyl ether. Then, the organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=5/1) to obtain 3.70 g of the above-identified compound.

(2) Preparation of (2RS,3SR,5E)-3-(4-chlorophenyl)-6-(2-naphthyl)-5-hexen-2-ol 4.78 g of (E)-3-(4-chlorophenyl)-6-(2-naphthyl)-5-hexen-2-one was dissolved in 30 ml of tetrahydrofuran, and 14.3 ml of a 1M tetrahydrofuran solution of lithium tri-sec-butyl borohydride was added at −78° C. under cooling with stirring, followed by stirring at the same temperature for 2 hours. To the reaction solution, 10 ml of a 2N sodium hydroxide aqueous solution was added under cooling with ice with stirring, and then, 15 ml of a 30% hydrogen peroxide aqueous solution was gradually dropwise added, followed by stirring at room temperature for one hour. The reaction solution was extracted by an addition of ethyl ether and water. The organic layer was washed with a saturated sodium thiosulfate aqueous solution and a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=15/1→5/1) to obtain 4.06 g of the above-identified compound.

(3) Preparation of (1RS,2RS,4E)-2-(4-chlorophenyl)-1-methyl-5-(2-naphthyl)-4-pentenylamine 4.06 g of (2RS,3SR,5E)-3-(4-chlorophenyl)-6-(2-naphthyl)-5-hexen-2-ol was dissolved in 30 ml of tetrahydrofuran, and 4.77 g of triphenylphosphine, 2.89 ml of diethyl azodicarboxylate and 4.77 g of diphenylphosphoryl azide were added under cooling with ice with stirring, followed by stirring at room temperature for 30 minutes. The reaction solution was evaporated to dryness under reduced pressure. Then, the residue was purified by silica gel column chromatography (hexane/ethyl acetate=50/1→30/1). The obtained azide product was heated and refluxed together with 3.2 g of triphenylphosphine in 100 ml of 10% water-containing tetrahydrofuran. The reaction solution was evaporated to dryness under reduced pressure. Then, the residue was purified by silica gel column chromatography (methylene chloride/methanol=50/1→20/1) to obtain 2.30 g of the above-identified compound.

(4) Preparation of N-{(1RS,2RS,4E)-2-(4-chlorophenyl)-1-methyl-5-(2-naphthyl)-4-pentenyl}-2-naphthylmethylamine 0.75 g of (1RS,2RS,4E)-2-(4-chlorophenyl)-1-methyl-5-(2-naphthyl)-4-pentenylamine was dissolved in 10 ml of methanol, and 0.34 g of 2-naphthoaldehyde was added thereto, followed by stirring at room temperature overnight. To the reaction solution, 10 mg of tetrahydrofuran was added to dissolve the formed precipitate, and 84 mg of sodium borohydride was added thereto, followed by stirring at room temperature for 2 hours. The reaction solution was extracted by an addition of ethyl ether and water. The organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=7/1→3/1) to obtain 0.76 g of the above-identified compound.

The reaction was carried out in the same manner as in Reference Example 1 except that instead of the p-chlorophenylacetone and/or (E)-3-(2-naphthyl)-2-propenylbromide and/or 2-naphthoaldehyde, used as the starting material in the above reaction, the corresponding arylacetone derivative and/or halide and/or arylaldehyde derivative, was used to obtain N-{(1RS,2RS,4E)-2-(4-chlorophenyl)-1-methyl-5-(1-naphthyl)-4-pentenyl}-2-naphthylmethylamine, N-{(1RS,2RS)-2-(4-chlorophenyl)-1-methyl-5-(2-naphthyl)-4-pentyl}-2-naphthylmethylamine, N-{(1RS,2RS)-2-(4-chlorophenyl)-1-methyl-4-(2-naphthoxy)butyl}-2-naphthylmethylamine, N-{(1RS,2RS)-2-(4-chlorophenyl)-1-methyl-4-(2-naphthyl)butyl}-2-naphthylmethylamine, N-{(1RS,2RS)-2-(4-chlorophenyl)-1-methyl-6-(2-naphthyl)hexyl}-2-naphthylmethylamine, N-{(1RS,2RS)-2-(4-chlorophenyl)-1-methyl-5-phenyl-4-pentynyl}-2-naphthylmethylamine, N-{(1RS,2RS,4E)-2-(4-methoxyphenyl)-1-methyl-5-(2-naphthyl)-4-pentenyl}-2-naphthylmethylamine, N-{(1RS,2RS,4E)-2-(4-methylphenyl)-1-methyl-5-(2-naphthyl)-4-pentenyl}-2-naphthylmethylamine, N-{(1RS,2RS,4E)-1-methyl-5-(2-naphthyl)-2-(4-nitrophenyl)-4-pentenyl}-2-naphthylmethylamine, N-{(1RS,2RS,4E)-2-(4-fluorophenyl)-1-methyl-5-(2-naphthyl)-4-pentenyl}-2-naphthylmethylamine, N-{(1RS,2RS,4E)-1-methyl-5-(2-naphthyl)-2-(4-trifluoromethylphenyl)-4-pentenyl}-2-naphthylmethylamine, N-{(1RS,2RS,4E)-1-methyl-5-(2-naphthyl)-2-phenyl-4-pentenyl}-2-naphthylmethylamine, N-{(1RS,2RS,4E)-1-methyl-2-(6-methyl-3-pyridyl)-5-(2-naphthyl)-4-pentenyl}-2-naphthylmethylamine, N-{(1RS,2RS,6E)-2-(4-chlorophenyl)-1-methyl-7-phenyl-6-heptenyl}-2-naphthylmethylamine, N-{(1RS,2RS,6E)-2-(4-chlorophenyl)-1-methyl-7-(2-naphthyl)-6-heptenyl}-2-naphthylmethylamine, N-{(1RS,2RS,4E)-2-(4-chlorophenyl)-1-methyl-5-(2-naphthyl)-4-pentenyl}-3-quinolylmethylamine, N-{(1RS,2RS,4E)-2-(4-chlorophenyl)-1-methyl-5-(2-naphthyl)-4-pentenyl}-3,4-difluorobenzylamine, N-(2-benzoxazolylmethyl)-{(1RS,2RS,4E)-2-(4-chlorophenyl)-1-methyl-5-(2-naphthyl)-4-pentenyl}amine, N-(2-benzo[b]thienylmethyl)-{(1RS,2RS,4E)-2-(4-chlorophenyl)-1-methyl-5-(2-naphthyl)-4-pentenyl}amine, N-{(1RS,2RS,4E)-1-methyl-2-(3,4-methylenedioxyphenyl)-5-(2-naphthyl)-4-pentenyl}-2-naphthylmethylamine, N-{(1RS,2RS)-4,4-diethoxy-1-methyl-2-(3,4-methylenedioxyphenyl)butyl}-2-naphthylmethylamine, N-(2-benzo[b]furanylmethyl)-{(1RS,2RS)-4,4-diethoxy-1-methyl-2-(3,4-methylenedioxyphenyl)butyl}amine, N-(2-benzo[b]thienylmethyl)-{(1RS,2RS)-4,4-diethoxy-1-methyl-2-(3,4-methylenedioxyphenyl)butyl}amine, N-[(1RS,2RS)-4,4-diethoxy-1-methyl-2-{(3,4-bis(methoxycarbonyl)phenyl}butyl]-2-naphthylmethylamine, N-(2-benzo[b]thienylmethyl)-{(1RS,2RS)-4,4-diethoxy-2-(4-methoxycarbonylphenyl)-1-methylbutyl}amine, N-(2-benzo[b]furanylmethyl)-{(1RS,2RS)-4,4-diethoxy-2-(4-methoxycarbonylphenyl)-1-methylbutyl}amine, N-(2-benzo[b]thienylmethyl)-{(1RS,2RS)-2-(4-cyanophenyl)-4,4-diethoxy-1-methylbutyl}amine, N-(5-benzo[b]thienylmethyl)-{(1RS,2RS)-4,4-diethoxy-2-(4-methoxycarbonylphenyl)-1-methylbutyl}amine, N-{(1RS,2RS)-2-(4-chlorophenyl)-4,4-diethoxy-1-methylbutyl}-2- naphthylmethylamine, N-{(1RS,2RS)-2-(4-cyanophenyl)-4,4-diethoxy-1-methylbutyl}-2-naphthylmethylamine, N-{(1RS,2RS)-2-(4-cyanophenyl)-4,4-diethoxy-1-methylbutyl}-2-naphthylmethylamine, N-{(1RS,2RS)-4,4-diethoxy-2-(4-methoxycarbonylphenyl)-1-methylbutyl}-2-naphthylmethylamine, N-{(1RS,2RS,4E)-2-(4-methoxycarbonylphenyl)-1-methyl-5-(2-naphthyl)-4-pentenyl}-2-naphthylmethylamine and N-[(1RS,2RS)-5-(1,3-dioxolan-2-yl)-1-methyl-2-(3,4-methylenedioxyphenyl)butyl]-2-naphthylmethylamine.

REFERENCE EXAMPLE 2

Preparation of N-{(1S*,2S*,4E)-2-(4-chlorophenyl)-1-methyl-5-(2-naphthyl)-4-pentenyl}-2-naphthylmethylamine 7.0 g of p-chlorophenyl acetic acid was dissolved in 14 ml of thionyl chloride, followed by heating at 60° C. for 2 hours. Then, excess thionyl chloride was distilled off under reduced pressure. The residue was dissolved in 5 ml of tetrahydrofuran, and this solution was gradually dropwise added to a solution prepared previously by stirring 4.4 g of (4S)-(−)-isopropyl-2-oxazolizinone and 23.2 ml of a 1.6M hexane solution of n-butyl lithium in 50 ml of tetrahydrofuran at −78° C. for one hour. After the dropwise addition, stirring was continued at the same temperature for 30 minutes. The reaction solution was extracted by an addition of water and ethyl ether, and the organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography to obtain 6.02 g of (4S)-N-(p-chlorophenylacetyl)-4-isopropyl-2-oxazolizinone.

6.00 g of the 2-oxazolizinone thus obtained was dissolved in 120 ml of tetrahydrofuran, and 23.4 ml of a 1M tetrahydrofuran solution of sodium bis(trimethylsilyl)amide was added under cooling to −78° C. with stirring, followed by stirring for one hour. Then, while stirring the mixture at −78° C., 21 ml of hexamethylphosphoric triamide and a tetrahydrofuran solution (15 ml) of 6.60 g of 3-(2-naphthyl)-2-propenylbromide were added, followed by stirring at the same temperature for one hour. The reaction solution was extracted by an addition of water and ethyl acetate, and the organic layer was washed with a saturated sodium chloride aqueous solution and then dried over anhydrous magnesium sulfate. The drying agent was filtered off, and then, the solvent was distilled off under reduced pressure. The residue was roughly purified by silica gel column chromatography (hexane/methylene chloride=1/1) and purified by medium pressure liquid chromatography (hexane/methylene chloride=2/1) to obtain 3.08 g of (4R)-N-{(2S*,4E)-2-(4-chlorophenyl)-5-(2-naphthyl)-4-pentenoyl}-4-isopropyl-2-oxazolizinone (component eluting first in the medium pressure liquid chromatography) and 3.25 g of (4R)-N-{(2R*,4E)-2-(4-chlorophenyl)-5-(2-naphthyl)-4-pentenoyl}-4-isopropyl-2-oxazolizinone (component eluting later in the medium pressure liquid chromatography) which are named as the (2S*)-isomer and the (2R*)-isomer for the sake of convenience.

3.08 g of the (2S*)-isomer thus obtained was dissolved in a mixed solution of 130 ml of tetrahydrofuran and 38 ml of water, and 4.9 ml of a 30% hydrogen peroxide aqueous solution was added under cooling with ice with stirring. Then, 0.67 g of lithium hydroxide monohydrate was further added thereto, followed by stirring for one hour under cooling with ice. Sodium sulfite was added to the reaction solution to decompose hydrogen peroxide. Then, 2N hydrochloric acid and ethyl acetate were added thereto for extraction. The organic layer was washed with a saturated sodium chloride aqueous solution and then dried over anhydrous magnesium sulfate. The drying agent was filtered off, and then, the solvent was distilled off under reduced pressure. The residue was dissolved in 51 ml of tetrahydrofuran, and 1.59 g of 1,1'-carbonyldiimidazole was added thereto, followed by stirring at room temperature for one hour. Then, 4.94 g of N,O-dimethylhydroxylamine and 8.8 ml of N,N-diisopropylethylamine were added thereto, followed by stirring at room temperature for 2 hours. The reaction solution was extracted by an addition of 1N hydrochloric acid and ethyl ether, and the organic layer was washed with a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=5/1) to obtain 2.70 g of (2S*,4E)-2-(4-chlorophenyl)-5-(2-naphthyl)-4-pentenoic acid N,O-dimethylhydroxyamide.

2.70 g of the hydroxyamide thereby obtained was dissolved in 83 ml of ethyl ether, and 9.5 ml of a 1.5M ethyl ether solution of methyl lithium was added under cooling with ice with stirring, followed by stirring at the same temperature for 30 minutes. The reaction solution was extracted by an addition of water and ethyl acetate, followed by post-treatment by a conventional method. Then, purification was conducted by silica gel column chromatography (hexane/ethyl acetate=5/1) to obtain 1.98 g of (3S*,5E)-3-(4-chlorophenyl)-6-(2-naphthyl)-5-hexen-2-one.

1.95 of the ketone thus obtained was dissolved in 62 ml of tetrahydrofuran, and 7.0 ml of a 1M tetrahydrofuran solution of lithium tri-sec-butyl borohydride was added under cooling to −78° C. with stirring, followed by stirring at the same temperature for 30 minutes. To the reaction solution, 20 ml of a 0.5N sodium hydroxide aqueous solution was added, and then 10 ml of a 30% hydrogen peroxide aqueous solution was dropwise added thereto. After the dropwise addition, the mixture was stirred at room temperature for 30 minutes. The reaction solution was extracted by an addition of water and ethyl acetate, followed by conventional post-treatment. Then, purification was conducted by medium pressure liquid chromatography (hexane/ethyl acetate=5/1) to obtain 1.91 g of (2S*,3S*,5E)-3-(4-chlorophenyl)-6-(2-naphthyl)-5-hexen-2-ol.

1.81 g of the alcohol thus obtained was dissolved in 18 ml of tetrahydrofuran, and 2.11 g of triphenylphosphine, 1.27 ml of diethyl azodicarboxylate and 1.73 g of diphenylphosphoryl azide were added under cooling with ice under stirring, followed by stirring at room temperature for 30 minutes. The reaction solution was evaporated to dryness under reduced pressure, and then the residue was purified by silica gel column chromatography (hexane/ethyl acetate=50/1) to obtain 1.59 g of (4S*,5S*,5E)-5-azide-4-(4-chlorophenyl)-1-(2-naphthyl)-1-hexene.

1.59 g of the azide compound thus obtained was dissolved in a mixed solution of 36 ml of tetrahydrofuran and 3 ml of water, and 1.3 g of triphenylphosphine was added thereto, followed by heating and refluxing for one hour. The reaction solution was left to cool to room temperature and then extracted by an addition of ethyl ether and water, followed by post-treatment in accordance with a conventional method. Then, purification was conducted by silica gel column chromatography (methylene chloride/methanol=50/1→30/1) to obtain 0.88 g of 1S*,2S*,4E)-2-(4-chlorophenyl)-1-methyl-5-(2-naphthyl)-4-pentenylamine.

0.84 g of the amine compound thus obtained was dissolved in 25 ml of methanol, and 0.43 g of 2-naphthoaldehyde was added thereto, followed by heating for 30 minutes under reflux. The reaction solution was left to cool to room temperature, and then 10 ml of tetrahydrofuran was added to dissolve the precipitate. Then, 0.21 g of sodium borohydride was added thereto, followed by stirring at room temperature for 30 minutes. The reaction solution was extracted by an addition of water and ethyl ether, then post-treated in accordance with a conventional method and purified by medium pressure liquid chromatography (hexane/ethyl acetate=10/1→4/1) to obtain 0.76 g of the above-identified compound, $[\alpha]_D^{20}$+23.8° (c 0.992, chloroform).

Using (4R)-N-{(2R*,4E)-2-(4-chlorophenyl)-5-(2-naphthyl)-4-pentenoyl}-4-isopropyl-2-oxazolizinone obtained as an intermediate by the above reaction, the reaction was carried out in the same manner as in Reference Example 2 to obtain N-{(1R*,2R*,4E)-2-(4-chlorophenyl)-1-methyl-5-(2-naphthyl)-4-pentenyl}-2-naphthylmethylamine, $[\alpha]_D^{20}$−23.5° (c 1.012, chloroform), which is in a relationship of a mirror image isomer to the above-identified compound.

REFERENCE EXAMPLE 3

Preparation of 1,2-di-tert-butyl 1,2,3-propanetricarboxylate and Its Optical Resolution 13.1 ml of a 1.5M cyclohexane solution of lithium diisopropylamide was dissolved in 10 ml of tetrahydrofuran, and a tetrahydrofuran solution (10 ml) containing 2.96 g of benzyl acetate was added under cooling to −70° C. with stirring, followed by stirring at the same temperature for 30 minutes. Then, a tetrahydrofuran solution (10 ml) containing 2.96 g of di-tert-butyl maleate, was dropwise added thereto, followed by stirring at the same temperature for 30 minutes. The reaction solution was extracted by an addition of 20 ml of water and 50 ml of ethyl ether. The organic layer was separated, then washed with a saturated sodium chloride aqueous solution and dried over anhydrous magnesium sulfate. Then, the solvent was distilled off under reduced pressure. The residue was dissolved in 50 ml of dioxane, and 0.4 g of a 10% palladium carbon catalyst was added thereto, followed by catalytic reduction for 20 hours at room temperature under hydrogen atmospheric pressure. The catalyst was filtered off, and then, the solvent was distilled off under reduced pressure. The residue was treated with hexane, whereupon the precipitate thereby obtained was collected by filtration and then dried to obtain 3.02 g of the above-identified compound as colorless crystalline powder, mp 55°–57° C. 12.97 g of the di-tert-butyl ester thus obtained and 13.24 g of cinchonidine was dissolved under heating in 1 l of carbon tetrachloride. Then, seed crystals were added thereto, and the mixture was left to stand at room temperature for 24 hours. The crystals were collected by filtration and then again dissolved under heating in 1 l of carbon tetrachloride, and seed crystals were added thereto, and the mixture was left to stand for 24 hours. This operation was further repeated twice to obtain 6.66 g of a cinchonidine salt of the above-identified compound, which is named as the (S*)-isomer for the sake of convenience, $[\alpha]_D^{20}$−62.7° (c 1.0, chloroform).

The cinchonidine salt thus obtained was dissolved in a mixed solution of ethyl ether and 1N hydrochloric acid under cooling with ice, and the organic layer was separated and then post-treated in accordance with a conventional method to obtain the (S*)-isomer of the above-identified compound as colorless oily substance, $[\alpha]_D^{20}$+4.44° (c 0 92, chloroform).

The fraction containing a large amount of the other mirror image isomer obtained in the above optical resolution operation, was converted to a free acid, and then, the same operation was carried out in isopropyl ether using quinine, whereby the mirror image isomer named as the (R*)-isomer for the sake of convenience, was obtained.

REFERENCE EXAMPLE 4

Preparation of (2RS,3RS)-3-tert-butoxycarbonyl-5-oxotetrahydrofuran-2-carboxylic Acid (1) Preparation of (2RS,3SR)-2-diphenylmethoxycarbonyl-5-oxotetrahydrofuran-3-carboxylic Acid 262 mg of (2RS,3SR)-5-oxotetrahydrofuran-2,3-dicarboxylic acid was dissolved in 5 ml of acetone, and 91 mg of diphenyldiazomethane was added thereto, followed by stirring at room temperature for 20 minutes. The reaction solution was evaporated to dryness under reduced pressure. The residue was purified by silica gel column chromatography (chloroform/methanol=100/1→10/1) to obtain 163 mg of the above-identified compound as white powder.

(2) Preparation of 3-tert-butyl 2-diphenylmethyl (2RS,3RS)-5-oxotetrahydrofuran-2,3-dicarboxylate 163 mg of (2RS,3SR)-2-diphenylmethoxycarbonyl-5-oxotetrahydrofuran-3-carboxylic acid, 59 mg of 4-dimethylaminopyridine and 36 mg of tert-butanol, were dissolved in 4 ml of methylene chloride, and 110 mg of 1-ethyl-3-(3-dimethylaminopropyl)carbodiimide hydrochloride was added thereto, followed by stirring at room temperature for 13 hours. The reaction solution was diluted with methylene chloride, then sequentially washed with a 10% citric acid aqueous solution, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=10/1) to obtain 148 mg of the above-identified compound as colorless oily substance.

(3) Preparation of (2RS,3RS)-3-tert-butoxycarbonyl-5-oxotetrahydrofuran-2-carboxylic Acid 148 mg of 3-tert-butyl 2-diphenylmethyl (2RS,3RS)-5-oxotetrahydrofuran-2,3-dicarboxylate was dissolved in 4 ml of ethyl acetate, and 15 mg of a 10% palladium-carbon catalyst was added thereto, followed by catalytic reduction for 15 hours at room temperature under hydrogen atmospheric pressure. The catalyst was filtered off, and then, the solvent was distilled off under reduced pressure. The residue was washed with benzene to obtain 66 mg of above-identified compound as white crystalline powder.

REFERENCE EXAMPLE 5

Preparation of 2,2,3-tri-tert-butyl 1,2,2,3-propanetetracarboxylate 1.2 g of 60% oily sodium hydride was suspended in 30 ml of dimethylformamide, and 3 ml of a dimethylformamide solution containing 3.0 g of di-tert-butyl malonate was dropwise added thereto under cooling with ice with stirring. After stirring at the same temperature for 30 minutes, 3 ml of a dimethylformamide solution containing 2.7 g of tert-butyl bromoacetate, was dropwise added thereto, followed by stirring at room temperature for 2 hours. Then, 3 ml of a dimethylformamide solution containing 3.5 g of benzyl bromoacetate was added thereto, followed by further stirring at room temperature for 2 hours. Then, a saturated ammonium chloride aqueous solution was added to the reaction solution, and the mixture was extracted with ethyl ether. The ether layer was washed with a saturated sodium chloride aqueous solution and then dried over anhydrous magnesium sulfate. The drying agent was filtered off, and then, the solvent was distilled off under reduced pressure. The residue was dissolved in 75 ml of ethanol, and 350 mg of a 10% palladium-carbon catalyst was added thereto, followed by catalytic reduction for 12 hours at room temperature under hydrogen atmospheric pressure. The catalyst was filtered off, and then, the solvent was distilled off under reduced pressure. The residue was purified by silica gel column chromatography (hexane/ethyl acetate=5/1→chloroform/methanol=10/1) to obtain 2.96 g of the above-identified compound as colorless oily substance.

REFERENCE EXAMPLE 6

Preparation of 1,2,3-tri-tert-butyl 1,1,2,3-propanetetracarboxylate 30 mg of 60% oily sodium hydride was suspended in 4 ml of tetrahydrofuran, and 1 ml of a tetrahydrofuran solution containing 186 mg of benzyl tert-butyl malonate was dropwise added under cooling with ice with stirring, followed by stirring at the same temperature for 20 minutes. Likewise, 1 ml of a tetrahydrofuran solution containing 143 mg of di-tert-butyl maleate was dropwise added under cooling with ice with stirring, followed by stirring at the same temperature for 3 hours and then at room temperature for 2 hours and further at 60° C. for one hour. A saturated ammonium chloride aqueous solution was added to the reaction solution, and the mixture was extracted with ethyl acetate. Then, the ethyl acetate layer was washed with a saturated sodium chloride aqueous solution and dried over anhydrous magnesium sulfate. The drying agent was filtered off, and then, the solvent was distilled off under reduced pressure. The residue was dissolved in 3 ml of ethanol, and 30 mg of a 10% palladium-carbon catalyst was added thereto, followed by catalytic reduction for 12 hours at room temperature under hydrogen atmospheric pressure. The catalyst was filtered off, and then, the solvent was distilled off under reduced pressure. The residue was purified by silica gel column chromatography (chloroform/methanol=10/1) to obtain 207 mg of the above-identified compound as colorless oily substance.

REFERENCE EXAMPLE 7

Preparation of 1,2-diethyl (1S,2R)-1-acetoxy-1,2,3-propanetricarboxylate (1) Preparation of 3-benzyl 1,2-diethyl (1S,2R)-1-acetoxy-1,2,3-propanetricarboxylate 5.2 ml of a 2M cyclohexane solution of lithium diisopropylamide was dissolved in 10 ml of tetrahydrofuran, and 5 ml of a tetrahydrofuran solution containing 2 g of (S)-malic acid diethyl ester, was dropwise added at −78° C. under a nitrogen atmosphere. The reaction solution was gradually heated to −20° C. over a period of one hour and then again cooled to −78° C. Then, 5 ml of a tetrahydrofuran solution containing 1.32 g of benzyl bromoacetate was added thereto, followed by stirring for one hour at −78° C. to −20° C. 10 ml of a 1N citric acid aqueous solution was added thereto and extracted with ethyl ether. Then, the ether layer was washed with a saturated sodium chloride aqueous solution and dried over anhydrous sodium sulfate. The drying agent was filtered off, and then, the solvent was distilled off under reduced pressure. The residue was purified by silica gel column chromatography (hexane/ethyl acetate=10/1→3/1). The obtained (1S,2R)-1-hydroxy-1,2,3-propanetricarboxylic acid 3-benzyl 1,2-diethyl ester was dissolved in 6 ml of pyridine, and 3 ml of acetic anhydride was added thereto, followed by stirring at room temperature for 12 hours. The reaction solution was evaporated to dryness under reduced pressure, and then residue was purified by silica gel column chromatography (hexane/ethyl acetate=3/1) to obtain 966 mg of the above-identified compound as colorless oily substance.

(2) Preparation of 1,2-diethyl (1S,2R)-1-acetoxy-1,2,3-propanetricarboxylate 966 mg of 3-benzyl 1,2-diethyl (1S,2R)-1-acetoxy-1,2,3-propanetricarboxylate was dissolved in 9 ml of ethanol, and 40 mg of a 10% palladium-carbon catalyst was added thereto, followed by catalytic reduction for 3 hours at room temperature under hydrogen atmospheric pressure. The catalyst was filtered off, and then, the solvent was distilled off under reduced pressure to obtain 737 mg of the above-identified compound as colorless oily substance.

REFERENCE EXAMPLE 8

Preparation of 2,3-dimethyl 1-methoxy-1,2,3-propanetricarboxylate (1) Preparation of 1-tert-butyl 2,3-dimethyl 1-methoxy-1,2,3-propanetricarboxylate To 10 ml of a tetrahydrofuran solution containing 731 mg of tert-butyl methoxy acetate, 3.33 ml of a 1.5M cyclohexane solution of lithium diisopropylamide was dropwise added at −78° C. under a nitrogen atmosphere, and then 5 ml of tetrahydrofuran containing 721 mg of dimethyl maleate was dropwise added thereto, followed by stirring at the same temperature for one hour. A saturated ammonium chloride aqueous solution was added to the reaction solution, and the mixture was extracted by an addition of ice water and ethyl acetate. Then, the organic layer was washed with a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1) to obtain 567 mg of the above-identified compound as slightly yellow oily substance.

(2) Preparation of 2,3-dimethyl 1-methoxy-1,2,3-propanetricarboxylate 567 mg of 1-tert-butyl 2,3-diemthyl 1-methoxy-1,2,3-propanetricarboxylate was dissolved in 3 ml of methylene chloride, and 3 ml of trifluoroacetic acid was added thereto, followed by stirring at room temperature for 2.5 hours. The reaction solution was evaporated to dryness under reduced pressure. Then, toluene was added to the residue, and the mixture was again evaporated to dryness under reduced pressure to obtain 457 mg of the above-identified compound as colorless oily substance.

REFERENCE EXAMPLE 9

Preparation of 6-methyl 3-methoxycarbonyl-4-methoxycarbonylmethyladipate (1) Preparation of 1-benzyl 6-methyl 3-methoxycarbonyl-4-methoxycarbonylmethyladipate To 5 ml of a tetrahydrofuran solution containing 600 mg of dimethyl 3-methoxycarbonylmethylglutarate, 1.36 ml of a 1.5M lithium diisopropylamide cyclohexane solution and 0.54 ml of hexamethylphosphoramide were dropwise added at −78° C. under a nitrogen atmosphere, followed by stirring at the same temperature for 1.5 hours. Then, a tetrahydrofuran solution containing 620 mg of benzyl bromoacetate was added thereto, followed by further stirring for one hour. The reaction solution was warmed to room temperature over a period of one hour and then stirred at the same temperature for 2 hours. A saturated ammonium chloride aqueous solution was added to the reaction solution, and the mixture was extracted with ethyl ether. Then, the organic layer was washed with a saturated sodium chloride aqueous solution and dried over anhydrous magnesium sulfate. The drying agent was filtered off, and then, the solvent was distilled off under reduced pressure. The residue was purified by medium pressure liquid column chromatography (hexane/ethyl acetate=3/1) to obtain 555 mg of the above-identified compound as colorless oily substance.

(2) Preparation of 6-methyl 3-methoxycarbonyl-4-methoxycarbonylmethyladipate 555 mg of 1-benzyl 6-methyl 3-methoxycarbonyl-4-methoxycarbonylmethyladipate was dissolved in 3 ml of 1,4-dioxane, and 198 mg of a 10% palladium-carbon catalyst was added thereto, followed by catalytic reduction for 12 hours at room temperature under hydrogen atmospheric pressure. The catalyst was filtered off, and then, the solvent was distilled off under reduced pressure to obtain 415 mg of the above-identified compound as colorless oily substance.

REFERENCE EXAMPLE 10

Preparation of (2S,3R)-5,5-diethoxy-3-(3,4-methylenedioxyphenyl)pentan-2-ol 31.98 g of (2RS,3RS)-5,5-diethoxy-3-(3,4-methylenedioxyphenyl)pentan-2-ol [synthesized by the same method as Reference Example 1(1) and (2) using 3,4-methylenedioxyphenylacetone and iodoacetaldehyde diethyl acetal as the starting materials] was dissolved in 320 ml of vinyl acetate, and 15.1 ml of triethylamine was added thereto. Then, 1.0 g of immobilized lipase (Toyothium LIP) was added thereto, followed by stirring at 30° C. for 16 hours. Further, 0.9 g of immobilized lipase was added thereto, followed by stirring at the same temperature for 46 hours. Then, insoluble matters were filtered off. The filtrate was diluted with ethyl acetate, then sequentially washed with 1N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=5/1→1/1) to obtain 16.05 g of the above-identified compound, $[\alpha]_D^{20}$ −31.8° (c 1.0, methanol) as colorless oily substance and 18.40 g of (2R,3S)-2-acetoxy-5,5-diethoxy-3-(3,4-methylenedioxyphenyl)pentane as colorless oily substance. Further, the absolute configuration of the above-identified compound was determined by Mosher method (J. Am. Chem. Soc., vol. 113, p. 4092 (1991)).

REFERENCE EXAMPLE 11

Preparation of (2S,3S)-3-tert-butoxycarbonyl-5-oxotetrahydrofuran-2-carboxylic Acid (1) Preparation of 3-tert-butyl 1,2-diethyl (1S,2R)-1-hydroxy-1,2,3-propanetricarboxylate 31 ml of a 1.69M hexane solution of n-butyl lithium was dissolved in 30 ml of tetrahydrofuran, and 7.1 ml of diisopropylamine was added under cooling with ice, followed by stirring at the same temperature for 30 minutes. Then, the mixture was cooled to −78° C. 20 ml of a tetrahydrofuran solution containing 4.94 g of diethyl (S)-malate was dropwise added at a temperature of not higher than −50° C., followed by stirring at −20° C. for 1.5 hours. The reaction solution was cooled to −78° C., and 20 ml of a tetrahydrofuran solution containing 5.58 g of tert-butyl bromoacetate and 4.66 g of hexamethylphosphoric triamide was dropwise added thereto at a temperature of not higher than −50° C., followed by stirring at room temperature for one hour. The reaction solution was poured into 150 ml of 0.5N hydrochloric acid and extracted with diethyl ether. Then, the organic layer was washed with a saturated sodium hydrogencarbonate aqueous solution and a saturated sodium chloride aqueous solution and then dried over anhydrous magnesium sulfate. The drying agent was filtered off, and then, the solvent was distilled off under reduced pressure. The residue was purified by silica gel column chromatography (hexane/ethyl acetate=5/1→4/1) to obtain 3.88 g of the above-identified compound as yellow oily substance.

(2) Preparation of (2S,3R)-5-oxotetrahydrofuran-2,3-dicarboxylic Acid 16.49 g of 3-tert-butyl 1,2-diethyl (1S,2R)-1-hydroxy-1,2,3-propanetricarboxylate, 100 ml of acetic acid and 50 ml of concentrated hydrochloric acid were mixed and stirred at 70° C. for 5 hours. Acetic acid and hydrochloric acid were distilled off under reduced pressure. Then, the residue was again dissolved in 100 ml of acetic acid and 50 ml of concentrated hydrochloric acid and stirred at 70° C. for 12 hours. Acetic acid and hydrochloric acid were distilled off under reduced pressure. Then, 100 ml of trifluoroacetic acid was added to the residue, followed by stirring at 60° C. for 5 hours. Trifluoroacetic acid was distilled off under reduced pressure, and the residue was crystallized from hexane-ethyl acetate to obtain 9.38 g of the above-identified compound as white powder.

(3) Preparation of (2S,3R)-2-benzyloxycarbonyl-5-oxotetrahydrofuran-3-carboxylic Acid 5.2 g of (2S,3R)-5-oxotetrahydrofuran-2,3-dicarboxylic acid was dissolved in 88 ml of acetone, and 6.5 g of 1,1'-dicyclohexylcarbodiimide was added thereto, followed by stirring at room temperature for 2 hours. 3.26 ml of benzyl alcohol was added to the reaction solution, and stirred at the same temperature for 12 hours. Insoluble mattes were filtered off, and the filtrate was concentrated under reduced pressure. The residue was purified by silica gel column chromatography (hexane/ethyl acetate=4/1→chloroform/methanol=50/1) to obtain 7.93 g of the above-identified compound as yellow solid.

(4) Preparation of 2-benzyl 3-tert-butyl (2S,3S)-5-oxotetrahydrofuran-2,3-dicarboxylate 7.93 g of (2S,3R)-2-benzyloxycarbonyl-5-oxotetrahydrofuran-3-carboxylic acid was dissolved in 75 ml of chloroform, and 5.5 g of 4-dimethylaminopyridine, 8.6 g of 1-ethyl-3-(3-dimethylaminopropyl)carbodiimide hydrochloride and 5.7 ml of tert-butyl alcohol were sequentially added thereto, followed by stirring at room temperature for 60 hours. The reaction solution was poured into 1N hydrochloric acid cooled with ice, and extracted with ethyl acetate. The organic layer was dried over anhydrous magnesium sulfate. The drying agent was filtered off, and then, the solvent was distilled off under reduced pressure. The residue was purified by silica gel column chromatography (hexane/ethyl acetate=5/1) to obtain 6.48 g of the above-identified compound as white solid.

(5) Preparation of (2S,3S)-3-tert-butoxycarbonyl-5-oxotetrahydrofuran-2-carboxylic Acid 6.4 g of 2-benzyl 3-tert-butyl (2S,3S)-5-oxotetrahydrofuran-2,3-dicarboxylate was dissolved in 80 ml of ethyl acetate, and 640 mg of a 10% palladium-carbon catalyst was added thereto, followed by catalytic reduction for 3 hours at room temperature under hydrogen atmospheric pressure. The catalyst was filtered off, and the filtrate was evaporated to dryness under reduced pressure to obtain 4.39 g of the above-identified compound as white solid.

REFERENCE EXAMPLE 12

Preparation of 2,3,4-triethyl (2RS,3SR)-1,2,3,4-butanetetracarboxylate 1.17 g of tetraethyl (2RS,3SR)-1,2,3,4-butanetetracarboxylate was dissolved in a mixed solution of 5 ml of ethanol and 5 ml of water, and 142 mg of lithium hydroxide monohydrate was added thereto, followed by stirring at room temperature overnight. Ethanol was distilled off under reduced pressure, and then diethyl ether was added thereto followed by liquid separation. The aqueous layer was separated and acidified by an addition of 1N hydrochloric acid and then extracted with diethyl ether. The organic layer was dried over anhydrous magnesium sulfate. The drying agent was filtered off, and then, the solvent was distilled off under reduced pressure. The residue was purified by silica gel column chromatography (chloroform/methanol=100/1→30/1) to obtain 460 mg of the above-identified compound as colorless oily substance.

REFERENCE EXAMPLE 13

Preparation of 2,4-diethyl 1-acetoxy-1,2,4-butantricarboxylate (1) Preparation of diethyl 4-hydroxy-4-phenyl-1,3-butanedicarboxylate 2.0 g of diethyl glutarate and 1.1 g of benzaldehyde were dissolved in 30 ml of tetrahydrofuran, and 8.5 ml of a 1.5M lithium diisopropylamide cyclohexane solution was dropwise added thereto at −78° C. under a nitrogen atmosphere, followed by stirring at the same temperature for 1.5 hours. A saturated ammonium chloride aqueous solution was added to the reaction solution, and the mixture was extracted with ethyl acetate. Then, the organic layer was washed with a saturated sodium chloride aqueous solution and dried over anhydrous magnesium sulfate. The drying agent was filtered off, and then, the solvent was distilled off under reduced pressure. The residue was purified by medium pressure liquid chromatography (Lobar column™, size C, Lichroprep™Si60, manufactured by Merck Co.; hexane/ethyl acetate=3/1) to obtain 1.56 g of the above-identified compound as colorless oily substance.

(2) Preparation of diethyl 4-acetoxy-4-phenyl-1,3-butanedicarboxylate 5 mg of dimethylaminopyridine was added to a mixed solution comprising 500 mg of diethyl 4-hydroxy-4-phenyl-1,3-butanedicarboxylate, 5 ml of pyridine and 1 ml of acetic anhydride, followed by stirring at room temperature overnight. 2N hydrochloric acid was added to the reaction solution, and then the mixture was extracted with ethyl acetate. The organic layer was washed sequentially with 2N hydrochloric acid, a saturated sodium hydrogencarbonate aqueous solution and a saturated sodium chloride aqueous solution and dried over anhydrous magnesium sulfate. The drying agent was filtered off, and then, the solvent was distilled off under reduced pressure. The residue was purified by silica gel column chromatography (hexane/ethyl acetate=4/1) to obtain 497 mg of the above-identified compound as colorless oily substance.

(3) Preparation of 2,4-diethyl 1-acetoxy-1,2,4-butanetricarboxylate 269 mg of diethyl 4-acetoxy-4-phenyl-1,3-butanedicarboxylate, 6 ml of carbon tetrachloride, 6 ml of acetonitrile and 8.9 ml of water were mixed, and 1.43 g of disodium phosphate dodecahydrate, 856 mg of sodium periodate and 25 mg of ruthenium chloride were added under cooling with ice, followed by stirring at room temperature for 15 hours. 30 mg of ruthenium chloride and 500 mg of sodium periodate were added thereto, followed by stirring for 24 hours. Then, 30 mg of ruthenium chloride was again added, followed by stirring for further 24 hours. Insoluble matters were separated by filtration and washed with a saturated sodium hydrogencarbonate aqueous solution and chloroform. The filtrate and the washing solution were combined, whereupon the aqueous layer was separated. The obtained aqueous layer was acidified with 3N hydrochloric acid and then extracted with ethyl ether. The organic layer was washed with a saturated sodium thiosulfate aqueous solution and a saturated sodium chloride aqueous solution and then dried over anhydrous magnesium sulfate. The drying agent was filtered off, and then, the solvent was distilled off under reduced pressure to obtain 128 mg of the above-identified compound as white solid.

REFERENCE EXAMPLE 14

Preparation of (2RS,3SR)-3-tert-butoxycarbonyl-5-oxotetrahydrofuran-2-carboxylic Acid (1) Preparation of 2-benzyl 3-tert-butyl (2RS,3SR)-5-oxotetrahydrofuran-2,3-dicarboxylate 3.38 g of (2RS,3SR)-2-benzyloxycarbonyl-5-oxotetrahydrofuran-3-carboxylic acid obtained by carrying out the same reaction as in Reference Example 11(3) except that in Reference Example 11(3) commercially available (4RS,5SR)-2-oxotetrahydrofuran-4,5-dicarboxylic acid was used as the starting material, was dissolved in 100 ml of tetrahydrofuran, and 7.69 g of N,N'-diisopropyl-O-tert-butylisourea was added thereto, followed by stirring at room temperature for 4 days. Insoluble matters were filtered off, and then the filtrate was concentrated under reduced pressure. The residue was purified by silica gel column chromatography (hexane/ethyl acetate=5/1) to obtain 2.70 g of the above-identified compound as colorless oily substance.

(2) Preparation of (2RS,3SR)-3-tert-butoxycarbonyl-5 -oxotetrahydrofuran-2-carboxylic Acid 2.70 g of 2-benzyl 3-tert-butyl (2RS,3SR)-5-oxotetrahydrofuran-2,3-dicarboxylate was dissolved in 30 ml of ethyl acetate, and 300 mg of a 10% palladium-carbon catalyst was added thereto, followed by catalytic reduction for 3 hours at room temperature under hydrogen atmospheric pressure. The catalyst was filtered off, and the filtrate was evaporated to dryness under reduced pressure to obtain 1.86 g of the above-identified compound as white solid.

INDUSTRIAL APPLICABILITY

The compounds of the present invention have excellent inhibitory activities against protein-farnesyl transferase (PFT) and thus are useful as antitumor agents.

We claim:

1. A compound of the formula (I) or its pharmaceutically acceptable salt or ester:

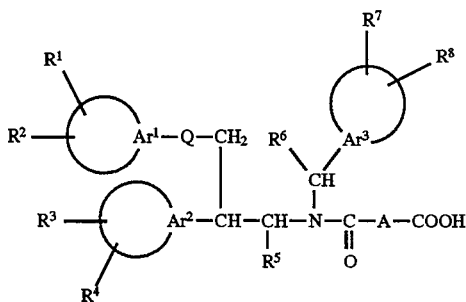 (I)

wherein each of

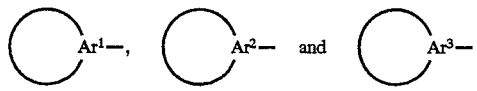

which are the same or different, is an aryl group or a heteroaromatic ring group; A is a $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group; Q is a group of the formula —$(CH_2)_m$— (wherein m is an integer of from 1 to 6) or —$(CH_2)_n$—W—$(CH_2)_p$— (wherein W is an oxygen atom, a sulfur atom, a vinylene group or an ethynylene group; and each of n and p which are the same or different, is an integer of from 0 to 3); $R^1$ is a hydrogen atom, a halogen atom, a hydroxyl group, a lower alkyl group, a lower alkoxy group, or an aryl or heteroaromatic ring group which may have substituent(s) selected from the group consisting of a halogen atom, a lower alkyl group and a lower alkoxy group; each of $R^2$, $R^7$ and $R^8$ which are the same or different, is a hydrogen atom, a halogen atom, a hydroxyl group, a lower alkyl group or a lower alkoxy group; each of $R^3$ and $R^4$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^5$ is a lower alkyl group; and $R^6$ is a hydrogen atom or a lower alkyl group.

2. The compound according to claim 1, wherein

is a phenyl group, a naphthyl group, a benzofuranyl group, a benzothienyl group or a benzoxazolyl group.

3. The compound according to claim 1, wherein

is a phenyl group.

4. The compound according to claim 1, wherein

is a naphthyl group, a benzofuranyl group or a benzothienyl group.

5. The compound according to claim 1, wherein A is a group of the formula (a):

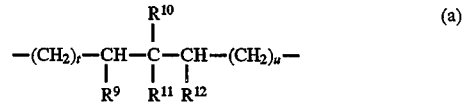 (a)

wherein $R^9$ is a hydrogen atom, a hydroxyl group, a lower hydroxyalkyl group a lower alkoxy group or a carboxyl group; $R^{10}$ is a hydrogen atom, a hydroxyl group, a lower alkoxy group, a carboxyl group or a lower carboxyalkyl group; $R^{11}$ is a hydrogen atom, a lower hydroxyalkyl group or a carboxyl group; $R^{12}$ is a hydrogen atom, a hydroxyl group or a carboxyl group; and each of t and u which are the same or different, is an integer of from 0 to 2.

6. The compound according to claim 1, wherein A is a group of the formula (b):

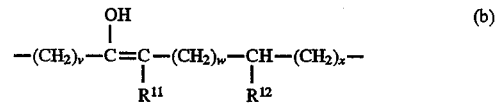 (b)

wherein $R^{11}$ is a hydrogen atom, a lower hydroxyalkyl group or a carboxyl group; $R^{12}$ is a hydrogen atom, a hydroxyl group or a carboxyl group; v is 0 or 1; and each of w and x which are the same or different, is an integer of from 0 to 2.

7. An antitumor agent which comprises a compound of the formula (I) or its pharmaceutically acceptable salt or ester:

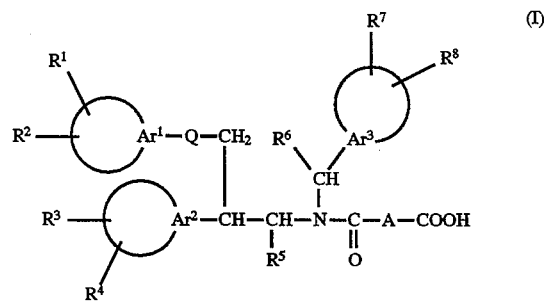 (I)

wherein each of

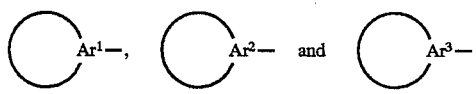

which are the same or different, is an aryl group or a heteroaromatic ring group; A is a $C_{2-8}$ saturated or unsaturated aliphatic hydrocarbon group which may have substituent(s) selected from the group consisting of a lower alkyl group, a hydroxyl group, a lower hydroxyalkyl group, a lower alkoxy group, a carboxyl group, a lower carboxyalkyl group, an aryl group and an aralkyl group; Q is a group of the formula —$(CH_2)_m$— (wherein m is an integer of from 1 to 6) or —$(CH_2)_n$—W—$(CH_2)_p$— (wherein W is an oxygen atom, a sulfur atom, a vinylene group or an ethynylene group; and each of n and p which are the same or different, is an integer of from 0 to 3); $R^1$ is a hydrogen atom, a halogen atom, a hydroxyl group, a lower alkyl group, a lower alkoxy group, or an aryl or heteroaromatic ring group which may have substituent(s) selected from the group consisting of a halogen atom, a lower alkyl group and a lower alkoxy group; each of $R^2$, $R^7$ and $R^8$ which are the same or different, is a hydrogen atom, a halogen atom, a hydroxyl group, a lower alkyl group or a lower alkoxy group; each of $R^3$ and $R^4$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^5$ is a lower alkyl group; and $R^6$ is a hydrogen atom or a lower alkyl group, as an active ingredient.

* * * * *